(12) United States Patent
Dong et al.

(10) Patent No.: US 8,039,435 B2
(45) Date of Patent: Oct. 18, 2011

(54) MELANOCORTIN RECEPTOR LIGANDS

(75) Inventors: Zheng Xin Dong, Holliston, MA (US); Jacques-Pierre Moreau, Upton, MA (US)

(73) Assignee: Ipsen Pharma S.A.S., Boulogne (FR)

( * ) Notice: Subject to any disclaimer, the term of this patent is extended or adjusted under 35 U.S.C. 154(b) by 460 days.

(21) Appl. No.: 11/988,533

(22) PCT Filed: Jul. 10, 2006

(86) PCT No.: PCT/US2006/026586
§ 371 (c)(1),
(2), (4) Date: May 15, 2009

(87) PCT Pub. No.: WO2007/008704
PCT Pub. Date: Jan. 18, 2007

(65) Prior Publication Data
US 2010/0279922 A1    Nov. 4, 2010

Related U.S. Application Data

(60) Provisional application No. 60/697,779, filed on Jul. 8, 2005, provisional application No. 60/748,850, filed on Dec. 9, 2005.

(51) Int. Cl.
*A61K 38/00* (2006.01)
(52) U.S. Cl. .................. 514/10.7; 514/21.1; 514/21.7; 530/317; 530/328
(58) Field of Classification Search .................. None
See application file for complete search history.

(56) References Cited

U.S. PATENT DOCUMENTS

| | | | |
|---|---|---|---|
| 6,127,381 | A | 10/2000 | Basu et al. |
| 6,350,430 | B1 | 2/2002 | Dooley et al. |
| 6,613,874 | B1 | 9/2003 | Mazur et al. |
| 6,951,916 | B2 | 10/2005 | Mazur et al. |
| 2003/0113263 | A1 | 6/2003 | Marks et al. |
| 2003/0212002 | A1 | 11/2003 | Haskell-Luevano et al. |
| 2004/0138136 | A1 | 7/2004 | Sharma et al. |
| 2004/0260063 | A1 | 12/2004 | Haskell-Luevano |
| 2007/0123453 | A1 | 5/2007 | Heiman et al. |

FOREIGN PATENT DOCUMENTS

| WO | 98/37097 | | 8/1998 |
|---|---|---|---|
| WO | 2005/000338 | | 1/2005 |
| WO | WO 2005000338 | A1 * | 1/2005 |
| WO | 2005/019184 | | 3/2005 |
| WO | 2005/019212 | | 3/2005 |
| WO | 2005/000339 | | 6/2005 |
| WO | 2005/054279 | | 6/2005 |
| WO | 2006/037188 | | 4/2006 |
| WO | 2006/073771 | | 7/2006 |
| WO | 2006/073772 | | 7/2006 |
| WO | 2007/022774 | | 3/2007 |
| WO | 2005/102377 | | 11/2010 |

OTHER PUBLICATIONS

Haskell-Luevano, "Biological and conformational examination of stereochemical modifications using the template melanotropin peptide, Ac-Nle-c[Asp-His-Phe-Arg-Trp-Ala-Lys]-NH2, on human melanocortin receptors", J. Med. Chem, 1997, 40:1738-48.

Kask, "Selective antagonist for the melanocortin 4 receptor (HS014) increases food intake in free-feeding rats", Biochem. Biophys. Res. Comm., 1998, 245:90-3.

Navarro, "Effects of melanocortin receptor activation and blockade on ethanol intake: A possible role for the melanocortin-4 receptor", Alcohol Clin. Exp. Res., 2005, 29:949-57.

Nikiforovich, "Studies of conformational isomerism in alpha-melanocyte stimulating hormone by design of cyclic analogues", Biopolymers, 1998, 46:155-67.

Wilczynski, A. et al., "Structure-activity relationships of the unique and potent agouti-related protein (AGRP)-melanocortin chimeric Tyr-c[β-Asp-His-DPhe-Arg-Trp-Asn-Ala-Phe-Dpr]-Tyr-NH$_2$ peptide template", J. Med. Chem., 2005, 48:3060-3075.

Hruby, V. J. et al., "Design of potent and specific melanotropin agonists and antagonists: investigating ligands for new receptors", Peptides, 1996, p. 485-486.

Hruby, V. J. et al., "Designing potent and selective melanotropin agonist and antagonist ligands for the recently discovered melanocortin 3, 4 and 5 receptors", Peptides, 1998, p. 70-71.

Mayer, J. P. et al., "Discovery of a B-MSH-derived MC-4R selective agonist", J. Med. Chem., 2005, 48:3095-3098.

Yan, L. Z. et al., "Potent and selective MC-4 receptor agonists based on a novel disulfide scaffold", Bioorganic & Medicinal Chem. Lett., 15:4611-4614, (Oct. 15, 2005).

* cited by examiner

*Primary Examiner* — Anish Gupta
*Assistant Examiner* — Jeanette Lieb
(74) *Attorney, Agent, or Firm* — Yankwich & Associates; Alan F. Feeney; Pamela C. Ball

(57) ABSTRACT

The present invention is directed to compounds according to formula, $$(R^2R^3)-A^1-c(A^2-A^3-A^4-A^5-A^6-A^7-A^8-A^9)-A^{10}-R^1,$$

and pharmaceutically-acceptable salts thereof that act as ligands for one or more of the melanocortin receptors, to methods of using such compounds to treat mammals and to pharmaceutical compositions comprising said compounds.

2 Claims, 8 Drawing Sheets

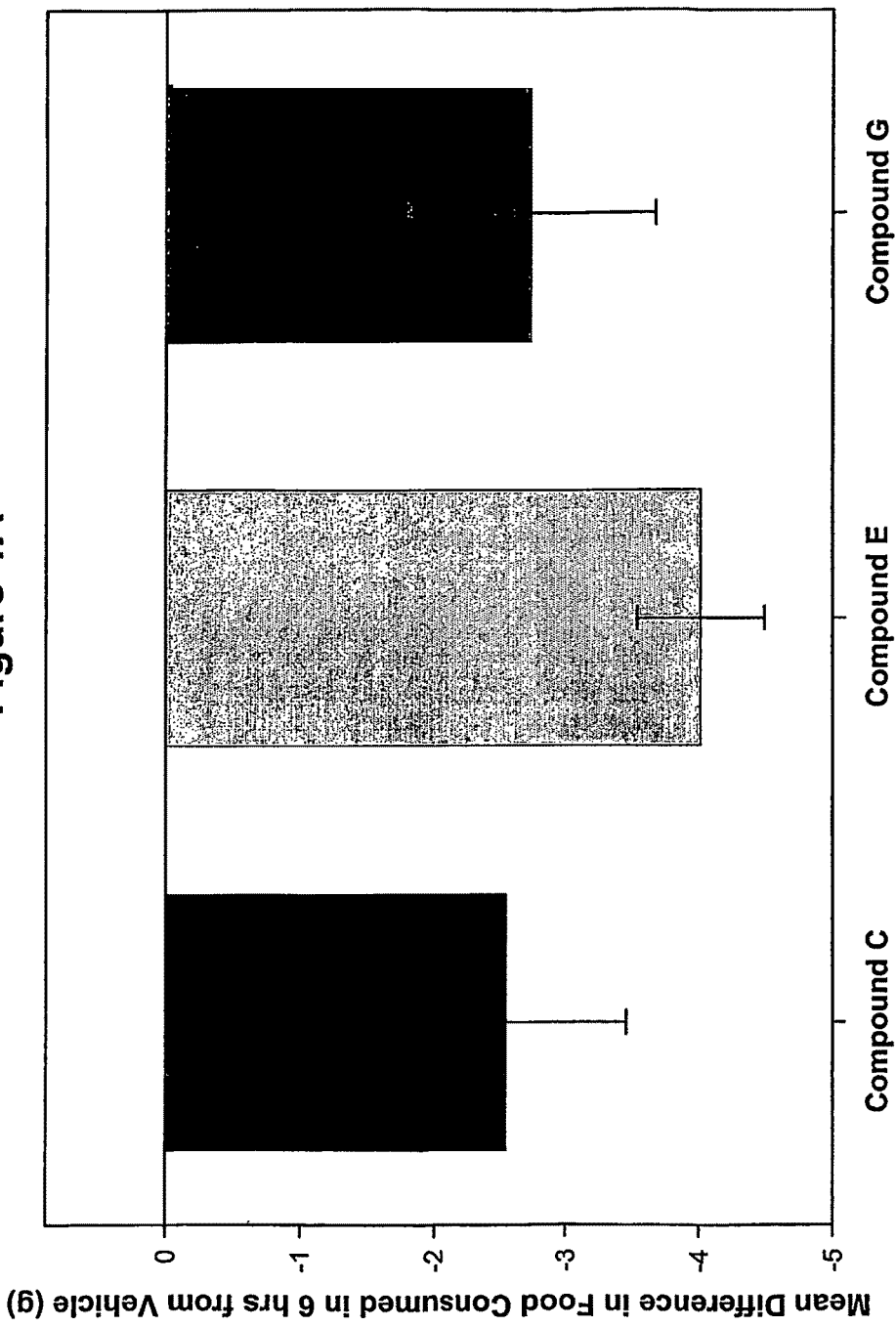

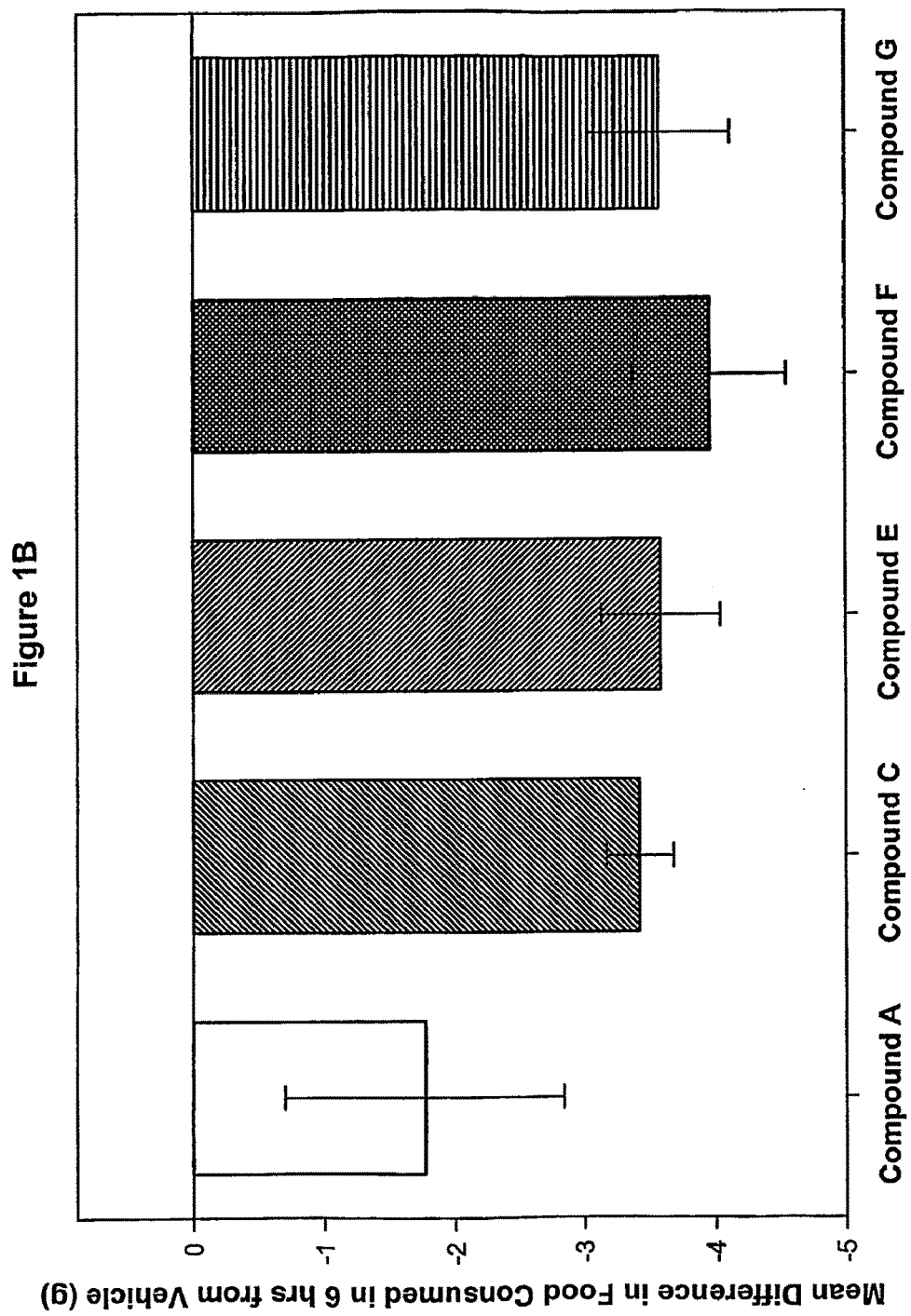

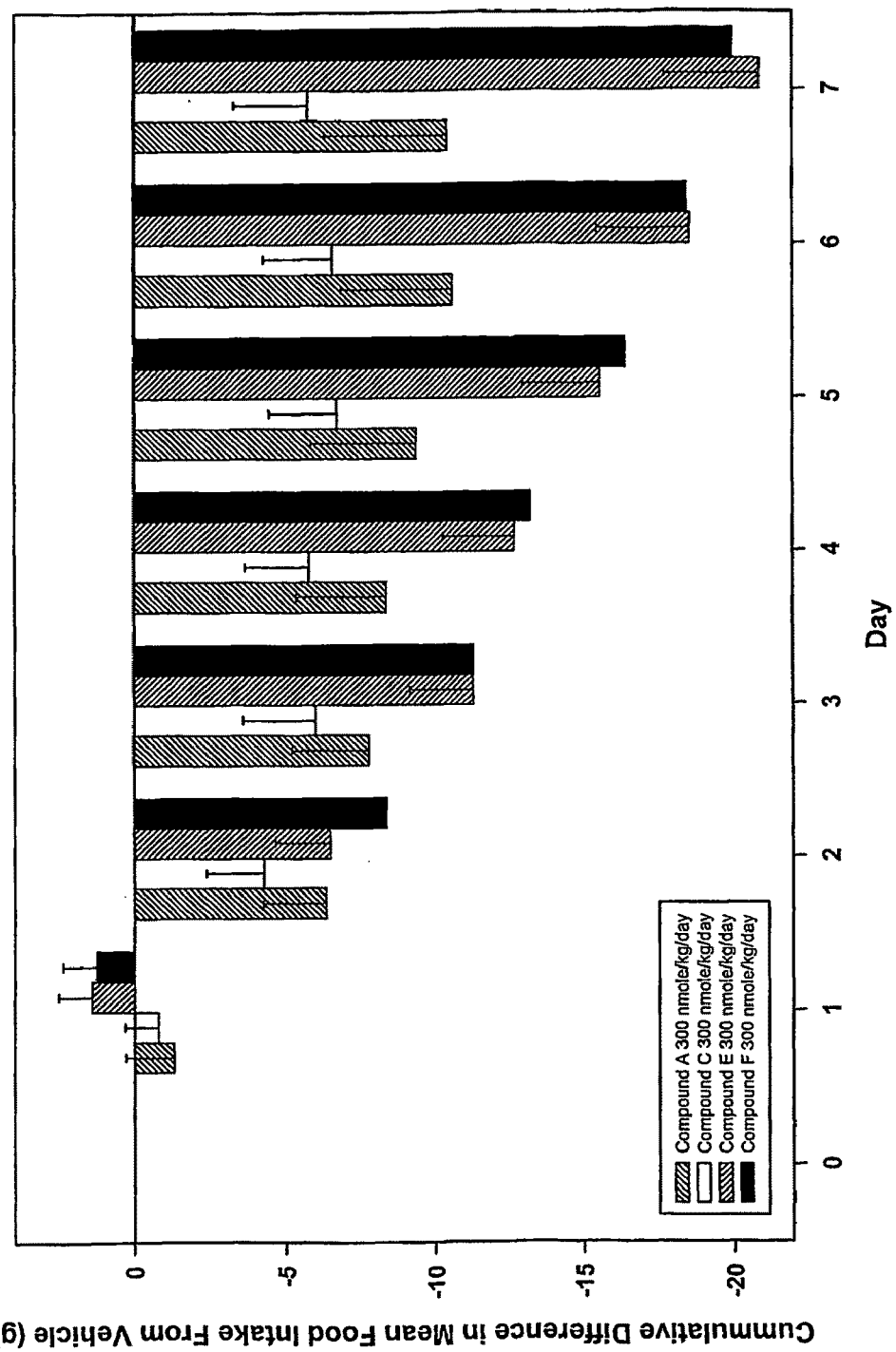

SEQUENCE LISTING

<160> NUMBER OF SEQ ID NOS: 61

<210> SEQ ID NO 1
<211> LENGTH: 8
<212> TYPE: PRT
<213> ORGANISM: Artificial Sequence
<220> FEATURE:

```
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = beta-Ala or 1-amino-1-
      cyclohexanecarboxylic acid (A6c)
<220> FEATURE:
<221> NAME/KEY: MOD_RES
<222> LOCATION: (8)..(8)
<223> OTHER INFORMATION: AMIDATION

<400> SEQUENCE: 1

Xaa Asp His Xaa Arg Trp Xaa Lys
1               5

<210> SEQ ID NO 2
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 6-aminohexanoic acid (Ahx) or
      5-aminopentanoic acid (Apn)
<220> FEATURE:
<221> NAME/KEY: MOD_RES
<222> LOCATION: (8)..(8)
<223> OTHER INFORMATION: AMIDATION

<400> SEQUENCE: 2

Xaa Cys His Xaa Arg Trp Xaa Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
```

```
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = Ala, beta-Ala or 4-aminobutyric acid
      (Gaba)
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MOD_RES
<222> LOCATION: (9)..(9)
<223> OTHER INFORMATION: AMIDATION

<400> SEQUENCE: 3

Xaa Cys His Xaa Arg Trp Xaa Xaa Thr
1               5

<210> SEQ ID NO 4
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 5-aminopentanoic acid (Apn)
<220> FEATURE:
<221> NAME/KEY: MOD_RES
<222> LOCATION: (8)..(8)
<223> OTHER INFORMATION: AMIDATION

<400> SEQUENCE: 4

Xaa Asp His Xaa Arg Trp Xaa Lys
1               5

<210> SEQ ID NO 5
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = 1-amino-1-cyclohexanecarboxylic acid
      (A6c) modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
```

```
<223> OTHER INFORMATION: AMIDATION

<400> SEQUENCE: 5

Xaa Asp His Xaa Arg Trp Xaa Lys
1               5

```
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = D-Cys
<220> FEATURE:
<221> NAME/KEY: MISC_FEATURE
<222> LOCATION: (3)..(3)
<223> OTHER INFORMATION: Xaa = Ala, D-Ala, beta-Ala, 4-aminobutyric acid
      (Gaba), alpha-aminoisobutyric acid (Aib) or Gly
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: AMIDATION

<400> SEQUENCE: 8

Xaa Xaa Xaa His Xaa Arg Trp Cys
1               5

<210> SEQ ID NO 9
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala, beta-Ala, 4-aminobutyric acid
      (Gaba), alpha-aminoisobutyric acid (Aib) or Gly
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MOD_RES
<222> LOCATION: (8)..(8)
<223> OTHER INFORMATION: AMIDATION

<400> SEQUENCE: 9

Xaa Cys Xaa His Xaa Arg Trp Xaa
1               5

<210> SEQ ID NO 10
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
```

```
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = D-Cys
<220> FEATURE:
<221> NAME/KEY: MISC_FEATURE
<222> LOCATION: (3)..(3)
<223> OTHER INFORMATION: Xaa = Ala, D-Ala, beta-Ala, 4-aminobutyric acid
      (Gaba) or alpha-aminoisobutyric acid (Aib)
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MOD_RES
<222> LOCATION: (8)..(8)
<223> OTHER INFORMATION: AMIDATION

<400> SEQUENCE: 10

Xaa Xaa Xaa His Xaa Arg Trp Xaa
1               5

<210> SEQ ID NO 11
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = octahydroindole-2-carboxylic acid (Oic),
      cyclohexylGly (Chg), homo-cyclohexylAla (hCha),
      D-betacyclohexylAla (D-Cha), nipecotic acid (Nip), homo-Pro
      (hPro), homo-Leu (hLeu), Phe, D-Phe, D-cyclohexylGly (D-Chg),
      homo-Phe (hPhe), beta-homoMet (beta-hMet) or 4-aminobutyric acid
      (Gaba), all modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 11

Xaa Asp His Xaa Arg Trp Xaa Lys
1               5

<210> SEQ ID NO 12
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
```

-continued

```
<222> LOCATION: (1)..(1)
<223> OTHER INFORMATION: Xaa = beta-cyclohexylAla (Cha) modified with
      n-butanoyl
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 12

Xaa Asp His Xaa Arg Trp Xaa Lys
1               5

<210> SEQ ID NO 13
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = beta-cyclohexylAla (Cha),
      homo-cyclohexylAla (hCha), Leu, homo-Leu (hLeu) or Phe, all
      modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (6)..(6)
<223> OTHER INFORMATION: Xaa = D-Trp
<220> FEATURE:
<221> NAME/KEY: MOD_RES
<222> LOCATION: (8)..(8)
<223> OTHER INFORMATION: AMIDATION

<400> SEQUENCE: 13

Xaa Asp His Xaa Arg Xaa Ala Lys
1               5

<210> SEQ ID NO 14
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
```

```
<221> NAME/KEY: MISC_FEATURE
<222> LOCATION: (6)..(6)
<223> OTHER INFORMATION: Xaa = D-Trp
<220> FEATURE:
<221> NAME/KEY: MISC_FEATURE
<222> LOCATION: (7)..(7)
<223> OTHER INFORMATION: Xaa = D-Ala, beta-Ala, 4-aminobutyric acid
      (Gaba), 7-aminoheptanoic acid (Aha) or 5-aminopentanoic acid (Apn)
<220> FEATURE:
<221> NAME/KEY: MOD_RES
<222> LOCATION: (8)..(8)
<223> OTHER INFORMATION: AMIDATION

<400> SEQUENCE: 14

Xaa Asp His Xaa Arg Xaa Xaa Lys
1               5

<210> SEQ ID NO 15
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (6)..(6)
<223> OTHER INFORMATION: Xaa = D-Trp
<220> FEATURE:
<221> NAME/KEY: MISC_FEATURE
<222> LOCATION: (7)..(7)
<223> OTHER INFORMATION: Xaa = 5-aminopentanoic acid (Apn),
      4-aminobutyric acid (Gaba), 6-aminohexanoic acid (Ahx), beta-Ala,
      D-Ala
<220> FEATURE:
<221> NAME/KEY: MOD_RES
<222> LOCATION: (8)..(8)
<223> OTHER INFORMATION: AMIDATION

<400> SEQUENCE: 15

Xaa Cys His Xaa Arg Xaa Xaa Cys
1               5

<210> SEQ ID NO 16
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-beta-(2-naphthyl)Ala (D-2-Nal)
```

-continued

```
<220> FEATURE:
<221> NAME/KEY: MISC_FEATURE
<222> LOCATION: (7)..(7)
<223> OTHER INFORMATION: Xaa = Trp, beta-(2-naphthyl)Ala (2-Nal) or
      beta-(1-naphthyl)Ala (1-Nal)
<220> FEATURE:
<221> NAME/KEY: MOD_RES
<222> LOCATION: (8)..(8)
<223> OTHER INFORMATION: AMIDATION

<400> SEQUENCE: 16

Xaa Cys Xaa His Xaa Arg Xaa Cys
1               5

<210> SEQ ID NO 17
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with n-butanoyl
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = beta-(2-naphthyl)Ala (2-Nal) or Trp
<220> FEATURE:
<221> NAME/KEY: MOD_RES
<222> LOCATION: (8)..(8)
<223> OTHER INFORMATION: AMIDATION

<400> SEQUENCE: 17

Xaa Cys Xaa His Xaa Arg Xaa Cys
1               5

<210> SEQ ID NO 18
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = beta-(2-naphthyl)Ala (2-Nal),
      beta-(1-naphthyl)Ala (1-Nal) or 3-benzothienylAla (Bal)
```

```
<220> FEATURE:
<221> NAME/KEY: MOD_RES
<222> LOCATION: (8)..(8)
<223> OTHER INFORMATION: AMIDATION

<400> SEQUENCE: 18

Xaa Cys Xaa His Xaa Arg Xaa Cys
1               5

<210> SEQ ID NO 19
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = D-Ala
<220> FEATURE:
<221> NAME/KEY: MOD_RES
<222> LOCATION: (8)..(8)
<223> OTHER INFORMATION: AMIDATION

<400> SEQUENCE: 19

Xaa Asp His Xaa Arg Trp Xaa Lys
1               5

<210> SEQ ID NO 20
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-beta-2-naphthylAla (D-2-Nal)
<220> FEATURE:
<221> NAME/KEY: MISC_FEATURE
<222> LOCATION: (7)..(7)
<223> OTHER INFORMATION: Xaa = 3-benzothienylAla (Bal)
<220> FEATURE:
<221> NAME/KEY: MOD_RES
<222> LOCATION: (8)..(8)
<223> OTHER INFORMATION: AMIDATION

<400> SEQUENCE: 20

Xaa Cys Xaa His Xaa Arg Xaa Cys
1               5
```

```
<210> SEQ ID NO 21
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = penicillamine (Pen)
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: AMIDATION

<400> SEQUENCE: 21

Xaa Xaa Xaa His Xaa Arg Trp Cys
1               5

<210> SEQ ID NO 22
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = Cys or penicillamine (Pen)
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = penicillamine (Pen)
<220> FEATURE:
<221> NAME/KEY: MOD_RES
<222> LOCATION: (8)..(8)
<223> OTHER INFORMATION: AMIDATION

<400> SEQUENCE: 22

Xaa Xaa Xaa His Xaa Arg Trp Xaa
1               5

<210> SEQ ID NO 23
```

```
<211> LENGTH: 9
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MOD_RES
<222> LOCATION: (9)..(9)
<223> OTHER INFORMATION: AMIDATION

<400> SEQUENCE: 23

Xaa Cys His Xaa Xaa Trp Xaa Xaa Thr
1               5

<210> SEQ ID NO 24
<211> LENGTH: 9
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-(Et)Tyr
<220> FEATURE:
<221> NAME/KEY: MISC_FEATURE
<222> LOCATION: (5)..(5)
<223> OTHER INFORMATION: Xaa = Arg or homo-Arg (hArg)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MOD_RES
<222> LOCATION: (9)..(9)
<223> OTHER INFORMATION: AMIDATION

<400> SEQUENCE: 24

Xaa Cys His Xaa Xaa Trp Xaa Xaa Thr
1               5
```

```
<210> SEQ ID NO 25
<211> LENGTH: 9
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (6)..(6)
<223> OTHER INFORMATION: Xaa = 4,4'-biphenylAla (Bip)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MOD_RES
<222> LOCATION: (9)..(9)
<223> OTHER INFORMATION: AMIDATION

<400> SEQUENCE: 25

Xaa Cys His Xaa Arg Xaa Xaa Xaa Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe or D-(Et)Tyr
<220> FEATURE:
<221> NAME/KEY: MISC_FEATURE
<222> LOCATION: (5)..(5)
<223> OTHER INFORMATION: Xaa = homo-Arg (hArg)
<220> FEATURE:
<221> NAME/KEY: MISC_FEATURE
<222> LOCATION: (6)..(6)
<223> OTHER INFORMATION: Xaa = 4,4'-biphenylAla (Bip)
<220> FEATURE:
<221> NAME/KEY: MISC_FEATURE
<222> LOCATION: (7)..(7)
<223> OTHER INFORMATION: Xaa = beta-Ala
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MOD_RES
<222> LOCATION: (9)..(9)
<223> OTHER INFORMATION: AMIDATION
```

```
<400> SEQUENCE: 26

Xaa Cys His Xaa Xaa Xaa Xaa Xaa Thr
1               5

<210> SEQ ID NO 27
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 5-aminopentanoic acid (Apn)
<220> FEATURE:
<221> NAME/KEY: MOD_RES
<222> LOCATION: (8)..(8)
<223> OTHER INFORMATION: AMIDATION

<400> SEQUENCE: 27

Xaa Cys His Xaa Arg Trp Xaa Cys
1               5

<210> SEQ ID NO 28
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = Trp or 3-benzothienylAla (Bal)
<220> FEATURE:
<221> NAME/KEY: MOD_RES
<222> LOCATION: (8)..(8)
<223> OTHER INFORMATION: AMIDATION

<400> SEQUENCE: 28

Xaa Asp Xaa His Xaa Arg Xaa Lys
1               5

<210> SEQ ID NO 29
<211> LENGTH: 8
<212> TYPE: PRT
```

```
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = penicillamine (Pen) or Cys
<220> FEATURE:
<221> NAME/KEY: MOD_RES
<222> LOCATION: (8)..(8)
<223> OTHER INFORMATION: C-terminus is the free acid

<400> SEQUENCE: 29

Xaa Cys Xaa His Xaa Arg Trp Xaa
1               5

<210> SEQ ID NO 30
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-alpha-aminobutyric acid (D-Abu), D-Val,
      D-Ile, D-Leu, D-tert-Leu (D-Tle) or D-beta-cyclohexylAla (D-Cha)
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: AMIDATION

<400> SEQUENCE: 30

Xaa Cys Xaa His Xaa Arg Trp Cys
1               5

<210> SEQ ID NO 31
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
```

```
<222> LOCATION: (2)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = penicillamine (Pen)
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 31

Xaa Xaa His Xaa Arg Trp Xaa Cys
1               5

<210> SEQ ID NO 32
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = Cys or penicillamine (Pen)
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (8)..(8)
<223> OTHER INFORMATION: Xaa = penicillamine (Pen)
<220> FEATURE:
<221> NAME/KEY: MOD_RES
<222> LOCATION: (8)..(8)
<223> OTHER INFORMATION: AMIDATION

<400> SEQUENCE: 32

Xaa Xaa His Xaa Arg Trp Xaa Xaa
1               5

<210> SEQ ID NO 33
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Leu, beta-cyclohexylAla (Cha), Ile, Phe,
      Val or beta-(2-naphthyl)Ala (2-Nal), all modified with acyl (Ac)
<220> FEATURE:
<221> NAME/KEY: DOMAIN
<222> LOCATION: (2)..(8)
```

```
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 33

Xaa Cys His Xaa Arg Trp Xaa Cys
1               5

<210> SEQ ID NO 34
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle or Phe
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 34

Xaa Cys His Xaa Arg Trp Xaa Cys
1               5

<210> SEQ ID NO 35
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa =  beta-(3-pyridiyl)Ala (3-Pal)
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
```

```
<221> NAME/KEY: MOD_RES
<222> LOCATION: (8)..(8)
<223> OTHER INFORMATION: AMIDATION

<400> SEQUENCE: 35

Xaa Cys Xaa Xaa Arg Trp Xaa Cys
1               5

<210> SEQ ID NO 36
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: C-terminus is the free acid

<400> SEQUENCE: 36

Xaa Cys Xaa His Xaa Arg Trp Cys
1               5

<210> SEQ ID NO 37
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (6)..(6)
<223> OTHER INFORMATION: Xaa = D-Trp
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 37

Xaa Cys His Phe Arg Xaa Xaa Cys
1               5

<210> SEQ ID NO 38
<211> LENGTH: 8
<212> TYPE: PRT
<213> ORGANISM: Artificial Sequence
```

```
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (7)..(7)
<223> OTHER INFORMATION: Xaa = Ala or beta-Ala
<220> FEATURE:
<221> NAME/KEY: MOD_RES
<222> LOCATION: (8)..(8)
<223> OTHER INFORMATION: AMIDATION

<400> SEQUENCE: 38

Xaa Asp His Xaa Arg Trp Xaa Lys
1               5

<210> SEQ ID NO 39
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (7)..(7)
<223> OTHER INFORMATION: Xaa = 4-aminobutyric acid (Gaba) or
      6-aminohexanoic acid (Ahx)
<220> FEATURE:
<221> NAME/KEY: MOD_RES
<222> LOCATION: (8)..(8)
<223> OTHER INFORMATION: AMIDATION

<400> SEQUENCE: 39

Xaa Cys His Xaa Arg Trp Xaa Cys
1               5

<210> SEQ ID NO 40
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = homo-Phe (hPhe) or beta-cyclohexylAla
      (Cha), both modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
```

```
<222> LOCATION: (4)..(4)
<223> OTHER INFORMATION: Xaa = D-beta-(2-naphthyl)Ala (D-2-Nal)
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 40

Xaa Asp His Xaa Arg Trp Xaa Lys
1               5

<210> SEQ ID NO 41
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = beta-Ala or 5-aminopentanoic acid (Apn)
<220> FEATURE:
<221> NAME/KEY: MOD_RES
<222> LOCATION: (8)..(8)
<223> OTHER INFORMATION: C-terminus is the free acid

<400> SEQUENCE: 41

Xaa Asp His Xaa Arg Trp Xaa Lys
1               5

<210> SEQ ID NO 42
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 6-aminohexanoic acid (Ahx) or
     5-aminopentanoic acid (Apn)
<220> FEATURE:
<221> NAME/KEY: MOD_RES
<222> LOCATION: (8)..(8)
<223> OTHER INFORMATION: C-terminus is the free acid

<400> SEQUENCE: 42
```

```
Xaa Cys His Xaa Arg Trp Xaa Cys
1               5
```

<210> SEQ ID NO 43
<211> LENGTH: 9
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = D-Phe
<220> FEATURE:
<221> NAME/KEY: DOMAIN
<222> LOCATION: (2)..(9)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = Ala, beta-Ala or 4-aminobutyric acid
      (Gaba)
<220> FEATURE:
<221> NAME/KEY: MISC_FEATURE
<222> LOCATION: (8)..(8)
<223> OTHER INFORMATION: Xaa = D-Cys
<220> FEATURE:
<221> NAME/KEY: MOD_RES
<222> LOCATION: (9)..(9)
<223> OTHER INFORMATION: C-terminus is the free acid

<400> SEQUENCE: 43

```
Xaa Cys His Xaa Arg Trp Xaa Xaa Thr
1               5
```

<210> SEQ ID NO 44
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = beta-cyclohexylAla (Cha), Nle,
      cyclohexylGly (Chg), D-beta-cyclohexylAla (D-Cha),
      homo-cyclohexylAla (hCha), D-cyclohexylGly(D-Chg) or homo-Phe
      (hPhe), all modified with acyl(Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: C-terminus is the free acid

<400> SEQUENCE: 44

```
Xaa Asp His Xaa Arg Trp Xaa Lys
1               5
```

<210> SEQ ID NO 45
<211> LENGTH: 8

```
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (6)..(6)
<223> OTHER INFORMATION: Xaa = D-Trp
<220> FEATURE:
<221> NAME/KEY: MISC_FEATURE
<222> LOCATION: (7)..(7)
<223> OTHER INFORMATION: Xaa = 4-aminobutyric acid (Gaba),
      6-aminohexanoic acid (Ahx), beta-Ala or D-Ala
<220> FEATURE:
<221> NAME/KEY: MOD_RES
<222> LOCATION: (8)..(8)
<223> OTHER INFORMATION: C-terminus is the free acid

<400> SEQUENCE: 45

Xaa Cys His Xaa Arg Xaa Xaa Cys
1               5

<210> SEQ ID NO 46
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-beta-(2-naphthyl)Ala (D-2-Nal)
<220> FEATURE:
<221> NAME/KEY: MISC_FEATURE
<222> LOCATION: (7)..(7)
<223> OTHER INFORMATION: Xaa = Trp, beta-(2-naphthyl)Ala (2-Nal),
      beta-(1-naphthyl)Ala (1-Nal) or 3-benzothienylalanine (Bal)
<220> FEATURE:
<221> NAME/KEY: MOD_RES
<222> LOCATION: (8)..(8)
<223> OTHER INFORMATION: C-terminus is the free acid

<400> SEQUENCE: 46

Xaa Cys Xaa His Xaa Arg Xaa Cys
1               5

<210> SEQ ID NO 47
<211> LENGTH: 8
<212> TYPE: PRT
<213> ORGANISM: Artificial Sequence
<220> FEATURE:
<223> OTHER INFORMATION: Melanocortin receptor ligand
```

```
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = penicillamine (Pen)
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: C-terminus is the free acid

<400> SEQUENCE: 47

Xaa Xaa Xaa His Xaa Arg Trp Cys
1               5

<210> SEQ ID NO 48
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (8)..(8)
<223> OTHER INFORMATION: Xaa = penicillamine (Pen)
<220> FEATURE:
<221> NAME/KEY: MOD_RES
<222> LOCATION: (8)..(8)
<223> OTHER INFORMATION: C-terminus is the free acid

<400> SEQUENCE: 48

Xaa Cys His Xaa Arg Trp Xaa Xaa
1               5

<210> SEQ ID NO 49
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
```

```
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-beta-(2-naphthyl)Ala (D-2-Nal)
<220> FEATURE:
<221> NAME/KEY: MOD_RES
<222> LOCATION: (8)..(8)
<223> OTHER INFORMATION: AMIDATION

<400> SEQUENCE: 49

Arg Cys Xaa His Xaa Arg Trp Cys
1               5

<210> SEQ ID NO 50
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Arg or D-Arg, both modified with acyl
      (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: AMIDATION

<400> SEQUENCE: 50

Xaa Cys Xaa His Xaa Arg Trp Cys
1               5

<210> SEQ ID NO 51
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = D-Arg or Arg, both modified with acyl
      (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
```

```
<222> LOCATION: (8)..(8)
<223> OTHER INFORMATION: Xaa = penicillamine (Pen)
<220> FEATURE:
<221> NAME/KEY: MOD_RES
<222> LOCATION: (8)..(8)
<223> OTHER INFORMATION: AMIDATION

<400> SEQUENCE: 51

Xaa Cys Xaa His Xaa Arg Trp Xaa
1               5

<210> SEQ ID NO 52
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = D-Arg or Arg, both modified with acyl
      (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MISC_FEATURE
<222> LOCATION: (8)..(8)
<223> OTHER INFORMATION: Xaa = penicillamine (Pen)
<220> FEATURE:
<221> NAME/KEY: MOD_RES
<222> LOCATION: (8)..(8)
<223> OTHER INFORMATION: AMIDATION

<400> SEQUENCE: 52

Xaa Cys His Xaa Arg Trp Xaa Xaa
1               5

<210> SEQ ID NO 53
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = D-Arg or Arg, both modified with acyl
      (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MOD_RES
<222> LOCATION: (8)..(8)
<223> OTHER INFORMATION: AMIDATION

<400> SEQUENCE: 53

Xaa Asp His Xaa Arg Trp Ala Lys
1               5
```

```
<210> SEQ ID NO 54
<211> LENGTH: 9
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(9)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = Gly, D-Ala, beta-Ala, 4-aminobutyric acid
      (Gaba) or 5-aminopentanoic acid (Apn)
<220> FEATURE:
<221> NAME/KEY: MOD_RES
<222> LOCATION: (9)..(9)
<223> OTHER INFORMATION: AMIDATION

<400> SEQUENCE: 54

Xaa Cys Xaa His Xaa Arg Trp Xaa Cys
1               5

<210> SEQ ID NO 55
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MOD_RES
<222> LOCATION: (1)..(1)
<223> OTHER INFORMATION: modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (6)..(6)
<223> OTHER INFORMATION: Xaa = Trp or beta-(2-naphthyl)alanine (2-Nal)
<220> FEATURE:
<221> NAME/KEY: MOD_RES
<222> LOCATION: (8)..(8)
<223> OTHER INFORMATION: AMIDATION

<400> SEQUENCE: 55

Cys Glu His Xaa Arg Xaa Ala Cys
1               5

<210> SEQ ID NO 56
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MOD_RES
```

```
<222> LOCATION: (1)..(1)
<223> OTHER INFORMATION: modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (2)..(2)
<223> OTHER INFORMATION: Xaa = D-Ala
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (6)..(6)
<223> OTHER INFORMATION: Xaa = Trp or beta-(2-naphthyl)Ala (2-Nal)
<220> FEATURE:
<221> NAME/KEY: MOD_RES
<222> LOCATION: (8)..(8)
<223> OTHER INFORMATION: AMIDATION

<400> SEQUENCE: 56

Cys Xaa His Xaa Arg Xaa Ala Cys
1               5

<210> SEQ ID NO 57
<211> LENGTH: 9
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(9)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (8)..(8)
<223> OTHER INFORMATION: Xaa = Ala, beta-Ala or 4-aminobutyric acid
      (Gaba)
<220> FEATURE:
<221> NAME/KEY: MOD_RES
<222> LOCATION: (9)..(9)
<223> OTHER INFORMATION: AMIDATION

<400> SEQUENCE: 57

Xaa Cys Xaa His Xaa Arg Trp Xaa Cys
1               5

<210> SEQ ID NO 58
<211> LENGTH: 9
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(9)
```

```
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Ala
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 3-benzothienylAla (Bal)
<220> FEATURE:
<221> NAME/KEY: MOD_RES
<222> LOCATION: (9)..(9)
<223> OTHER INFORMATION: AMIDATION

<400> SEQUENCE: 58

Xaa Asp Xaa His Xaa Arg Xaa Ala Lys
1               5

<210> SEQ ID NO 59
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = D-homo-cyclohexylAla (D-hCha) modified
      with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 59

Xaa Asp His Xaa Arg Trp Xaa Lys
1               5

<210> SEQ ID NO 60
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = beta-cyclohexylAla (Cha) modified with
      n-butyryl
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (4)..(4)
<223> OTHER INFORMATION: Xaa = D-Phe
<220> FEATURE:
<221> NAME/KEY: MISC_FEATURE
<222> LOCATION: (7)..(7)
```

```
<223> OTHER INFORMATION: Xaa = 4-aminobutyric acid (Gaba)
<220> FEATURE:
<221> NAME/KEY: MOD_RES
<222> LOCATION: (8)..(8)
<223> OTHER INFORMATION: AMIDATION

<400> SEQUENCE: 60

Xaa Asp His Xaa Arg Trp Xaa Lys
1               5

<210> SEQ ID NO 61
<211> LENGTH: 8
<212> TYPE: PRT
<213> ORGANISM: Artificial Sequence
<220> FEATURE:
<223> OTHER INFORMATION: Melanocortin receptor ligand
<220> FEATURE:
<221> NAME/KEY: MISC_FEATURE
<222> LOCATION: (1)..(1)
<223> OTHER INFORMATION: Xaa = Nle modified with acyl (Ac)
<220> FEATURE:
<221> NAME/KEY: DOMAIN
<222> LOCATION: (2)..(8)
<223> OTHER INFORMATION: Cyclic
<220> FEATURE:
<221> NAME/KEY: MISC_FEATURE
<222> LOCATION: (3)..(3)
<223> OTHER INFORMATION: Xaa = D-Glu
<220> FEATURE:
<221> NAME/KEY: MISC_FEATURE
<222> LOCATION: (5)..(5)
<223> OTHER INFORMATION: Xaa = D-Phe
<220> FEATURE:
<221> NAME/KEY: MOD_RES
<222> LOCATION: (8)..(8)
<223> OTHER INFORMATION: AMIDATION

<400> SEQUENCE: 61

Xaa Cys Xaa His Xaa Arg Trp Cys
1               5
```

MELANOCORTIN RECEPTOR LIGANDS

This application is a United States national stage filing under 35 U.S.C §371 of international (PCT) application No. PCT/US2006/026586, filed Jul. 10, 2006 and designating the US which claims priority to U.S. provisional applications 60/697/779, filed Jul. 8, 2005, and 60/748/850, filed Dec. 9, 2005.

BACKGROUND OF THE INVENTION

The present invention is directed to peptides which are ligands of one or more of the melanocortin receptors (MC-R), the pharmaceutically-acceptable salts thereof, to methods of using such peptides to treat mammals and to useful pharmaceutical compositions comprising said peptides.

Melanocortins are a family of regulatory peptides which are formed by post-translational processing of pro-hormone pro-opiomelanocortin (POMC; 131 amino acids in length). POMC is processed into three classes of hormones; the melanocortins, adrenocorticotropin hormone, and various endorphins (e.g. lipotropin) (Cone, et al., Recent Prog. Horm. Res., 51:287-317, (1996); Cone et al., Ann. N.Y. Acad. Sci., 31:342-363, (1993)).

Melanocortins have been found in a wide variety of normal human tissues including the brain, adrenal, skin, testis, spleen, kidney, ovary, lung, thyroid, liver, colon, small intestine and pancreas (Tatro, J. B. et al., Endocrinol. 121:1900-1907 (1987); Mountjoy, K. G. et al., Science 257:1248-1251 (1992); Chhajlani, V. et al., FEBS Lett. 309:417-420 (1992); Gantz, I. et al. J. Biol. Chem. 268:8246-8250 (1993) and Gantz, I. et al., J. Biol. Chem. 268:15174-15179 (1993)).

Melanocortin peptides have been shown to exhibit a wide variety of physiological activities including the control of behavior and memory, affecting neurotrophic and antipyretic properties, as well as affecting the modulation of the immune system. Aside from their well known effects on adrenal cortical functions (adrenocorticotropic hormone, ACTH) and on melanocytes (melanocyte stimulating hormone, MSH), melanocortins have also been shown to control the cardiovascular system, analgesia, thermoregulation and the release of other neurohumoral agents including prolactin, luteinizing hormone and biogenic amines (De Wied, D. et al., Methods Achiev. Exp. Pathol. 15:167-199 (1991); De Wied, D. et al., Physiol. Rev. 62:977-1059 (1982); Guber, K. A. et al., Am. J. Physiol. 257:R681-R694 (1989); Walker J. M. et al., Science 210:1247-1249 (1980); Murphy, M. T. et al., Science 221: 192-193 (1983); Ellerkmann, E. et al., Endocrinol. 130:133-138 (1992) and Versteeg, D. H. G. et al., Life Sci. 38:835-840 (1986)).

It has also been shown that binding sites for melanocortins are distributed in many different tissue types including lachrymal and submandibular glands, pancreas, adipose, bladder, duodenum, spleen, brain and gonadal tissues as well as malignant melanoma tumors. Five melanocortin receptors (MC-R) have been characterized to date. These include melanocyte-specific receptor (MC1-R), corticoadrenal-specific ACTH receptor (MC2-R), melacortin-3 (MC3-R), melanocortin-4 (MC4-R) and melanocortin-5 receptor (MC5-R). All of the melanocortin receptors respond to the peptide hormone class of melanocyte stimulating hormones (MSH) (Cone, R. D. et al., Ann. N.Y. Acad. Sci., 680:342-363 (1993); Cone, R. D. et al., Recent Prog. Horm. Res., 51:287-318 (1996)).

MC1-R, known in the art as Melanocyte Stimulating Hormone Receptor (MSH-R), Melanotropin Receptor or Melanocortin-1 Receptor, is a 315 amino acid transmembrane protein belonging to the family of G-Protein coupled receptors. MC1-R is a receptor for both MSH and ACTH. The activity of MC1-R is mediated by G-proteins which activate adenylate cyclase. MC1-R receptors are found in melanocytes and corticoadrenal tissue as well as various other tissues such as adrenal gland, leukocytes, lung, lymph node, ovary, testis, pituitary, placenta, spleen and uterus. MC2-R, also called Adrenocorticotropic hormone receptor (ACTH-R), is a 297 amino acid transmembrane protein found in melanocytes and the corticoadrenal tissue. MC2-R mediates the corticotrophic effect of ACTH. In humans, MC3-R is a 360 AA protein found in brain tissue; in mice and rats MC3-R is a 323 AA protein. MC4-R is a 332 amino acid transmembrane protein which is also expressed in brain as well as placental and gut tissues. MC5-R is a 325 amino acid transmembrane protein expressed in the adrenals, stomach, lung and spleen and very low levels in the brain. MC5-R is also expressed in the three layers of adrenal cortex, predominantly in the aldosterone-producing zona glomerulosa cells.

The five known melanocortin receptors differ, however, in their functions. For example, MC1-R is a G-protein coupled receptor that regulates pigmentation in response to α-MSH, a potent agonist of MC1-R. Agonism of the MC1-R receptor results in stimulation of the melanocytes which causes eumelanin and increases the risk for cancer of the skin. Agonism of MC1-R can also have neurological effects. Stimulation of MC2-R activity can result in carcinoma of adrenal tissue. Recent pharmacological confirmation has established that central MC4-R receptors are the prime mediators of the anorexic and orexigenic effects reported for melanocortin agonists and antagonists, respectively. The effects of agonism of the MC3-R and MC5-R are not yet known.

There has been great interest in melanocortin (MC-R) receptors as targets for the design of novel therapeutics to treat disorders of body weight such as obesity and cachexia. Both genetic and pharmacological evidence points toward central MC4-R receptors as the principal target (Giraudo, S. Q. et al., Brain Res., 809:302-306 (1998); Farooqi, I. S. et al., NE J. Med., 348:1085-1095 (2003); MacNeil, D. J. et al., Eu. J. Pharm., 44:141-157 (2002); MacNeil, D. J. et al., Eu. J. Pharm., 450:93-109 (2002); Kask, A. et al., NeuroReport, 10:707-711 (1999)). The current progress with receptor-selective agonists and antagonists evidences the therapeutic potential of melanocortin receptor activation, particularly MC4-R.

Agonist, antagonist or other ligand compounds activating one or more melanocortin receptor would be useful for treating a wide variety of indications in a subject in need thereof or at risk thereof including acute and chronic inflammatory diseases such as general inflammation (U.S. Pat. No. 6,613,874; Catania, A. et al., Pharm. Rev., 56:1-29 (2004)), inflammatory bowel disease (U.S. Pat. No. 6,713,487; Catania, A. et al., Pharm. Rev., 56:1-29 (2004)), brain inflammation (Catania, A. et al., Pharm. Rev., 56:1-29 (2004)), sepsis (U.S. Pat. No. 6,613,874; U.S. Pat. No. 6,713,487; Catania, A. et al., Pharm. Rev., 56:1-29 (2004)) and septic shock (U.S. Pat. No. 6,613, 874; Catania, A. et al., Pharm. Rev., 56:1-29 (2004)); diseases with an autoimmune component such as rheumatoid arthritis (U.S. Pat. No. 6,713,487; Catania, A. et al., Pharm. Rev., 56:1-29 (2004)), gouty arthritis (Catania, A. et al., Pharm. Rev., 56:1-29 (2004), Getting, S. J. et al., Curr. Opin. Investig. Drugs, 2:1064-1069 (2001)), and multiple sclerosis ((U.S. Pat. No. 6,713,487); metabolic diseases and medical conditions accompanied by weight gain such as obesity (U.S. Pat. Nos. 6,613,874; 6,600,015; Fehm, H. L. et al., J. Clin. Endo. & Metab., 86:1144-1148 (2001); Hansen, M. J. et al., Brain Res., 1039:137-145 (2005); Ye, Z. et al., Peptides, 26:2017-2025 (2005); Farooqi, I. S. et al., NE J. Med., 348:1085-1095

(2003); MacNeil, D. J. et al., Eu. J. Pharm., 44:141-157 (2002); MacNeil, D. J. et al., Eu. J. Pharm., 450:93-109 (2002); Kask, A. et al., NeuroReport, 10:707-711 (1999); Schwartz, M. W., J. Clin. Invest., 108:963-964 (2001), Gura, T., Science, 287:1738-1740 (2000), Raffin-Sanson, M. L., Eu. J. Endo., 144:207-208 (2001), Hamilton, B. S. et al., Obesity Res. 10:182-187 (2002)), feeding disorders (U.S. Pat. No. 6,720,324; Fehm, H. L. et al., J. Clin. Endo. & Metab., 86:1144-1148 (2001); Pontillo, J. et al., Bioorganic & Med. Chem. Ltrs., 15:2541-2546 (2005)) and Prader-Willi Syndrome (GE, Y. et al., Brain Research, 957:42-45 (2002)); metabolic diseases and medical conditions accompanied by weight loss such as anorexia (U.S. Pat. No. 6,613,874; Wisse, B. R. et al., Endo., 142:3292-3301 (2001)), bulimia (U.S. Pat. No. 6,720,324), AIDS wasting (Marsilje, T. H. et al., Bioorg. Med. Chem. Lett., 14:3721-3725 (2004); Markison, S. et al., Endocrinology, 146:2766-2773 (2005)), cachexia (U.S. Pat. No. 6,613,874; Lechan, R. M. et al., Endo., 142:3288-3291 (2001); Pontillo, J. et al., Bioorganic & Med. Chem. Ltrs., 15:2541-2546 (2005)), cancer cachexia (U.S. Pat. No. 6,639, 123) and wasting in frail elderly (U.S. Pat. No. 6,639,123); diabetes (U.S. Pat. No. 6,713,487) and diabetalogical related conditions and complications of diabetes such as retinopathy (U.S. Pat. No. 6,525,019); neoplastic proliferation (U.S. Pat. No. 6,713,487) such as skin cancer (Sturm, R. A., Melanoma Res., 12:405-416 (2002); Bastiens, M. T. et al., Am. J. Hum. Genet., 68:884-894 (2001)), and prostate cancer (Luscombe, C. J. et al., British J. Cancer, 85:1504-1509 (2001); reproductive or sexual medical conditions such as endometriosis (U.S. Pat. No. 6,713,487) and uterine bleeding in women (U.S. Pat. No. 6,613,874), sexual dysfunction (U.S. Pat. No. 6,720,324; Van der Ploeg, L. H. T. et al., PNAS, 99:11381-11386 (2002), Molinoff, P. B. et al., Ann. N.Y. Acad. Sci., 994:96-102 (2003), Hopps, C. V. et al., BJU International, 92:534-538 (2003)), erectile dysfunction ((U.S. Pat. No. 6,613,874; Diamond, L. E. et al., Urology, 65:755-759 (2005), Wessells, H. et al., Int. J. Impotence Res., 12:S74-S79 (2000), Andersson, K-E. et al., Int. J. Impotence Res., 14:S82-S92 (2002), Bertolini, A. et. al., Sexual Behavior: Pharmacology and Biochemistry, Raven Press, NY, p 247-257 (1975); Wessells, H. et al., Neuroscience, 118:755-762 (2003), Wessells, H. et al., Urology, 56:641-646 (2000), Shadiack, A. M. et al., Society for Neuroscience Abstract, (2003); Wessells, H. et al., J. Urology, 160:389-393 (1998), Rosen, R. C. et al., Int. J. Impotence Res., 16:135-142 (2004), Wessells, H. et al., Peptides, 26:1972-1977 (2005)) and decreased sexual response in females (U.S. Pat. No. 6,713,487; Fourcroy, J. L., Drugs, 63:1445-1457 (2003)); diseases or conditions resulting from treatment or insult to the organism such as organ transplant rejection (U.S. Pat. No. 6,713,487; Catania, A. et al., Pharm. Rev., 56:1-29 (2004)), ischemia and reperfusion injury (Mioni, C. et al., Eu. J. Pharm., 477:227-234 (2003); Catania, A. et al., Pharm. Rev., 56:1-29 (2004)), treatment of spinal cord injury and to accelerate wound healing (Sharma H. S. et al., Acta. Nerochir. Suppl., 86:399-405 (2003); Sharma H. S., Ann. N.Y. Acad. Sci. 1053: 407-421 (2005); U.S. Pat. No. 6,525,019), as well as weight loss caused by chemotherapy, radiation therapy, temporary or permanent immobilization (Harris, R. B. et al., Physiol. Behav., 73:599-608 (2001)) or dialysis; cardiovascular diseases or conditions such as hemorrhagic shock (Catania, A. et al., Pharm. Rev., 56:1-29 (2004)), cardiogenic shock (U.S. Pat. No. 6,613,874), hypovolemic shock (U.S. Pat. No. 6,613,874), cardiovascular disorders (U.S. Pat. No. 6,613,874) and cardiac cachexia (Markison, S. et al., Endocrinology, 146:2766-2773 (2005); pulmonary diseases or conditions such as acute respiratory distress syndrome (U.S. Pat. No. 6,350,430; Catania, A. et al., Pharm. Rev., 56:1-29 (2004)), chronic obstructive pulmonary disease (U.S. Pat. No. 6,713,487), asthma (U.S. Pat. No. 6,713,487) and pulmonary fibrosis; to enhance immune tolerance (Luger, T. A. et al., Pathobiology, 67:318-321 (1999)) and to combat assaults to the immune system such as those associated with certain allergies (U.S. Pat. No. 6,713,487) or organ transplant rejection (U.S. Pat. No. 6,713,487; Catania, A. et al., Pharm. Rev., 56:1-29 (2004)); treatment of dermatological diseases and conditions such as psoriasis (U.S. Pat. No. 6,713,487), skin pigmentation depletion (U.S. Pat. No. 6,713,487; Ye, Z. et al., Peptides, 26:2017-2025 (2005)), acne (Hatta, N. et al., J. Invest. Dermatol., 116:564-570 (2001); Bohm, M. et al., J. Invest. Dermatol., 118:533-539 (2002)), keloid formation (U.S. Pat. No. 6,525,019) and skin cancer (Sturm, R. A., Melanoma Res., 12:405-416 (2002); Bastiens, M. T. et al., Am. J. Hum. Genet., 68:884-894 (2001)); behavioral, central nervous system or neuronal conditions and disorders such as anxiety (U.S. Pat. No. 6,720,324; Pontillo, J. et al., Bioorganic & Med. Chem. Ltrs., 15:2541-2546 (2005)), depression (Chaki, S. et al., Peptides, 26:1952-1964 (2005), Bednarek, M. A. et al., Expert Opinion Ther. Patents, 14:327-336 (2004); U.S. Pat. No. 6,720,324), memory and memory dysfunction (U.S. Pat. No. 6,613,874; Voisey, J. et al., Curr. Drug Targets, 4:586-597 (2003)), modulating pain perception (U.S. Pat. No. 6,613,874; Bertolini, A. et al., J. Endocrinol. Invest., 4:241-251 (1981); Vrinten, D. et al., J. Neuroscience, 20:8131-8137 (2000)) and treating neuropathic pain (Pontillo, J. et al., Bioorganic & Med. Chem. Ltrs., 15:2541-2546 (2005)); conditions and diseases associated with alcohol consumption, alcohol abuse and/or alcoholism (WO 05/060985; Navarro, M. et al., Alcohol Clin. Exp. Res., 29:949-957 (2005)); and renal conditions or diseases such as the treatment of renal cachexia (Markison, S. et al., Endocrinology, 146:2766-2773 (2005)) or natriuresis (U.S. Pat. No. 6,613, 874).

Ligand compounds activating one or more melanocortin receptor would be useful for modulating a wide variety of normalizing or homeostatic activities in a subject in need thereof including thyroxin release (U.S. Pat. No. 6,613,874), aldosterone synthesis and release (U.S. Pat. No. 6,613,874), body temperature (U.S. Pat. No. 6,613,874), blood pressure (U.S. Pat. No. 6,613,874), heart rate (U.S. Pat. No. 6,613, 874), vascular tone (U.S. Pat. No. 6,613,874), brain blood flow (U.S. Pat. No. 6,613,874), blood glucose levels (U.S. Pat. No. 6,613,874), bone metabolism, bone formation or development (Dumont, L. M. et al., Peptides, 26:1929-1935 (2005), ovarian weight (U.S. Pat. No. 6,613,874), placental development (U.S. Pat. No. 6,613,874), prolactin and FSH secretion (U.S. Pat. No. 6,613,874), intrauterine fetal growth (U.S. Pat. No. 6,613,874), parturition (U.S. Pat. No. 6,613, 874), spermatogenesis (U.S. Pat. No. 6,613,874), sebum and pheromone secretion (U.S. Pat. No. 6,613,874), neuroprotection (U.S. Pat. No. 6,639,123) and nerve growth (U.S. Pat. No. 6,613,874) as well as modulating motivation (U.S. Pat. No. 6,613,874), learning (U.S. Pat. No. 6,613,874) and other behaviors (U.S. Pat. No. 6,613,874).

It is, therefore, an objective of the present invention to provide ligands for the melanocortin receptors which exhibit greater stability and selectivity for melanocortin receptors than native melanocortin receptor ligands.

SUMMARY OF THE INVENTION

In one aspect, the present invention is directed to a compound according formula (I):

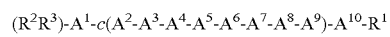

$(R^2R^3)\text{-}A^1\text{-}c(A^2\text{-}A^3\text{-}A^4\text{-}A^5\text{-}A^6\text{-}A^7\text{-}A^8\text{-}A^9)\text{-}A^{10}\text{-}R^1$ wherein:

$A^1$ is Acc, HN—$(CH_2)_m$—C(O), L- or D-amino acid, or deleted;

$A^2$ is Cys, D-Cys, hCys, D-hCys, Pen, D-Pen, Asp, or Glu;

$A^3$ is Gly, Ala, β-Ala, Gaba, Aib, D-amino acid, or deleted;

$A^4$ is His, 2-Pal, 3-Pal, 4-Pal, Taz, 2-Thi, 3-Thi, or $(X^1,X^2,X^3,X^4,X^5)$Phe;

$A^5$ is D-Phe, D-1-Nal, D-2-Nal, D-Trp, D-Bal, D-$(X^1,X^2,X^3,X^4,X^5)$Phe, L-Phe or D-(Et)Tyr;

$A^6$ is Arg, hArg, Dab, Dap, Lys, Orn, or HN—CH$(CH_2)_n$—N($R^4R^5$))—C(O);

$A^7$ is Trp, 1-Nal, 2-Nal, Bal, Bip, D-Trp, D-1-Nal, D-2-Nal, D-Bal or D-Bip;

$A^8$ is Gly, D-Ala, Acc, Ala, β-Ala, Gaba, Apn, Ahx, Aha, HN—$(CH_2)_s$—C(O), or deleted;

$A^9$ is Cys, D-Cys, hCys, D-hCys, Pen, D-Pen, Dab; Dap, Orn, or Lys;

$A^{10}$ is Acc, HN—$(CH_2)_t$—C(O), L- or D-amino acid, or deleted;

$R^1$ is —OH, or —$NH_2$;

each of $R^2$ and $R^3$ is independently for each occurrence selected from the group consisting of H, $(C_1-C_{30})$alkyl, $(C_1-C_{30})$heteroalkyl, $(C_1-C_{30})$acyl, $(C_2-C_{30})$alkenyl, $(C_2-C_{30})$alkynyl, aryl$(C_1-C_{30})$alkyl, aryl$(C_1-C_{30})$acyl, substituted $(C_1-C_{30})$alkyl, substituted $(C_1-C_{30})$heteroalkyl, substituted $(C_1-C_{30})$acyl, substituted $(C_2-C_{30})$alkenyl, substituted $(C_2-C_{30})$alkynyl, substituted aryl$(C_1-C_{30})$alkyl, and substituted aryl$(C_1-C_{30})$acyl;

$R^4$ and $R^5$ each is, independently for each occurrence, H, $(C_1-C_{40})$alkyl, $(C_1-C_{40})$heteroalkyl, $(C_1-C_{40})$acyl, $(C_2-C_{40})$alkenyl, $(C_2-C_{40})$alkynyl, aryl$(C_1-C_{40})$alkyl, aryl$(C_1-C_{40})$acyl, substituted $(C_1-C_{40})$alkyl, substituted $(C_1-C_{40})$heteroalkyl, substituted $(C_1-C_{40})$acyl, substituted $(C_2-C_{40})$alkenyl, substituted $(C_2-C_{40})$alkynyl, substituted aryl$(C_1-C_{40})$alkyl, substituted aryl$(C_1-C_{40})$acyl, $(C_1-C_{40})$alkylsulfonyl, or —C(NH)—$NH_2$;

m is, independently for each occurrence, 1, 2, 3, 4, 5, 6 or 7;

n is, independently for each occurrence, 1, 2, 3, 4 or 5;

s is, independently for each occurrence, 1, 2, 3, 4, 5, 6, or 7;

t is, independently for each occurrence, 1, 2, 3, 4, 5, 6, or 7;

$X^1$, $X^2$, $X^3$, $X^4$, and $X^5$ each is, independently for each occurrence, H, F, Cl, Br, I, $(C_{1-10})$alkyl, substituted $(C_{1-10})$alkyl, $(C_{2-10})$alkenyl, substituted $(C_{2-10})$alkenyl, $(C_{2-10})$alkynyl, substituted $(C_{2-10})$alkynyl, aryl, substituted aryl, OH, $NH_2$, $NO_2$, or CN;

provided that (I). when $R^4$ is $(C_1-C_{40})$acyl, aryl$(C_1-C_{40})$acyl, substituted $(C_1-C_{40})$acyl, substituted aryl$(C_1-C_{40})$acyl, $(C_1-C_{40})$alkylsulfonyl, or —C(NH)—$NH_2$, then $R^5$ is H or $(C_1-C_{40})$alkyl, $(C_1-C_{40})$heteroalkyl, $(C_2-C_{40})$alkenyl, $(C_2-C_{40})$alkynyl, aryl$(C_1-C_{40})$alkyl, substituted $(C_1-C_{40})$alkyl, substituted $(C_1-C_{40})$heteroalkyl, substituted $(C_2-C_{40})$alkenyl, substituted $(C_2-C_{40})$alkynyl, or substituted aryl$(C_1-C_{40})$alkyl;

(II). when $R^2$ is $(C_1-C_{30})$acyl, aryl$(C_1-C_{30})$acyl, substituted $(C_1-C_{30})$acyl, or substituted aryl$(C_1-C_{30})$acyl, then $R^3$ is H, $(C_1-C_{30})$alkyl, $(C_1-C_{30})$heteroalkyl, $(C_2-C_{30})$alkenyl, $(C_2-C_{30})$alkynyl, aryl$(C_1-C_{30})$alkyl, substituted $(C_1-C_{30})$alkyl, substituted $(C_2-C_{30})$heteroalkyl, substituted $(C_2-C_{30})$alkenyl, substituted $(C_2-C_{30})$alkynyl, or substituted aryl$(C_1-C_{30})$alkyl;

(III). either $A^3$ or $A^8$ or both must be present in said compound;

(IV). when $A^2$ is Cys, D-Cys, hCys, D-hCys, Pen, or D-Pen, then $A^9$ is Cys, D-Cys, hCys, D-hCys, Pen, or D-Pen;

(V). when $A^2$ is Asp or Glu, then $A^9$ is Dab, Dap, Orn, or Lys;

(VI). when $A^8$ is Ala or Gly, then $A^1$ is not Nle; and (VII). when $A^1$ is deleted, then $R^2$ and $R^3$ cannot both be H;

or a pharmaceutically acceptable salt thereof.

A preferred group of compounds of the immediate foregoing formula, is where $A^1$ is A6c, Gaba, Nle, Met, Phe, D-Phe, D-2-Nal, hPhe, Chg, D-Chg, Cha, hCha, hPro, hLeu, Nip, β-hMet, or Oic;

$A^2$ is Cys, D-Cys, hCys, D-hCys, Pen, D-Pen, Asp, or Glu;

$A^3$ is Gly, Ala, D-Ala, D-Glu, β-Ala, Gaba, Aib, or deleted;

$A^4$ is His;

$A^5$ is D-Phe, D-1-Nal, D-2-Nal, D-Trp, D-Bal, or D-(Et)Tyr;

$A^6$ is Arg, or hArg;

$A^7$ is Trp, Bip, D-Trp, 1-Nal, or 2-Nal;

$A^8$ is A6c, Ala, β-Ala, Gaba, Apn, or Ahx;

$A^9$ is Cys, D-Cys, hCys, D-hCys, Pen, D-Pen, or Lys;

$A^{10}$ is Thr, or deleted or a pharmaceutically acceptable salt thereof.

A preferred group of compounds of the immediately foregoing group of compounds is where $R^2$ and $R^3$ each is, independently, H, acyl, n-propanoyl, or n-butanoyl or a pharmaceutically acceptable salt thereof.

A more preferred compound of formula (I) is where said compound is of the formula:

$A^1$ is Acc, Arg, D-Arg, Cha, D-Cha, hCha, Chg, D-Chg, Gaba, Ile, Leu, hLeu, β-hMet, 2-Nal, D-2-Nal, Nip, Nle, Oic, Phe, D-Phe, hPhe, hPro, Val or deleted;

$A^2$ is Cys, D-Cys, Pen or Asp;

$A^3$ is Gly, Ala, β-Ala, Gaba, Aib, D-Ala, D-Abu, D-Cha, D-Ile, D-Leu, D-Tle, D-Val or deleted;

$A^4$ is His or 3-Pal;

$A^5$ is D-Phe, D-2-Nal or D-(Et)Tyr;

$A^6$ is Arg or hArg;

$A^7$ is Trp, 1-Nal, 2-Nal, Bal, Bip or D-Trp;

$A^8$ is Gly, D-Ala, Acc, Ala, β-Ala, Gaba, Apn, Ahx, Aha or deleted;

$A^9$ is Cys, D-Cys, Pen or Lys;

$A^{10}$ is Thr or deleted;

wherein at least one of $A^3$ or $A^8$ is deleted, but not both, or a pharmaceutically acceptable salt thereof.

More preferred compounds of the immediately foregoing group of compounds is where said compound is of the formula:

```
                                                SEQ ID NO: 1
Ac-Nle-c(Asp-His-D-Phe-Arg-Trp-β-Ala-Lys)-NH2;

SEQ ID NO: 1
Ac-Nle-c(Asp-His-D-Phe-Arg-Trp-A6c-Lys)-NH2;

SEQ ID NO: 2
Ac-Nle-c(Cys-His-D-Phe-Arg-Trp-Ahx-Cys)-NH2;

SEQ ID NO: 3
D-Phe-c(Cys-His-D-Phe-Arg-Trp-Ala-D-Cys)-Thr-NH2;
```

D-Phe-c(Cys-His-D-Phe-Arg-Trp-β-Ala-D-Cys)-Thr-NH₂;   SEQ ID NO: 3

D-Phe-c(Cys-His-D-Phe-Arg-Trp-Gaba-D-Cys)-Thr-NH₂;   SEQ ID NO: 3

Ac-Nle-c(Cys-His-D-Phe-Arg-Trp-Apn-Cys)-NH₂;   SEQ ID NO: 2

Ac-Nle-c(Asp-His-D-Phe-Arg-Trp-Apn-Lys)-NH₂;   SEQ ID NO: 4

Ac-A6c-c(Asp-His-D-Phe-Arg-Trp-Gaba-Lys)-NH₂;   SEQ ID NO: 5

Ac-D-2-Nal-c(Asp-His-D-Phe-Arg-Trp-Gaba-Lys)-NH₂;   SEQ ID NO: 6

Ac-Cha-c(Asp-His-D-Phe-Arg-Trp-Gaba-Lys)-NH₂;   SEQ ID NO: 6

Ac-Nle-c(Asp-His-D-Phe-Arg-Trp-Gaba-Lys)-NH₂;   SEQ ID NO: 6

Ac-Nle-c(Cys-D-Ala-His-D-Phe-Arg-Trp-Cys)-NH₂;   SEQ ID NO: 7

Ac-Nle-c(Cys-β-Ala-His-D-Phe-Arg-Trp-Cys)-NH₂;   SEQ ID NO: 7

Ac-Nle-c(Cys-Gaba-His-D-Phe-Arg-Trp-Cys)-NH₂;   SEQ ID NO: 7

Ac-Nle-c(Cys-Aib-His-D-Phe-Arg-Trp-Cys)-NH₂;   SEQ ID NO: 7

Ac-Nle-c(Cys-Gly-His-D-Phe-Arg-Trp-Cys)-NH₂;   SEQ ID NO: 7

Ac-Nle-c(D-Cys-Ala-His-D-Phe-Arg-Trp-Cys)-NH₂;   SEQ ID NO: 8

Ac-Nle-c(D-Cys-D-Ala-His-D-Phe-Arg-Trp-Cys)-NH₂;   SEQ ID NO: 8

Ac-Nle-c(D-Cys-β-Ala-His-D-Phe-Arg-Trp-Cys)-NH₂;   SEQ ID NO: 8

Ac-Nle-c(D-Cys-Gaba-His-D-Phe-Arg-Trp-Cys)-NH₂;   SEQ ID NO: 8

Ac-Nle-c(D-Cys-Aib-His-D-Phe-Arg-Trp-Cys)-NH₂;   SEQ ID NO: 8

Ac-Nle-c(D-Cys-Gly-His-D-Phe-Arg-Trp-Cys)-NH₂;   SEQ ID NO: 8

Ac-Nle-c(Cys-D-Ala-His-D-Phe-Arg-Trp-D-Cys)-NH₂;   SEQ ID NO: 9

Ac-Nle-c(Cys-β-Ala-His-D-Phe-Arg-Trp-D-Cys)-NH₂;   SEQ ID NO: 9

Ac-Nle-c(Cys-Gaba-His-D-Phe-Arg-Trp-D-Cys)-NH₂;   SEQ ID NO: 9

Ac-Nle-c(Cys-Aib-His-D-Phe-Arg-Trp-D-Cys)-NH₂;   SEQ ID NO: 9

Ac-Nle-c(Cys-Gly-His-D-Phe-Arg-Trp-D-Cys)-NH₂;   SEQ ID NO: 9

Ac-Nle-c(D-Cys-Ala-His-D-Phe-Arg-Trp-D-Cys)-NH₂;   SEQ ID NO: 10

Ac-Nle-c(D-Cys-D-Ala-His-D-Phe-Arg-Trp-D-Cys)-NH₂;   SEQ ID NO: 10

Ac-Nle-c(D-Cys-β-Ala-His-D-Phe-Arg-Trp-D-Cys)-NH₂;   SEQ ID NO: 10

```
                                                     SEQ ID NO: 10
Ac-Nle-c(D-Cys-Gaba-His-D-Phe-Arg-Trp-D-Cys)-NH2;

SEQ ID NO: 10
Ac-Nle-c(D-Cys-Aib-His-D-Phe-Arg-Trp-D-Cys)-NH2;

SEQ ID NO: 11
Ac-Oic-c(Asp-His-D-Phe-Arg-Trp-Gaba-Lys)-NH2;

SEQ ID NO: 11
Ac-Chg-c(Asp-His-D-Phe-Arg-Trp-Gaba-Lys)-NH2;

SEQ ID NO: 11
Ac-hCha-c(Asp-His-D-Phe-Arg-Trp-Gaba-Lys)-NH2;

SEQ ID NO: 11
Ac-D-Cha-c(Asp-His-D-Phe-Arg-Trp-Gaba-Lys)-NH2;

SEQ ID NO: 11
Ac-Nip-c(Asp-His-D-Phe-Arg-Trp-Gaba-Lys)-NH2;

SEQ ID NO: 11
Ac-hPro-c(Asp-His-D-Phe-Arg-Trp-Gaba-Lys)-NH2;

SEQ ID NO: 11
Ac-hLeu-c(Asp-His-D-Phe-Arg-Trp-Gaba-Lys)-NH2;

SEQ ID NO: 11
Ac-hCha-c(Asp-His-D-Phe-Arg-Trp-Gaba-Lys)-NH2;

SEQ ID NO: 11
Ac-Phe-c(Asp-His-D-Phe-Arg-Trp-Gaba-Lys)-NH2;

SEQ ID NO: 11
Ac-D-Phe-c(Asp-His-D-Phe-Arg-Trp-Gaba-Lys)-NH2;

SEQ ID NO: 11
Ac-D-Chg-c(Asp-His-D-Phe-Arg-Trp-Gaba-Lys)-NH2;

SEQ ID NO: 12
n-butanoyl-Cha-c(Asp-His-D-Phe-Arg-Trp-Gaba-Lys)-NH2;

SEQ ID NO: 11
Ac-hPhe-c(Asp-His-D-Phe-Arg-Trp-Gaba-Lys)-NH2;

SEQ ID NO: 11
Ac-β-hMet-c(Asp-His-D-Phe-Arg-Trp-Gaba-Lys)-NH2;

SEQ ID NO: 11
Ac-Gaba-c(Asp-His-D-Phe-Arg-Trp-Gaba-Lys)-NH2;

SEQ ID NO: 13
Ac-Cha-c(Asp-His-D-Phe-Arg-D-Trp-Ala-Lys)-NH2;

SEQ ID NO: 13
Ac-hCha-c(Asp-His-D-Phe-Arg-D-Trp-Ala-Lys)-NH2;

SEQ ID NO: 13
Ac-Leu-c(Asp-His-D-Phe-Arg-D-Trp-Ala-Lys)-NH2;

SEQ ID NO: 13
Ac-hLeu-c(Asp-His-D-Phe-Arg-D-Trp-Ala-Lys)-NH2;

SEQ ID NO: 13
Ac-Phe-c(Asp-His-D-Phe-Arg-D-Trp-Ala-Lys)-NH2;

SEQ ID NO: 14
Ac-Nle-c(Asp-His-D-Phe-Arg-D-Trp-D-Ala-Lys)-NH2;

SEQ ID NO: 14
Ac-Nle-c(Asp-His-D-Phe-Arg-D-Trp-β-Ala-Lys)-NH2;

SEQ ID NO: 14
Ac-Nle-c(Asp-His-D-Phe-Arg-D-Trp-Gaba-Lys)-NH2;

SEQ ID NO: 14
Ac-Nle-c(Asp-His-D-Phe-Arg-D-Trp-Aha-Lys)-NH2;

SEQ ID NO: 14
Ac-Nle-c(Asp-His-D-Phe-Arg-D-Trp-Apn-Lys)-NH2;
```

-continued

```
                                              SEQ ID NO: 15
Ac-Nle-c(Cys-His-D-Phe-Arg-D-Trp-Apn-Cys)-NH₂;

SEQ ID NO: 15
Ac-Nle-c(Cys-His-D-Phe-Arg-D-Trp-Gaba-Cys)-NH₂;

SEQ ID NO: 15
Ac-Nle-c(Cys-His-D-Phe-Arg-D-Trp-Ahx-Cys)-NH₂;

SEQ ID NO: 15
Ac-Nle-c(Cys-His-D-Phe-Arg-D-Trp-β-Ala-Cys)-NH₂;

SEQ ID NO: 15
Ac-Nle-c(Cys-His-D-Phe-Arg-D-Trp-D-Ala-Cys)-NH₂;

SEQ ID NO: 16
Ac-Nle-c(Cys-D-Ala-His-D-2-Nal-Arg-Trp-Cys)-NH₂;

SEQ ID NO: 16
Ac-Nle-c(Cys-D-Ala-His-D-2-Nal-Arg-2-Nal-Cys)-NH₂;

SEQ ID NO: 16
Ac-Nle-c(Cys-D-Ala-His-D-2-Nal-Arg-1-Nal-Cys)-NH₂;

SEQ ID NO: 17
n-butanoyl-Nle-c(Cys-D-Ala-His-D-Phe-Arg-2-Nal-Cys)-NH₂;

SEQ ID NO: 17
n-butanoyl-Nle-c(Cys-D-Ala-His-D-Phe-Arg-Trp-Cys)-NH₂;

SEQ ID NO: 18
Ac-Nle-c(Cys-D-Ala-His-D-Phe-Arg-2-Nal-Cys)-NH₂;

SEQ ID NO: 18
Ac-Nle-c(Cys-D-Ala-His-D-Phe-Arg-1-Nal-Cys)-NH₂;

SEQ ID NO: 18
Ac-Nle-c(Cys-D-Ala-His-D-Phe-Arg-Bal-Cys)-NH₂;

SEQ ID NO: 61
Ac-Nle-c(Cys-D-Glu-His-D-Phe-Arg-Trp-Cys)-NH₂;

SEQ ID NO: 19
Ac-Nle-c(Asp-His-D-Phe-Arg-Trp-D-Ala-Lys)-NH₂;

SEQ ID NO: 20
Ac-Nle-c(Cys-D-Ala-His-D-2-Nal-Arg-Bal-Cys)-NH₂;

SEQ ID NO: 21
Ac-Nle-c(Pen-D-Ala-His-D-Phe-Arg-Trp-Cys)-NH₂;

SEQ ID NO: 22
Ac-Nle-c(Cys-D-Ala-His-D-Phe-Arg-Trp-Pen)-NH₂;

SEQ ID NO: 22
Ac-Nle-c(Pen-D-Ala-His-D-Phe-Arg-Trp-Pen)-NH₂;

SEQ ID NO: 23
D-Phe-c(Cys-His-D-Phe-hArg-Trp-β-Ala-D-Cys)-Thr-NH₂;

SEQ ID NO: 24
D-Phe-c(Cys-His-D-(Et)Tyr-Arg-Trp-β-Ala-D-Cys)-Thr-NH₂;

SEQ ID NO: 25
D-Phe-c(Cys-His-D-Phe-Arg-Bip-β-Ala-D-Cys)-Thr-NH₂;

SEQ ID NO: 24
D-Phe-c(Cys-His-D-(Et)Tyr-hArg-Trp-β-Ala-D-Cys)-Thr-NH₂;

SEQ ID NO: 26
D-Phe-c(Cys-His-D-Phe-hArg-Bip-β-Ala-D-Cys)-Thr-NH₂;

SEQ ID NO: 26
D-Phe-c(Cys-His-D-(Et)Tyr-hArg-Bip-β-Ala-D-Cys)-Thr-NH₂;

SEQ ID NO: 27
Nle-c(Cys-His-D-Phe-Arg-Trp-Apn-Cys)-NH₂;

SEQ ID NO: 28
Ac-Nle-c(Asp-D-Ala-His-D-Phe-Arg-Trp-Lys)-NH₂;
```

-continued

```
Ac-Nle-c(Asp-D-Ala-His-D-Phe-Arg-Bal-Lys)-NH2;        SEQ ID NO: 28

Ac-Nle-c(Cys-D-Ala-His-D-Phe-Arg-Trp-Pen)-OH;         SEQ ID NO: 29

Ac-Nle-c(Cys-D-Abu-His-D-Phe-Arg-Trp-Cys)-NH2;        SEQ ID NO: 30

Ac-Nle-c(Cys-D-Val-His-D-Phe-Arg-Trp-Cys)-NH2;        SEQ ID NO: 30

Ac-Nle-c(Cys-D-Ile-His-D-Phe-Arg-Trp-Cys)-NH2;        SEQ ID NO: 30

Ac-Nle-c(Cys-D-Leu-His-D-Phe-Arg-Trp-Cys)-NH2;        SEQ ID NO: 30

Ac-Nle-c(Cys-D-Tle-His-D-Phe-Arg-Trp-Cys)-NH2;        SEQ ID NO: 30

Ac-Nle-c(Cys-D-Cha-His-D-Phe-Arg-Trp-Cys)-NH2;        SEQ ID NO: 30

Ac-Nle-c(Pen-His-D-Phe-Arg-Trp-Gaba-Cys)-NH2;         SEQ ID NO: 31

Ac-Nle-c(Cys-His-D-Phe-Arg-Trp-Gaba-Pen)-NH2;         SEQ ID NO: 32

Ac-Nle-c(Pen-His-D-Phe-Arg-Trp-Gaba-Pen)-NH2;         SEQ ID NO: 32

Ac-Leu-c(Cys-His-D-Phe-Arg-Trp-Gaba-Cys)-NH2;         SEQ ID NO: 33

Ac-Cha-c(Cys-His-D-Phe-Arg-Trp-Gaba-Cys)-NH2;         SEQ ID NO: 33

Ac-Ile-c(Cys-His-D-Phe-Arg-Trp-Gaba-Cys)-NH2;         SEQ ID NO: 33

Ac-Phe-c(Cys-His-D-Phe-Arg-Trp-Gaba-Cys)-NH2;         SEQ ID NO: 33

Ac-Val-c(Cys-His-D-Phe-Arg-Trp-Gaba-Cys)-NH2;         SEQ ID NO: 33

Ac-2-Nal-c(Cys-His-D-Phe-Arg-Trp-Gaba-Cys)-NH2;       SEQ ID NO: 33

Nle-c(Cys-His-D-Phe-Arg-Trp-Gaba-Cys)-NH2;            SEQ ID NO: 34

Phe-c(Cys-His-D-Phe-Arg-Trp-Gaba-Cys)-NH2;            SEQ ID NO: 34

Ac-Nle-c(Cys-3-Pal-D-Phe-Arg-Trp-Gaba-Cys)-NH2;       SEQ ID NO: 35

Ac-Nle-c(Cys-D-Ala-His-D-Phe-Arg-Trp-Cys)-OH;         SEQ ID NO: 36

Ac-Nle-c(Cys-His-Phe-Arg-D-Trp-Gaba-Cys)-NH2;         SEQ ID NO: 37

Ac-Nle-c(Asp-His-D-2-Nal-Arg-Trp-Ala-Lys)-NH2;        SEQ ID NO: 38

Ac-Nle-c(Asp-His-D-2-Nal-Arg-Trp-β-Ala-Lys)-NH2;      SEQ ID NO: 38

Ac-Nle-c(Cys-His-D-2-Nal-Arg-Trp-Gaba-Cys)-NH2;       SEQ ID NO: 39

Ac-Nle-c(Cys-His-D-2-Nal-Arg-Trp-Ahx-Cys)-NH2;        SEQ ID NO: 39

Ac-hPhe-c(Asp-His-D-2-Nal-Arg-Trp-Gaba-Lys)-NH2;      SEQ ID NO: 40
```

```
                                                       SEQ ID NO: 40
Ac-Cha-c(Asp-His-D-2-Nal-Arg-Trp-Gaba-Lys)-NH2;

SEQ ID NO: 41
Ac-Nle-c(Asp-His-D-Phe-Arg-Trp-β-Ala-Lys)-OH;

SEQ ID NO: 42
Ac-Nle-c(Cys-His-D-Phe-Arg-Trp-Ahx-Cys)-OH;

SEQ ID NO: 43
D-Phe-c(Cys-His-D-Phe-Arg-Trp-Ala-D-Cys)-Thr-OH;

SEQ ID NO: 43
D-Phe-c(Cys-His-D-Phe-Arg-Trp-β-Ala-D-Cys)-Thr-OH;

SEQ ID NO: 43
D-Phe-c(Cys-His-D-Phe-Arg-Trp-Gaba-D-Cys)-Thr-OH;

SEQ ID NO: 42
Ac-Nle-c(Cys-His-D-Phe-Arg-Trp-Apn-Cys)-OH;

SEQ ID NO: 41
Ac-Nle-c(Asp-His-D-Phe-Arg-Trp-Apn-Lys)-OH;

SEQ ID NO: 44
Ac-Cha-c(Asp-His-D-Phe-Arg-Trp-Gaba-Lys)-OH;

SEQ ID NO: 44
Ac-Nle-c(Asp-His-D-Phe-Arg-Trp-Gaba-Lys)-OH;

SEQ ID NO: 29
Ac-Nle-c(Cys-D-Ala-His-D-Phe-Arg-Trp-Cys)-OH;

SEQ ID NO: 44
Ac-Chg-c(Asp-His-D-Phe-Arg-Trp-Gaba-Lys)-OH;

SEQ ID NO: 44
Ac-D-Cha-c(Asp-His-D-Phe-Arg-Trp-Gaba-Lys)-OH;

SEQ ID NO: 44
Ac-hCha-c(Asp-His-D-Phe-Arg-Trp-Gaba-Lys)-OH;

SEQ ID NO: 44
Ac-D-Chg-c(Asp-His-D-Phe-Arg-Trp-Gaba-Lys)-OH;

SEQ ID NO: 44
Ac-hPhe-c(Asp-His-D-Phe-Arg-Trp-Gaba-Lys)-OH;

SEQ ID NO: 45
Ac-Nle-c(Cys-His-D-Phe-Arg-D-Trp-Gaba-Cys)-OH;

SEQ ID NO: 45
Ac-Nle-c(Cys-His-D-Phe-Arg-D-Trp-Ahx-Cys)-OH;

SEQ ID NO: 45
Ac-Nle-c(Cys-His-D-Phe-Arg-D-Trp-β-Ala-Cys)-OH;

SEQ ID NO: 45
Ac-Nle-c(Cys-His-D-Phe-Arg-D-Trp-D-Ala-Cys)-OH;

SEQ ID NO: 46
Ac-Nle-c(Cys-D-Ala-His-D-2-Nal-Arg-Trp-Cys)-OH;

SEQ ID NO: 46
Ac-Nle-c(Cys-D-Ala-His-D-2-Nal-Arg-2-Nal-Cys)-OH;

SEQ ID NO: 46
Ac-Nle-c(Cys-D-Ala-His-D-2-Nal-Arg-1-Nal-Cys)-OH;

SEQ ID NO: 46
Ac-Nle-c(Cys-D-Ala-His-D-2-Nal-Arg-Bal-Cys)-OH;

SEQ ID NO: 47
Ac-Nle-c(Pen-D-Ala-His-D-Phe-Arg-Trp-Cys)-OH;

SEQ ID NO: 29
Ac-Nle-c(Cys-D-Ala-His-D-Phe-Arg-Trp-Pen)-OH;

SEQ ID NO: 48
Ac-Nle-c(Cys-His-D-Phe-Arg-Trp-Gaba-Pen)-OH;
``` or

SEQ ID NO: 49
Ac-Arg-c(Cys-D-Ala-His-D-2-Nal-Arg-Trp-Cys)-NH$_2$;

or pharmaceutically acceptable salts thereof.

More preferred of the immediately foregoing group of compounds is a compound of the formula:

SEQ ID NO: 7
Ac-Nle-c(Cys-D-Ala-His-D-Phe-Arg-Trp-Cys)-NH$_2$;

SEQ ID NO: 22
Ac-Nle-c(Cys-D-Ala-His-D-Phe-Arg-Trp-Pen)-NH$_2$;

SEQ ID NO: 32
Ac-Nle-c(Cys-His-D-Phe-Arg-Trp-Gaba-Pen)-NH$_2$;

SEQ ID NO: 29
Ac-Nle-c(Cys-D-Ala-His-D-Phe-Arg-Trp-Cys)-OH;

SEQ ID NO: 29
Ac-Nle-c(Cys-D-Ala-His-D-Phe-Arg-Trp-Pen)-OH;
or

SEQ ID NO: 48
Ac-Nle-c(Cys-His-D-Phe-Arg-Trp-Gaba-Pen)-OH;

or pharmaceutically acceptable salts thereof.

A more preferred compound of formula (I) is where said compound is of the formula:

$A^1$ is Arg, D-Arg, Cha, hCha, Chg, D-Chg, Ile, Leu, 2-Nal, Nle, Phe, D-Phe, hPhe, Val or deleted;

$A^2$ is Cys, Pen or Asp;

$A^3$ is D-Ala, D-Abu, D-Cha, D-Ile, D-Leu, D-Tle, D-Val or deleted;

$A^4$ is His or 3-Pal;

$A^5$ is D-Phe, D-2-Nal or D-(Et)Tyr;

$A^6$ is Arg or hArg;

$A^7$ is Trp, 2-Nal, Bal, Bip or D-Trp;

$A^8$ is Gly, Ala, β-Ala, Gaba, Apn, Ahx, or deleted;

$A^9$ is Cys, D-Cys, Pen or Lys;

$A^{10}$ is Thr or deleted;

each of $R^2$ and $R^3$ is independently selected from the group consisting of H or acyl;

or a pharmaceutically acceptable salt thereof.

More preferred of the immediately foregoing group of compounds is a compound of the formula:

SEQ ID NO: 50
Ac-Arg-c(Cys-D-Ala-His-D-Phe-Arg-Trp-Cys)-NH$_2$;

SEQ ID NO: 50
Ac-D-Arg-c(Cys-D-Ala-His-D-Phe-Arg-Trp-Cys)-NH$_2$;

SEQ ID NO: 51
Ac-D-Arg-c(Cys-D-Ala-His-D-Phe-Arg-Trp-Pen)-NH$_2$;

SEQ ID NO: 52
Ac-D-Arg-c(Cys-His-D-Phe-Arg-Trp-Gaba-Pen)-NH$_2$;

SEQ ID NO: 52
Ac-Arg-c(Cys-His-D-Phe-Arg-Trp-Gaba-Pen)-NH$_2$;

SEQ ID NO: 51
Ac-Arg-c(Cys-D-Ala-His-D-Phe-Arg-Trp-Pen)-NH$_2$;

SEQ ID NO: 53
Ac-D-Arg-c(Asp-His-D-Phe-Arg-Trp-Ala-Lys)-NH$_2$;

SEQ ID NO: 53
Ac-Arg-c(Asp-His-D-Phe-Arg-Trp-Ala-Lys)-NH$_2$;

SEQ ID NO: 7
Ac-Nle-c(Cys-D-Ala-His-D-Phe-Arg-Trp-Cys)-NH$_2$;

SEQ ID NO: 24
D-Phe-c(Cys-His-D-(Et)Tyr-Arg-Trp-β-Ala-D-Cys)-Thr-NH$_2$;

SEQ ID NO: 27
Nle-c(Cys-His-D-Phe-Arg-Trp-Apn-Cys)-NH$_2$;

SEQ ID NO: 32
Ac-Nle-c(Cys-His-D-Phe-Arg-Trp-Gaba-Pen)-NH$_2$;

SEQ ID NO: 34
Nle-c(Cys-His-D-Phe-Arg-Trp-Gaba-Cys)-NH$_2$;

SEQ ID NO: 1
Ac-Nle-c(Asp-His-D-Phe-Arg-Trp-β-Ala-Lys)-NH$_2$;

SEQ ID NO: 2
Ac-Nle-c(Cys-His-D-Phe-Arg-Trp-Ahx-Cys)-NH$_2$;

SEQ ID NO: 3
D-Phe-c(Cys-His-D-Phe-Arg-Trp-β-Ala-D-Cys)-Thr-NH$_2$;

```
                                               SEQ ID NO: 3
D-Phe-c(Cys-His-D-Phe-Arg-Trp-Gaba-D-Cys)-Thr-NH₂;

SEQ ID NO: 2
Ac-Nle-c(Cys-His-D-Phe-Arg-Trp-Apn-Cys)-NH₂;

SEQ ID NO: 4
Ac-Nle-c(Asp-His-D-Phe-Arg-Trp-Apn-Lys)-NH₂;

SEQ ID NO: 6
Ac-Cha-c(Asp-His-D-Phe-Arg-Trp-Gaba-Lys)-NH₂;

SEQ ID NO: 6
Ac-Nle-c(Asp-His-D-Phe-Arg-Trp-Gaba-Lys)-NH₂;

SEQ ID NO: 11
Ac-Chg-c(Asp-His-D-Phe-Arg-Trp-Gaba-Lys)-NH₂;

SEQ ID NO: 11
Ac-hCha-c(Asp-His-D-Phe-Arg-Trp-Gaba-Lys)-NH₂;

SEQ ID NO: 11
Ac-D-Chg-c(Asp-His-D-Phe-Arg-Trp-Gaba-Lys)-NH₂;

SEQ ID NO: 11
Ac-hPhe-c(Asp-His-D-Phe-Arg-Trp-Gaba-Lys)-NH₂;

SEQ ID NO: 15
Ac-Nle-c(Cys-His-D-Phe-Arg-D-Trp-β-Ala-Cys)-NH₂;

SEQ ID NO: 21
Ac-Nle-c(Pen-D-Ala-His-D-Phe-Arg-Trp-Cys)-NH₂;

SEQ ID NO: 22
Ac-Nle-c(Cys-D-Ala-His-D-Phe-Arg-Trp-Pen)-NH₂;

SEQ ID NO: 23
D-Phe-c(Cys-His-D-Phe-hArg-Trp-β-Ala-D-Cys)-Thr-NH₂;

SEQ ID NO: 25
D-Phe-c(Cys-His-D-Phe-Arg-Bip-β-Ala-D-Cys)-Thr-NH₂;

SEQ ID NO: 24
D-Phe-c(Cys-His-D-(Et)Tyr-hArg-Trp-β-Ala-D-Cys)-Thr-NH₂;

SEQ ID NO: 26
D-Phe-c(Cys-His-D-Phe-hArg-Bip-β-Ala-D-Cys)-Thr-NH₂;

SEQ ID NO: 26
D-Phe-c(Cys-His-D-(Et)Tyr-hArg-Bip-β-Ala-D-Cys)-Thr-NH₂;

SEQ ID NO: 28
Ac-Nle-c(Asp-D-Ala-His-D-Phe-Arg-Trp-Lys)-NH₂;

SEQ ID NO: 28
Ac-Nle-c(Asp-D-Ala-His-D-Phe-Arg-Bal-Lys)-NH₂;

SEQ ID NO: 29
Ac-Nle-c(Cys-D-Ala-His-D-Phe-Arg-Trp-Pen)-OH;

SEQ ID NO: 30
Ac-Nle-c(Cys-D-Abu-His-D-Phe-Arg-Trp-Cys)-NH₂;

SEQ ID NO: 30
Ac-Nle-c(Cys-D-Val-His-D-Phe-Arg-Trp-Cys)-NH₂;

SEQ ID NO: 30
Ac-Nle-c(Cys-D-Ile-His-D-Phe-Arg-Trp-Cys)-NH₂;

SEQ ID NO: 30
Ac-Nle-c(Cys-D-Leu-His-D-Phe-Arg-Trp-Cys)-NH₂;

SEQ ID NO: 30
Ac-Nle-c(Cys-D-Tle-His-D-Phe-Arg-Trp-Cys)-NH₂;

SEQ ID NO: 30
Ac-Nle-c(Cys-D-Cha-His-D-Phe-Arg-Trp-Cys)-NH₂;

SEQ ID NO: 31
Ac-Nle-c(Pen-His-D-Phe-Arg-Trp-Gaba-Cys)-NH₂;
```

-continued

Ac-Nle-c(Pen-His-D-Phe-Arg-Trp-Gaba-Pen)-NH₂;  SEQ ID NO: 32

Ac-Leu-c(Cys-His-D-Phe-Arg-Trp-Gaba-Cys)-NH₂;  SEQ ID NO: 33

Ac-Cha-c(Cys-His-D-Phe-Arg-Trp-Gaba-Cys)-NH₂;  SEQ ID NO: 33

Ac-Ile-c(Cys-His-D-Phe-Arg-Trp-Gaba-Cys)-NH₂;  SEQ ID NO: 33

Ac-Phe-c(Cys-His-D-Phe-Arg-Trp-Gaba-Cys)-NH₂;  SEQ ID NO: 33

Ac-Val-c(Cys-His-D-Phe-Arg-Trp-Gaba-Cys)-NH₂;  SEQ ID NO: 33

Ac-2-Nal-c(Cys-His-D-Phe-Arg-Trp-Gaba-Cys)-NH₂;  SEQ ID NO: 33

Phe-c(Cys-His-D-Phe-Arg-Trp-Gaba-Cys)-NH₂;  SEQ ID NO: 34

Ac-Nle-c(Cys-3Pal-D-Phe-Arg-Trp-Gaba-Cys)-NH₂;  SEQ ID NO: 35

Ac-Nle-c(Cys-D-Ala-His-D-Phe-Arg-Trp-Cys)-OH;  SEQ ID NO: 36

Ac-Nle-c(Cys-His-Phe-Arg-D-Trp-Gaba-Cys)-NH₂;  SEQ ID NO: 37

Ac-Nle-c(Cys-D-Ala-His-D-2-Nal-Arg-Trp-Cys)-NH₂;  SEQ ID NO: 16

Ac-Nle-c(Cys-D-Ala-His-D-2-Nal-Arg-2-Nal-Cys)-NH₂;  SEQ ID NO: 16

Ac-Nle-c(Cys-D-Ala-His-D-2-Nal-Arg-Bal-Cys)-NH₂;  SEQ ID NO: 20

Ac-Nle-c(Asp-His-D-2-Nal-Arg-Trp-Ala-Lys)-NH₂;  SEQ ID NO: 38

Ac-Nle-c(Asp-His-D-2-Nal-Arg-Trp-β-Ala-Lys)-NH₂;  SEQ ID NO: 38

Ac-Nle-c(Cys-His-D-2-Nal-Arg-Trp-Gaba-Cys)-NH₂;  SEQ ID NO: 39

Ac-Nle-c(Cys-His-D-2-Nal-Arg-Trp-Ahx-Cys)-NH₂;  SEQ ID NO: 39

Ac-hPhe-c(Asp-His-D-2-Nal-Arg-Trp-Gaba-Lys)-NH₂;  SEQ ID NO: 40

Ac-Cha-c(Asp-His-D-2-Nal-Arg-Trp-Gaba-Lys)-NH₂;  SEQ ID NO: 40
or

Ac-Arg-c(Cys-D-Ala-His-D-2-Nal-Arg-Trp-Cys)-NH₂;  SEQ ID NO: 49 or a pharmaceutically acceptable salt thereof.

A more preferred compound of formula (I) is where said compound is of the formula:
$A^1$ is Arg, D-Arg, hArg or D-hArg;
or a pharmaceutically acceptable salt thereof.

A more preferred compound of the immediately foregoing group of compounds is where said compound is of the formula:
$A^2$ is Cys, D-Cys, hCys, D-hCys, Pen, D-Pen, Asp, or Glu;
$A^3$ is Gly, Ala, D-Ala, D-Glu, β-Ala, Gaba, Aib, or deleted;
$A^4$ is His;
$A^5$ is D-Phe, D-1-Nal, D-2-Nal, D-Trp, D-Bal, or D-(Et)Tyr;
$A^6$ is Arg, or hArg;
$A^7$ is Trp, Bip, D-Trp, 1-Nal, or 2-Nal;
$A^8$ is A6c, Ala, β-Ala, Gaba, Apn, or Ahx;
$A^9$ is Cys, D-Cys, hCys, D-hCys, Pen, D-Pen, or Lys;
$A^{10}$ is Thr, or deleted;
or a pharmaceutically acceptable salt thereof.

A more preferred compound of the immediately foregoing group of compounds is where $R^2$ and $R^3$ each is, independently, H, acyl, n-propanoyl, or n-butanoyl or a pharmaceutically acceptable salt thereof.

A more preferred compound of the immediately foregoing group of compounds is where said compound is of the formula:

A² is Cys or Asp;
A³ is D-Ala or deleted;
A⁴ is His;
A⁵ is D-Phe or D-2-Nal;
A⁶ is Arg;
A⁷ is Trp;
A⁸ is Ala, Gaba or deleted;
A⁹ is Cys, Pen or Lys;
A¹⁰ is deleted;
or a pharmaceutically acceptable salt thereof.

A more preferred compound of the immediately foregoing group of compounds is where $R^2$ and $R^3$ each is, independently, H or acyl; or a pharmaceutically acceptable salt thereof.

More preferred of the immediately foregoing group of compounds is a compound of the formula:

SEQ ID NO: 50
Ac-Arg-c(Cys-D-Ala-His-D-Phe-Arg-Trp-Cys)-NH₂;

SEQ ID NO: 50
Ac-D-Arg-c(Cys-D-Ala-His-D-Phe-Arg-Trp-Cys)-NH₂;

SEQ ID NO: 51
Ac-D-Arg-c(Cys-D-Ala-His-D-Phe-Arg-Trp-Pen)-NH₂;

SEQ ID NO: 52
Ac-D-Arg-c(Cys-His-D-Phe-Arg-Trp-Gaba-Pen)-NH₂;

SEQ ID NO: 52
Ac-Arg-c(Cys-His-D-Phe-Arg-Trp-Gaba-Pen)-NH₂;

SEQ ID NO: 51
Ac-Arg-c(Cys-D-Ala-His-D-Phe-Arg-Trp-Pen)-NH₂;

SEQ ID NO: 53
Ac-D-Arg-c(Asp-His-D-Phe-Arg-Trp-Ala-Lys)-NH₂;

SEQ ID NO: 53
Ac-Arg-c(Asp-His-D-Phe-Arg-Trp-Ala-Lys)-NH₂;
or

SEQ ID NO: 49
Ac-Arg-c(Cys-D-Ala-His-D-2-Nal-Arg-Trp-Cys)-NH₂;

or pharmaceutically acceptable salts thereof.

More preferred of the immediately foregoing group of compounds is a compound of the formula:

SEQ ID NO: 50
Ac-Arg-c(Cys-D-Ala-His-D-Phe-Arg-Trp-Cys)-NH₂;

SEQ ID NO: 51
Ac-D-Arg-c(Cys-D-Ala-His-D-Phe-Arg-Trp-Pen)-NH₂;
or

SEQ ID NO: 49
Ac-Arg-c(Cys-D-Ala-His-D-2-Nal-Arg-Trp-Cys)-NH₂;

or a pharmaceutically acceptable salt thereof.

More preferred of the immediately foregoing group of compounds is a compound of the formula:

SEQ ID NO: 50
Ac-Arg-c(Cys-D-Ala-His-D-Phe-Arg-Trp-Cys)-NH₂;

or a pharmaceutically acceptable salt thereof.

More preferred of the immediately foregoing group of compounds is a compound of the formula:

SEQ ID NO: 51
Ac-D-Arg-c(Cys-D-Ala-His-D-Phe-Arg-Trp-Pen)-NH₂;

or a pharmaceutically acceptable salt thereof.

More preferred of the immediately foregoing group of compounds is a compound of the formula:

SEQ ID NO: 49
Ac-Arg-c(Cys-D-Ala-His-D-2-Nal-Arg-Trp-Cys)-NH₂;

or a pharmaceutically acceptable salt thereof.

In one aspect, the present invention is directed to a compound according formula (II):

$$(R^2R^3)\text{-}A^1\text{-}c(A^2\text{-}A^3\text{-}A^4\text{-}A^5\text{-}A^6\text{-}A^7\text{-}A^8\text{-}A^9)\text{-}NH_2$$

wherein
A¹ is Nle or deleted;
A² is Cys or Asp;
A³ is Glu or D-Ala;
A⁴ is His;
A⁵ is D-Phe;
A⁶ is Arg;
A⁷ is Trp, 2-Nal or Bal;
A⁸ is Gly, Ala, D-Ala, β-Ala, Gaba or Apn;
A⁹ is Cys or Lys;
each of $R^2$ and $R^3$ is independently selected from the group consisting of H or $(C_1\text{-}C_6)$acyl;
provided that
(I). when $R^2$ is $(C_1\text{-}C_6)$acyl, then $R^3$ is H; and
(II). when $A^2$ is Cys, then $A^9$ is Cys,
or a pharmaceutically acceptable salt thereof.

More preferred of the immediately foregoing group of compounds is a compound of the formula:

SEQ ID NO: 54
Ac-Nle-c(Cys-D-Ala-His-D-Phe-Arg-Trp-Gly-Cys)-NH₂;

SEQ ID NO: 54
Ac-Nle-c(Cys-D-Ala-His-D-Phe-Arg-Trp-D-Ala-Cys)-NH₂;

SEQ ID NO: 54
Ac-Nle-c(Cys-D-Ala-His-D-Phe-Arg-Trp-β-Ala-Cys)-NH₂;

SEQ ID NO: 54
Ac-Nle-c(Cys-D-Ala-His-D-Phe-Arg-Trp-Gaba-Cys)-NH₂;

SEQ ID NO: 54
Ac-Nle-c(Cys-D-Ala-His-D-Phe-Arg-Trp-Apn-Cys)-NH₂;

SEQ ID NO: 55
Ac-c(Cys-Glu-His-D-Phe-Arg-Trp-Ala-Cys)-NH₂;

SEQ ID NO: 55
Ac-c(Cys-Glu-His-D-Phe-Arg-2-Nal-Ala-Cys)-NH₂;

SEQ ID NO: 56
Ac-c(Cys-D-Ala-His-D-Phe-Arg-Trp-Ala-Cys)-NH₂;

SEQ ID NO: 56
Ac-c(Cys-D-Ala-His-D-Phe-Arg-2-Nal-Ala-Cys)-NH₂;

SEQ ID NO: 57
Ac-Nle-c(Cys-D-Ala-His-D-Phe-Arg-Trp-Ala-Cys)-NH₂;

SEQ ID NO: 57
Ac-Nle-c(Cys-D-Ala-His-D-Phe-Arg-Trp-β-Ala-Cys)-NH₂;

SEQ ID NO: 57
Ac-Nle-c(Cys-D-Ala-His-D-Phe-Arg-Trp-Gaba-Cys)-NH₂;
or

SEQ ID NO: 58
Ac-Nle-c(Asp-D-Ala-His-D-Phe-Arg-Bal-Ala-Lys)-NH₂;

or a pharmaceutically acceptable salt thereof.

Another more preferred compound of formula (I) or formula (II) is each of the compounds that are specifically enumerated herein below in the Examples section of the present disclosure, or a pharmaceutically acceptable salt thereof.

In another aspect, the present invention provides a pharmaceutical composition comprising an effective amount of a compound of formula (I) or formula (II) as defined hereinabove or a pharmaceutically acceptable salt thereof and a pharmaceutically acceptable carrier or diluent.

In another aspect, the present invention provides a pharmaceutical composition comprising an effective amount of a compound of formula (I) or formula (II) as defined hereinabove, or a pharmaceutically acceptable salt thereof, together with a pharmaceutically acceptable carrier or diluent, wherein said compound is a selective melanocortin-4 receptor agonist.

In another aspect, the present invention provides a pharmaceutical composition comprising an effective amount of a compound of formula (I) or formula (II) as defined hereinabove, or a pharmaceutically acceptable salt thereof, together with a pharmaceutically acceptable carrier or diluent, wherein said compound is a selective melanocortin 4 receptor agonist with a functional activity characterized by an $EC_{50}$ at least 15-fold more selective for the human melanocortin 4 receptor than for the human melanocortin 1 receptor, the human melanocortin 3 receptor and the human melanocortin 5 receptor.

In yet another aspect, the present invention provides a pharmaceutical composition comprising an effective amount of a compound of formula (I) or formula (II) as defined hereinabove, or a pharmaceutically acceptable salt thereof, together with a pharmaceutically acceptable carrier or diluent, wherein said compound is a selective melanocortin 4 receptor agonist with a functional activity characterized by an $EC_{50}$ at least 17-fold more selective for the human melanocortin 4 receptor than for the human melanocortin 3 receptor, an $EC_{50}$ at least 90-fold more selective for the human melanocortin 4 receptor than for the human melanocortin 3 receptor, an $EC_{50}$ at least 200-fold more selective for the human melanocortin 4 receptor than for the human melanocortin 5 receptor, or an $EC_{50}$ at least 3000-fold more selective for the human melanocortin 4 receptor than for the human melanocortin 5 receptor.

In another aspect, the present invention provides a pharmaceutical composition comprising an effective amount of a compound of formula (I) or formula (II) as defined hereinabove, or a pharmaceutically acceptable salt thereof, together with a pharmaceutically acceptable carrier or diluent, useful for treating an acute or chronic inflammatory disease or medical condition such as general inflammation, inflammatory bowel disease, brain inflammation, sepsis and septic shock.

In another aspect, the present invention provides a pharmaceutical composition comprising an effective amount of a compound of formula (I) or formula (II) as defined hereinabove, or a pharmaceutically acceptable salt thereof, together with a pharmaceutically acceptable carrier or diluent, useful for treating a disease or medical condition with an autoimmune component such as rheumatoid arthritis, gouty arthritis and multiple sclerosis.

In another aspect, the present invention provides a pharmaceutical composition comprising an effective amount of a compound of formula (I) or formula (II) as defined hereinabove, or a pharmaceutically acceptable salt thereof, together with a pharmaceutically acceptable carrier or diluent, useful for treating a metabolic disease or medical condition accompanied by weight gain such as obesity, feeding disorders and Prader-Willi Syndrome. In a further aspect, the disease or condition treated is obesity. In yet a further aspect, the disease or condition treated is a feeding disorder.

In another aspect, the present invention provides a pharmaceutical composition comprising an effective amount of a compound of formula (I) or formula (II) as defined hereinabove, or a pharmaceutically acceptable salt thereof, together with a pharmaceutically acceptable carrier or diluent, useful for decreasing food intake, for decreasing body weight or a combination thereof. In a preferred embodiment, the present invention provides a pharmaceutical composition comprising an effective amount of a compound of formula (I) as defined hereinabove, or a pharmaceutically acceptable salt thereof, together with a pharmaceutically acceptable carrier or diluent, which is useful for diminishing food intake, decreasing body weight, or a combination thereof, wherein the active ingredient is one or more of the following compounds: Ac-Nle-c(Cys-His-D-Phe-Arg-Trp-Gaba-Pen)-$NH_2$ SEQ ID NO:32, Ac-Arg-c(Cys-D-Ala-His-D-Phe-Arg-Trp-Cys)-$NH_2$ SEQ ID NO:50, Ac-D-Arg-c(Cys-D-Ala-His-D-Phe-Arg-Trp-Cys)-$NH_2$ SEQ ID NO:50, Ac-D-Arg-c(Cys-D-Ala-His-D-Phe-Arg-Trp-Pen)-$NH_2$ SEQ ID NO:51, Ac-Nle-c(Cys-D-Ala-His-D-Phe-Arg-Trp-Cys)-$NH_2$ SEQ ID NO:7, D-Phe-c(Cys-His-D-(Et)Tyr-Arg-Trp-β-Ala-D-Cys)-Thr-$NH_2$ SEQ ID NO:24, Ac-Nle-c(Cys-D-Ala-His-D-Phe-Arg-Trp-Pen)-$NH_2$ SEQ ID NO:22 or Ac-Arg-c(Cys-D-Ala-His-D-2-Nal-Arg-Trp-Cys)-$NH_2$ SEQ ID NO:49. In yet another preferred embodiment, the present invention provides a pharmaceutical composition comprising an effective amount of a compound of formula (I) as defined hereinabove, or a pharmaceutically acceptable salt thereof, together with a pharmaceutically acceptable carrier or diluent, which is useful for diminishing food intake, decreasing body weight, or a combination thereof, wherein the active ingredient is Ac-Arg-c(Cys-D-Ala-His-D-Phe-Arg-Trp-Cys)-$NH_2$ SEQ ID NO:50. In yet another preferred embodiment, the present invention provides a pharmaceutical composition comprising an effective amount of a compound of formula (I) as defined hereinabove, or a pharmaceutically acceptable salt thereof, together with a pharmaceutically acceptable carrier or diluent, which is useful for diminishing food intake, decreasing body weight, or a combination thereof, wherein the active ingredient is Ac-D-Arg-c(Cys-D-Ala-His-D-Phe-Arg-Trp-Pen)-$NH_2$ SEQ ID NO:51. In yet another preferred embodiment, the present invention provides a pharmaceutical composition comprising an effective amount of a compound of formula (I) as defined hereinabove, or a pharmaceutically acceptable salt thereof, together with a pharmaceutically acceptable carrier or diluent, which is useful for diminishing food intake, decreasing body weight, or a combination thereof, wherein the active ingredient is Ac-Arg-c(Cys-D-Ala-His-D-2-Nal-Arg-Trp-Cys)-$NH_2$ SEQ ID NO:49.

In another aspect, the present invention provides a pharmaceutical composition comprising an effective amount of a compound of formula (I) or formula (II) as defined hereinabove, or a pharmaceutically acceptable salt thereof, together with a pharmaceutically-acceptable carrier or diluent, which is useful for decreasing appetite without compromising body weight. In yet another aspect, the present invention provides a pharmaceutical composition comprising an effective amount of a compound of formula (I) or formula (II) as defined hereinabove, or a pharmaceutically acceptable salt thereof, together with a pharmaceutically-acceptable carrier or diluent, useful for decreasing food consumption while increasing body weight.

In another aspect, the present invention provides a pharmaceutical composition comprising an effective amount of a compound of formula (I) or formula (II) as defined hereinabove, or a pharmaceutically acceptable salt thereof, together with a pharmaceutically acceptable carrier or diluent, useful for treating a metabolic disease or medical condition accompanied by weight loss such as anorexia, bulimia, AIDS wasting, cachexia, cancer cachexia and wasting in frail elderly. In a further aspect, the disease or condition treated is anorexia. In a further aspect, the disease or condition treated is bulimia. In a further aspect, the disease or condition treated is AIDS wasting or wasting in frail elderly. In a further aspect, the disease or condition treated is cachexia or cancer cachexia.

In another aspect, the present invention provides a pharmaceutical composition comprising an effective amount of a compound of formula (I) or formula (II) as defined hereinabove, or a pharmaceutically acceptable salt thereof, together with a pharmaceutically acceptable carrier or diluent, useful for treating a neoplastic disease or medical condition such as skin cancer and cancer cachexia.

In another aspect, the present invention provides a pharmaceutical composition comprising an effective amount of a compound of formula (I) or formula (II) as defined hereinabove, or a pharmaceutically acceptable salt thereof, together with a pharmaceutically acceptable carrier or diluent, useful for treating a reproductive or sexual medical condition such as endometriosis, uterine bleeding, sexual dysfunction, erectile dysfunction and decreased sexual response in females.

In another aspect, the present invention provides a pharmaceutical composition comprising an effective amount of a compound of formula (I) or formula (II) as defined hereinabove, or a pharmaceutically acceptable salt thereof, together with a pharmaceutically acceptable carrier or diluent, useful for treating a disease or medical condition resulting from treatment or insult to an organism such as organ transplant rejection, ischemia and reperfusion injury, wounding and spinal cord injury, and weight loss due to a medical procedure selected from the group consisting of chemotherapy, radiation therapy, temporary or permanent immobilization and dialysis.

In another aspect, the present invention provides a pharmaceutical composition comprising an effective amount of a compound of formula (I) or formula (II) as defined hereinabove, or a pharmaceutically acceptable salt thereof, together with a pharmaceutically acceptable carrier or diluent, useful for treating a cardiovascular disease or medical condition such as hemorrhagic shock, cardiogenic shock, hypovolemic shock, cardiovascular disorders and cardiac cachexia.

In another aspect, the present invention provides a pharmaceutical composition comprising an effective amount of a compound of formula (I) or formula (II) as defined hereinabove, or a pharmaceutically acceptable salt thereof, together with a pharmaceutically acceptable carrier or diluent, useful for treating a pulmonary disease or medical condition such as acute respiratory distress syndrome, pulmonary fibrosis, chronic obstructive pulmonary disease and asthma.

In another aspect, the present invention provides a pharmaceutical composition comprising an effective amount of a compound of formula (I) or formula (II) as defined hereinabove, or a pharmaceutically acceptable salt thereof, together with a pharmaceutically acceptable carrier or diluent, useful for enhancing immune tolerance and treating allergies.

In another aspect, the present invention provides a pharmaceutical composition comprising an effective amount of a compound of formula (I) or formula (II) as defined hereinabove, or a pharmaceutically acceptable salt thereof, together with a pharmaceutically acceptable carrier or diluent, useful for treating a dermatological disease or medical condition such as psoriasis, skin pigmentation depletion, acne and keloid formation.

In another aspect, the present invention provides a pharmaceutical composition comprising an effective amount of a compound of formula (I) or formula (II) as defined hereinabove, or a pharmaceutically acceptable salt thereof, together with a pharmaceutically-acceptable carrier or diluent, useful for treating a behavioral or central nervous system or neuronal disease or medical condition such as anxiety, depression, memory dysfunction and neuropathic pain.

In another aspect, the present invention provides a pharmaceutical composition comprising an effective amount of a compound of formula (I) or formula (II) as defined hereinabove, or a pharmaceutically acceptable salt thereof, together with a pharmaceutically-acceptable carrier or diluent, useful for treating a renal disease or medical condition such as renal cachexia and natriuresis.

In another aspect, the present invention provides a pharmaceutical composition comprising an effective amount of a compound of formula (I) or formula (II) as defined hereinabove, or a pharmaceutically acceptable salt thereof, together with a pharmaceutically-acceptable carrier or diluent, useful for modulating ovarian weight, placental development, prolactin secretion, FSH secretion, intrauterine fetal growth, parturition, spermatogenesis, thyroxin release, aldosterone synthesis and release, body temperature, blood pressure, heart rate, vascular tone, brain blood flow, blood glucose levels, sebum secretion, pheromone secretion, motivation, learning and behavior, pain perception, neuroprotection and nerve growth.

In another aspect, the present invention provides a pharmaceutical composition comprising an effective amount of a compound of formula (I) or formula (II) as defined hereinabove, or a pharmaceutically acceptable salt thereof, together with a pharmaceutically-acceptable carrier or diluent, useful for modulating bone metabolism, bone formation and bone development.

In another aspect, the present invention provides a pharmaceutical composition comprising an effective amount of a compound of formula (I) or formula (II) as defined hereinabove, or a pharmaceutically acceptable salt thereof, together with a pharmaceutically-acceptable carrier or diluent, useful for inhibiting alcohol consumption, for reducing alcohol consumption, for treating alcoholism, or for treating alcohol abuse. In a further aspect, the compound of the composition useful for inhibiting alcohol consumption, for reducing alcohol consumption, for treating alcoholism, or for treating alcohol abuse is a selective melanocortin 4 receptor agonist. In yet a further aspect, the compound of the composition useful for inhibiting alcohol consumption is a selective melanocortin 4 receptor agonist, or a pharmaceutically acceptable salt thereof, with a functional activity characterized by an $EC_{50}$ at least 15-fold more selective for the human melanocortin 4 receptor than for the human melanocortin 1 receptor, the human melanocortin 3 receptor and the human melanocortin 5 receptor. In yet another aspect, the compound of the composition useful for inhibiting alcohol consumption is a selective melanocortin 4 receptor agonist, or a pharmaceutically acceptable salt thereof, with a functional activity characterized by an $EC_{50}$ at least 17-fold more selective for the human melanocortin 4 receptor than for the human melanocortin 3 receptor, an $EC_{50}$ at least 90-fold more selective for the human melanocortin 4 receptor than for the human melanocortin 3 receptor, an $EC_{50}$ at least 200-fold more selective for the human melanocortin 4 receptor than for the human melanocortin 5 receptor, or an $EC_{50}$ at least 3000-fold more selective for the human melanocortin 4 receptor than for the human melanocortin 5 receptor.

In another aspect, the present invention provides the use of a therapeutically effective amount of a melanocortin 4 receptor agonist compound of formula (I) or formula (II) as defined hereinabove, or a pharmaceutically acceptable salt thereof, for the manufacture of a medicament useful for inhibiting alcohol consumption, for reducing alcohol consumption, for treating alcoholism, or for treating alcohol abuse in a subject in need of such treatment.

In yet another aspect, the present invention provides a method of eliciting an agonist or an antagonist effect from a melanocortin receptor in a subject in need thereof which comprises administering to said subject an effective amount of a compound of formula (I) or formula (II) as defined hereinabove, or a pharmaceutically acceptable salt thereof.

In another aspect, the present invention provides a method of eliciting an agonist or an antagonist effect from a melanocortin receptor in a subject in need thereof which comprises administering to said subject an effective amount of a compound of formula (I) or formula (II) as defined hereinabove, or a pharmaceutically acceptable salt thereof, wherein said compound is a selective melanocortin 4 receptor agonist.

In another aspect, the present invention provides a method of eliciting an agonist or an antagonist effect from a melanocortin receptor in a subject in need thereof which comprises administering to said subject an effective amount of a compound of formula (I) or formula (II) as defined hereinabove, or a pharmaceutically acceptable salt thereof, wherein said compound is a selective melanocortin 4 receptor agonist with a functional activity characterized by an $EC_{50}$ at least 15-fold more selective for the human melanocortin 4 receptor than for the human melanocortin 1 receptor, the human melanocortin 3 receptor and the human melanocortin 5 receptor.

In yet another aspect, the present invention provides a method of eliciting an agonist or an antagonist effect from a melanocortin receptor in a subject in need thereof which comprises administering to said subject an effective amount of a compound of formula (I) or formula (II) as defined hereinabove, or a pharmaceutically acceptable salt thereof, wherein said compound is a selective melanocortin 4 receptor agonist with a functional activity characterized by an $EC_{50}$ at least 17-fold more selective for the human melanocortin 4 receptor than for the human melanocortin 3 receptor, an $EC_{50}$ at least 90-fold more selective for the human melanocortin 4 receptor than for the human melanocortin 3 receptor, an $EC_{50}$ at least 200-fold more selective for the human melanocortin 4 receptor than for the human melanocortin 5 receptor, or an $EC_{50}$ at least 3000-fold more selective for the human melanocortin 4 receptor than for the human melanocortin 5 receptor.

In another aspect, the present invention provides a method of treating an acute or chronic inflammatory disease or medical condition such as general inflammation, inflammatory bowel disease, brain inflammation, sepsis and septic shock by eliciting an agonist or antagonist effect from a melanocortin receptor by administering an effective amount of a compound of formula (I) or formula (II) as defined hereinabove, or a pharmaceutically acceptable salt thereof.

In another aspect, the present invention provides a method of treating a disease or medical condition with an autoimmune component such as rheumatoid arthritis, gouty arthritis and multiple sclerosis by eliciting an agonist or antagonist effect from a melanocortin receptor by administering an effective amount of a compound of formula (I) or formula (II) as defined hereinabove, or a pharmaceutically acceptable salt thereof.

In another aspect, the present invention provides a method of treating a metabolic disease or medical condition accompanied by weight gain such as obesity, feeding disorders and Prader-Willi Syndrome by eliciting an agonist or antagonist effect from a melanocortin receptor by administering an effective amount of a compound of formula (I) or formula (II) as defined hereinabove, or a pharmaceutically acceptable salt thereof. In a further aspect of the foregoing method, the disease or condition treated is obesity. In yet a further aspect of the foregoing method, the disease or condition treated is a feeding disorder.

In another aspect, the present invention provides a method of decreasing food intake, decreasing body weight or a combination thereof, by eliciting an agonist or antagonist effect from a melanocortin receptor by administering an effective amount of a compound of formula (I) or formula (II) as defined hereinabove, or a pharmaceutically acceptable salt thereof. In a preferred embodiment, the present invention provides a method of decreasing food intake, decreasing body weight or a combination thereof, by eliciting an agonist or antagonist effect from a melanocortin receptor by administering an effective amount of a compound of formula (I) or a pharmaceutically acceptable salt thereof, wherein said compound is Ac-Nle-c(Cys-His-D-Phe-Arg-Trp-Gaba-Pen)-NH$_2$ SEQ ID NO:32, Ac-Arg-c(Cys-D-Ala-His-D-Phe-Arg-Trp-Cys)-NH$_2$ SEQ ID NO:50, Ac-D-Arg-c(Cys-D-Ala-His-D-Phe-Arg-Trp-Cys)-NH$_2$ SEQ ID NO:50, Ac-D-Arg-c(Cys-D-Ala-His-D-Phe-Arg-Trp-Pen)-NH$_2$ SEQ ID NO:51, Ac-Nle-c(Cys-D-Ala-His-D-Phe-Arg-Trp-Cys)-NH$_2$ SEQ ID NO:7, D-Phe-c(Cys-His-D-(Et)Tyr-Arg-Trp-β-Ala-D-Cys)-Thr-NH$_2$ SEQ ID NO:24, Ac-Nle-c(Cys-D-Ala-His-D-Phe-Arg-Trp-Pen)-NH$_2$ SEQ ID NO:22, or Ac-Arg-c(Cys-D-Ala-His-D-2-Nal-Arg-Trp-Cys)-NH$_2$ SEQ ID NO:49. In another preferred embodiment, the present invention provides a method of decreasing food intake, decreasing body weight or a combination thereof, by eliciting an agonist or antagonist effect from a melanocortin receptor by administering an effective amount of a compound of formula (I) or a pharmaceutically acceptable salt thereof, wherein said compound is Ac-Arg-c(Cys-D-Ala-His-D-Phe-Arg-Trp-Cys)-NH$_2$ SEQ ID NO:50. In another preferred embodiment, the present invention provides a method of decreasing food intake, decreasing body weight or a combination thereof, by eliciting an agonist or antagonist effect from a melanocortin receptor by administering an effective amount of a compound of formula (I) or a pharmaceutically acceptable salt thereof, wherein said compound is Ac-D-Arg-c(Cys-D-Ala-His-D-Phe-Arg-Trp-Pen)-NH$_2$ SEQ ID NO:51. In another preferred embodiment, the present invention provides a method of decreasing food intake, decreasing body weight or a combination thereof, by eliciting an agonist or antagonist effect from a melanocortin receptor by administering an effective amount of a compound of formula (I) or a pharmaceutically acceptable salt thereof, wherein said compound is Ac-Arg-c(Cys-D-Ala-His-D-2-Nal-Arg-Trp-Cys)-NH$_2$ SEQ ID NO:49.

In another aspect, the present invention provides a method of decreasing appetite without compromising body weight by administering an effective amount of a compound of formula (I) or formula (II) as defined hereinabove, or a pharmaceutically acceptable salt thereof. In another aspect, the present invention, provides a method of decreasing food consumption while increasing body weight by administering an effective amount of a compound of formula (I) or formula (II) as defined hereinabove, or a pharmaceutically acceptable salt thereof.

In another aspect, the present invention provides a method of treating a metabolic disease or medical condition accompanied by weight loss such as anorexia, bulimia, AIDS wasting, cachexia, cancer cachexia and wasting in frail elderly by eliciting an agonist or antagonist effect from a melanocortin receptor by administering an effective amount of a compound of formula (I) or formula (II) as defined hereinabove, or a pharmaceutically acceptable salt thereof. In a further aspect, the foregoing method is used to treat anorexia. In a further aspect, the foregoing method is used to treat bulimia. In a further aspect, the foregoing method is used to treat AIDS wasting or wasting in frail elderly. In a further aspect, the foregoing method is used to treat cachexia or cancer cachexia.

In another aspect, the present invention provides a method of treating a neoplastic disease or medical condition such as skin cancer and cancer cachexia by eliciting an agonist or antagonist effect from a melanocortin receptor by administering an effective amount of a compound of formula (I) or formula (II) as defined hereinabove, or a pharmaceutically acceptable salt thereof.

In another aspect, the present invention provides a method of treating a reproductive or sexual medical condition such as endometriosis, uterine bleeding, sexual dysfunction, erectile dysfunction and decreased sexual response in females by eliciting an agonist or antagonist effect from a melanocortin receptor by administering an effective amount of a compound of formula (I) or formula (II) as defined hereinabove, or a pharmaceutically acceptable salt thereof.

In another aspect, the present invention provides a method of treating a disease or medical condition resulting from treatment or insult to an organism such as organ transplant rejection, ischemia and reperfusion injury, wounding and spinal cord injury, and weight loss due to a medical procedure selected from the group consisting of chemotherapy, radiation therapy, temporary or permanent immobilization and dialysis by eliciting an agonist or antagonist effect from a melanocortin receptor by administering an effective amount of a compound of formula (I) or formula (II) as defined hereinabove, or a pharmaceutically acceptable salt thereof.

In another aspect, the present invention provides a method of treating a cardiovascular disease or medical condition such as hemorrhagic shock, cardiogenic shock, hypovolemic shock, cardiovascular disorders and cardiac cachexia by eliciting an agonist or antagonist effect from a melanocortin receptor by administering an effective amount of a compound of formula (I) or formula (II) as defined hereinabove, or a pharmaceutically acceptable salt thereof.

In another aspect, the present invention provides a method of treating a pulmonary disease or medical condition such as acute respiratory distress syndrome, pulmonary fibrosis, chronic obstructive pulmonary disease and asthma by eliciting an agonist or antagonist effect from a melanocortin receptor by administering an effective amount of a compound of formula (I) or formula (II) as defined hereinabove, or a pharmaceutically acceptable salt thereof.

In another aspect, the present invention provides a method of enhancing immune tolerance or treating allergies by eliciting an agonist or antagonist effect from a melanocortin receptor by administering an effective amount of a compound of formula (I) or formula (II) as defined hereinabove, or a pharmaceutically acceptable salt thereof.

In another aspect, the present invention provides a method of treating dermatological disease or medical condition such as psoriasis, skin pigmentation depletion, acne and keloid formation by eliciting an agonist or antagonist effect from a melanocortin receptor by administering an effective amount of a compound of formula (I) or formula (II) as defined hereinabove, or a pharmaceutically acceptable salt thereof.

In another aspect, the present invention provides a method of treating a behavioral or central nervous system or neuronal disease or medical condition such as anxiety, depression, memory dysfunction and neuropathic pain by eliciting an agonist or antagonist effect from a melanocortin receptor by administering an effective amount of a compound of formula (I) or formula (II) as defined hereinabove, or a pharmaceutically acceptable salt thereof.

In another aspect, the present invention provides a method of treating a renal disease or medical condition such as renal cachexia and natriuresis by eliciting an agonist or antagonist effect from a melanocortin receptor by administering an effective amount of a compound of formula (I) or formula (II) as defined hereinabove, or a pharmaceutically acceptable salt thereof.

In another aspect, the present invention provides a method of modulating a normalizing or homeostatic activity such as ovarian weight, placental development, prolactin secretion, FSH secretion, intrauterine fetal growth, parturition, spermatogenesis, thyroxin release, aldosterone synthesis and release, body temperature, blood pressure, heart rate, vascular tone, brain blood flow, blood glucose levels, sebum secretion, pheromone secretion, motivation, learning and behavior, pain perception, neuroprotection and nerve growth by eliciting an agonist or antagonist effect from a melanocortin receptor by administering an effective amount of a compound of formula (I) or formula (II) as defined hereinabove, or a pharmaceutically acceptable salt thereof.

In another aspect, the present invention provides a method of modulating a normalizing or homeostatic activity such as bone metabolism, bone formation and bone development by eliciting an agonist or antagonist effect from a melanocortin receptor by administering an effective amount of a compound of formula (I) or formula (II) as defined hereinabove, or a pharmaceutically acceptable salt thereof.

In another aspect, the present invention provides a method of inhibiting alcohol consumption, for reducing alcohol consumption, for treating alcoholism, or for treating alcohol abuse by eliciting an agonist or antagonist effect from a melanocortin receptor by administering an effective amount of a compound of formula (I) or formula (II) as defined hereinabove, or a pharmaceutically acceptable salt thereof. In a further aspect of the foregoing method, the compound is a selective melanocortin 4 receptor agonist. In yet a further aspect of the immediately foregoing method, the compound of the composition useful for inhibiting alcohol consumption is a selective melanocortin 4 receptor agonist, or a pharmaceutically acceptable salt thereof, with a functional activity characterized by an $EC_{50}$ at least 15-fold more selective for the human melanocortin 4 receptor than for the human melanocortin 1 receptor, the human melanocortin 3 receptor and the human melanocortin 5 receptor. In yet another aspect of the foregoing method, the compound of the composition useful for inhibiting alcohol consumption is a selective melanocortin 4 receptor agonist, or a pharmaceutically acceptable salt thereof, with a functional activity characterized by an $EC_{50}$ at least 17-fold more selective for the human melanocortin 4 receptor than for the human melanocortin 3 receptor, an $EC_{50}$ at least 90-fold more selective for the human melanocortin 4 receptor than for the human melanocortin 3 receptor, an $EC_{50}$ at least 200-fold more selective for the human melanocortin 4 receptor than for the human melanocortin 5 receptor, or an $EC_{50}$ at least 3000-fold more selective for the human melanocortin 4 receptor than for the human melanocortin 5 receptor.

In a further aspect, the present invention provides the use of a therapeutically effective amount of a melanocortin 4 receptor agonist or antagonist compound according formula (I) or formula (II) as defined hereinabove, or a pharmaceutically acceptable salt thereof, for the manufacture of a medicament useful to treat a disease and/or medical condition selected from the group consisting of acute and chronic inflammatory diseases such as general inflammation, inflammatory bowel disease, brain inflammation, sepsis and septic shock; diseases with an autoimmune component such as rheumatoid arthritis, gouty arthritis and multiple sclerosis; metabolic diseases and medical disorders accompanied by weight gain such as obesity, feeding disorders and Prader-Willi Syndrome; metabolic diseases and medical disorders accompanied by weight loss such as anorexia, bulimia, AIDS wasting, cachexia, cancer cachexia and wasting in frail elderly; diabetes, diabetalogical related conditions and complications of diabetes such as retinopathy; neoplastic proliferation such as skin cancer and prostate cancer; reproductive or sexual medical conditions such as endometriosis and uterine bleeding in women, sexual dysfunction, erectile dysfunction and decreased sexual response in females; diseases or conditions resulting from treatment or insult to the organism such as organ transplant rejection, ischemia and reperfusion injury, spinal cord injury and wounding, as well as weight loss caused chemotherapy, radiation therapy, temporary or permanent immobilization or dialysis; cardiovascular diseases or conditions such as hemorrhagic shock, cardiogenic shock, hypovolemic shock, cardiovascular disorders and cardiac cachexia; pulmonary diseases or conditions such as acute respiratory distress syndrome, chronic obstructive pulmonary disease, asthma and pulmonary fibrosis; to enhance immune tolerance and to combat assaults to the immune system such as those associated with certain allergies or organ transplant rejection; treatment of dermatological diseases and conditions such as psoriasis, skin pigmentation depletion, acne, keloid formation and skin cancer; behavioral, central nervous system and neuronal disorders such as anxiety, depression, memory dysfunction, and neuropathic pain; and renal conditions or diseases such as the treatment of renal cachexia and natriuresis.

In a further aspect, the present invention provides the use of a therapeutically effective amount of a melanocortin 4 receptor agonist or antagonist compound according formula (I) or formula (II) as defined hereinabove, or a pharmaceutically acceptable salt thereof, for the manufacture of a medicament useful to modulate normalizing or homeostatic activities such as ovarian weight, placental development, prolactin secretion, FSH secretion, intrauterine fetal growth, parturition, spermatogenesis, thyroxin release, aldosterone synthesis and release, body temperature, blood pressure, heart rate, vascular tone, brain blood flow, blood glucose levels, sebum secretion, pheromone secretion, motivation, learning and behavior, pain perception, neuroprotection, nerve growth, bone metabolism, bone formation and bone development.

It will be appreciated that therapeutic interventions addressing both normal physiological and pathophysiological processes which utilize the melanocortin receptors are also contemplated.

Additional objects, advantages, and features of the present invention will become apparent from the following description and appended claims, taken in conjunction with the accompanying drawings.

The compounds of formulae (I) or (II) are ligands for at least one of the melanocortin receptors (MC1-R, MC2-R, MC3-R, MC4-R and MC5-R) and a selection thereof were tested for their ability to act as a ligand in the in vitro assay described below.

BRIEF DESCRIPTION OF THE DRAWINGS

FIG. 1A: Mean difference in food consumed from vehicle in fasted rats 6 hours after administration of 100 nmole/Kg of selected compounds.

FIG. 1B. Mean difference in food consumed from vehicle in fasted rats 6 hours after administration of 500 nmole/Kg of selected compounds.

FIG. 4A. Cumulative difference in mean food intake from vehicle in rats after administration of selected compounds.

DETAILED DESCRIPTION OF THE INVENTION

Figure 2A:
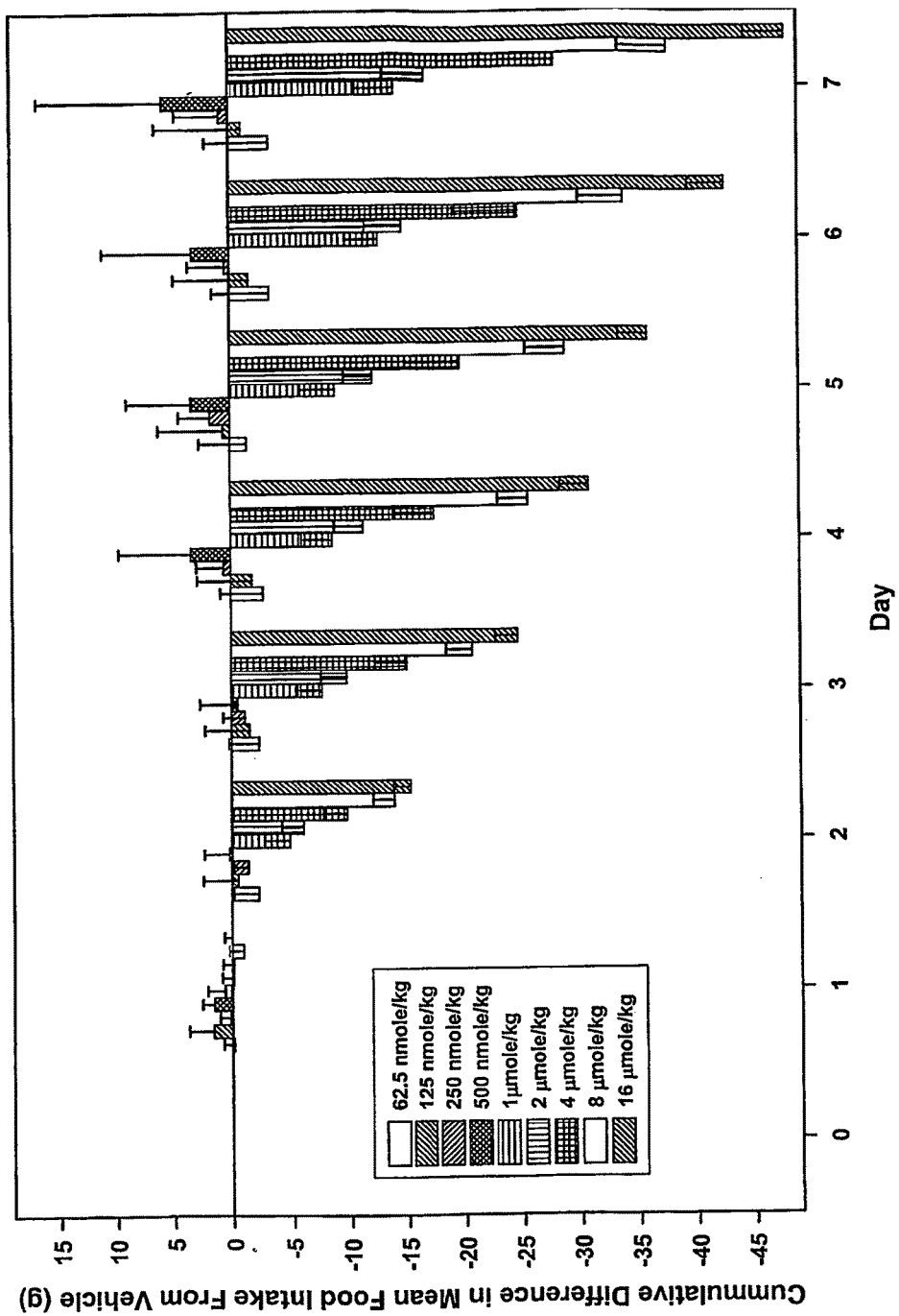
FIG. 2A. Cumulative difference in mean food intake from vehicle in rats after administration of various concentrations of Compound A.

The nomenclature used to define the peptides is that typically used in the art wherein the amino group at the N-terminus appears to the left and the carboxyl group at the C-terminus appears to the right. Where the amino acid has isomeric forms, it is the L form of the amino acid that is represented unless otherwise explicitly indicated. Unless defined otherwise, all technical and scientific terms used herein have the same meaning as commonly understood by one of ordinary skill in the art to which this invention belongs. Also, all publications, patent applications, patents and other references mentioned herein are incorporated by reference.

Nomenclature and Abbreviations

| Symbol | Meaning |
|---|---|
| Abu | α-aminobutyric acid |
| Ac | acyl group |
| Acc | 1-amino-1-cyclo($C_3$-$C_9$)alkyl carboxylic acid |
| A3c | 1-amino-1-cyclopropanecarboxylic acid |
| A4c | 1-amino-1-cyclobutanecarboxylic acid |
| A5c | 1-amino-1-cyclopentanecarboxylic acid |
| A6c | 1-amino-1-cyclohexanecarboxylic acid |
| Aha | 7-aminoheptanoic acid |
| Ahx | 6-aminohexanoic acid |
| Aib | α-aminoisobutyric acid |
| Ala or A | alanine |
| β-Ala | β-alanine |
| Apn | 5-aminopentanoic acid (HN—$(CH2)_4$—C(O) |
| Arg or R | arginine |
| hArg | homoarginine |
| Asn or N | asparagine |
| Asp or D | aspartic acid |
| Bal | 3-benzothienylalanine |
| Bip | 4,4'-biphenylalanine, represented by the structure 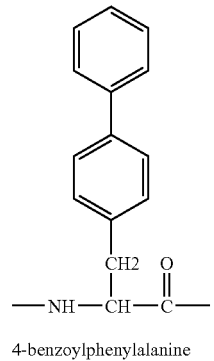 |
| Bpa | 4-benzoylphenylalanine |

| Symbol | Meaning |
|---|---|
| 4-Br-Phe | 4-bromo-phenylalanine |
| Cha | β-cyclohexylalanine |
| hCha | homo-cyclohexylalanine |
| Chg | cyclohexylglycine |
| Cys or C | cysteine |
| hCys | homocysteine |
| Dab | 2,4-diaminobutyric acid |
| Dap | 2,3-diaminopropionic acid |
| Dip | β,β-diphenylalanine |
| Doc | 8-amino-3,6-dioxaoctanoic acid with the structure of: |

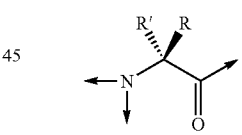

| | |
|---|---|
| 2-Fua | β-(2-furyl)-alanine |
| Gaba | 4-aminobutyric acid |
| Gln or Q | glutamine |
| Glu or E | glutamic acid |
| Gly or G | glycine |
| His or H | histidine |
| 3-Hyp | trans-3-hydroxy-L-proline, i.e., (2S,3S)-3-hydroxypyrrolidine-2-carboxylic acid |
| 4-Hyp | 4-hydroxyproline, i.e., (2S,4R)-4-hydroxypyrrolidine-2-carboxylic acid |
| Ile or I | isoleucine |
| Leu or L | leucine |
| hLeu | homoleucine |
| Lys or K | lysine |
| Met or M | methionine |
| β-hMet | β-homomethionine |
| 1-Nal | β-(1-naphthyl)alanine: |
| 2-Nal | β-(2-naphthyl)alanine |
| Nip | nipecotic acid |
| Nle | norleucine |
| Oic | octahydroindole-2-carboxylic acid |
| Orn | ornithine |
| 2-Pal | β-(2-pyridiyl)alanine |
| 3-Pal | β-(3-pyridiyl)alanine |
| 4-Pal | β-(4-pyridiyl)alanine |
| Pen | penicillamine |
| Phe or F | phenylalanine |
| hPhe | homophenylalanine |
| Pro or P | proline |
| hPro | homoproline |
| Ser or S | serine |
| Tle | tert-Leucine |
| Taz | β-(4-thiazolyl)alanine |
| 2-Thi | β-(2-thienyl)alanine |
| 3-Thi | β-(3-thienyl)alanine |
| Thr or T | threonine |
| Trp or W | tryptophan |
| Tyr or Y | tyrosine |
| D-(Et)Tyr | has a structure of |

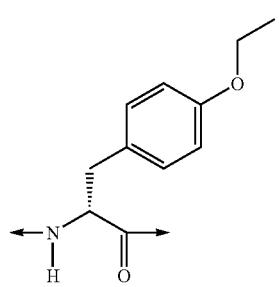

| | |
|---|---|
| Val or V | valine |

Certain other abbreviations used herein are defined as follows:
Boc: tert-butyloxycarbonyl
Bzl: benzyl
DCM: dichloromethane
DIC: N,N-diisopropylcarbodiimide
DIEA: diisopropylethyl amine
Dmab: 4-{N-(1-(4,4-dimethyl-2,6-dioxocyclohexylidene)-3-methylbutyl)-amino}benzyl
DMAP: 4-(dimethylamino)pyridine
DMF dimethylformamide
DNP: 2,4-dinitrophenyl
Fm: fluorenylmethyl
Fmoc: fluorenylmethyloxycarbonyl
For: formyl
HBTU: 2-(1H-benzotriazole-1-yl)-1,1,3,3-tetramethyluronium hexafluorophosphate
cHex cyclohexyl
HOAT: O-(7-azabenzotriazol-1-yl)-1,1,3,3-tetramethyluronium hexafluorophosphate
HOBt: 1-hydroxy-benzotriazole
MBHA 4-methylbenzhydrylamine
Mmt: 4-methoxytrityl
NMP: N-methylpyrrolidone
O-tBu oxy-tert-butyl
Pbf: 2,2,4,6,7-pentamethyldihydrobenzofuran-5-sulfonyl
PyBroP bromo-tris-pyrrolidino-phosphonium hexafluorophosphate
tBu: tert-butyl
TIS: triisopropylsilane
TOS: tosyl
Trt trityl
TFA: trifluoro acetic acid
TFFH: tetramethylfluoroforamidinium hexafluorophosphate
Z: benzyloxycarbonyl Unless otherwise indicated, with the exception of the N-terminal amino acid, all abbreviations (e.g. Ala) of amino acids in this disclosure stand for the structure of —NH—C(R)(R')—CO—, wherein R and R' each is, independently, hydrogen or the side chain of an amino acid (e.g., R=CH$_3$ and R'=H for Ala), or R and R' may be joined to form a ring system.

For the N-terminal amino acid, the abbreviation stands for the structure of:

The designation "NH$_2$" in e.g., Ac-Nle-c(Cys-D-Ala-His-D-Phe-Arg-Trp-Cys)-NH$_2$, indicates that the C-terminus of the peptide is amidated. Ac-Nle-c(Cys-D-Ala-His-D-Phe-Arg-Trp-Cys), or alternatively Ac-Nle-c(Cys-D-Ala-His-D-Phe-Arg-Trp-Cys)-OH, indicates that the C-terminus is the free acid.

"-c(Cys-Cys)-" or "-cyclo(Cys-Cys)-" denotes the structure:

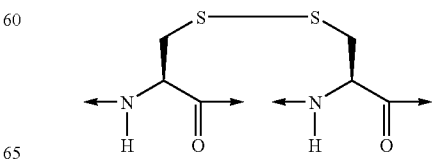

"-c(Cys-Pen)-" or "-cyclo(Cys-Pen)-" denotes the structure:

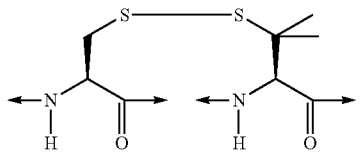

"-c(Asp-Lys)-" or "-cyclo(Asp-Lys)-" denotes the structure:

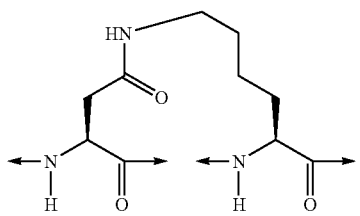

"Acyl" refers to R"-C(O)—, where R" is H, alkyl, substituted alkyl, heteroalkyl, substituted heteroalkyl, alkenyl, substituted alkenyl, aryl, alkylaryl, or substituted alkylaryl, and is indicated in the general formula of a particular embodiment as "Ac".

"Alkyl" refers to a hydrocarbon group containing one or more carbon atoms, where multiple carbon atoms if present are joined by single bonds. The alkyl hydrocarbon group may be straight-chain or contain one or more branches or cyclic groups.

"Hydroxyalkyl" refers to an alkyl group wherein one or more hydrogen atoms of the hydrocarbon group are substituted with one or more hydroxy radicals, such as hydroxymethyl, hydroxyethyl, hydroxypropyl, hydroxybutyl, hydroxypentyl, hydroxyhexyl and the like.

"Substituted alkyl" refers to an alkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, and —C$_{1-20}$ alkyl, wherein said —C$_{1-20}$ alkyl optionally may be substituted with one or more substituents selected, independently for each occurrence, from the group consisting of halogens, —CF$_3$, —OCH$_3$, —OCF$_3$, and —(CH$_2$)$_{0-20}$—COOH. In different embodiments 1, 2, 3 or 4 substituents are present. The presence of —(CH$_2$)$_{0-20}$—COOH results in the production of an alkyl acid. Non-limiting examples of alkyl acids containing, or consisting of, —(CH$_2$)$_{0-20}$—COOH include 2-norbornane acetic acid, tert-butyric acid, 3-cyclopentyl propionic acid, and the like.

The term "halo" encompasses fluoro, chloro, bromo and iodo.

"Heteroalkyl" refers to an alkyl wherein one of more of the carbon atoms in the hydrocarbon group is replaced with one or more of the following groups: amino, amido, —O—, —S— or carbonyl. In different embodiments 1 or 2 heteroatoms are present.

"Substituted heteroalkyl" refers to a heteroalkyl wherein one or more hydrogen atoms of the hydrocarbon group are replaced with one or more substituents selected from the group consisting of halogen, (i.e., fluorine, chlorine, bromine, and iodine), —OH, —CN, —SH, —NH$_2$, —NHCH$_3$, —NO$_2$, and —C$_{1-20}$ alkyl, wherein said —C$_{1-20}$ alkyl optionally may be substituted with one or more substituents selected, independently for each occurrence, from the group consisting of halogens, —CF$_3$, —OCH$_3$, —OCF$_3$, and —(CH$_2$)$_{0-20}$—COOH. In different embodiments 1, 2, 3 or 4 substituents are present.

"Alkenyl" refers to a hydrocarbon group made up of two or more carbons where one or more carbon-carbon double bonds are present. The alkenyl hydrocarbon group may be straight-chain or contain one or more branches or cyclic groups.

"Substituted alkenyl" refers to an alkenyl wherein one or more hydrogens are replaced with one or more substituents selected from the group consisting of halogen (i.e., fluorine, chlorine, bromine, and iodine), —OH, —CN, —SH, —NH$_2$, —NHCH$_3$, —NO$_2$, and —C$_{1-20}$ alkyl, wherein said —C$_{1-20}$ alkyl optionally may be substituted with one or more substituents selected, independently for each occurrence, from the group consisting of halogens, —CF$_3$, —OCH$_3$, —OCF$_3$, and —(CH$_2$)$_{0-20}$—COOH. In different embodiments 1, 2, 3 or 4 substituents are present.

"Aryl" refers to an optionally substituted aromatic group with at least one ring having a conjugated pi-electron system, containing up to three conjugated or fused ring systems. Aryl includes carbocyclic aryl, heterocyclic aryl and biaryl groups. Preferably, the aryl is a 5- or 6-membered ring. Preferred atoms for a heterocyclic aryl are one or more sulfur, oxygen, and/or nitrogen. Non-limiting examples of aryl include phenyl, 1-naphthyl, 2-naphthyl, indole, quinoline, 2-imidazole, 9-anthracene, and the like. Aryl substituents are selected from the group consisting of —C$_{1-20}$ alkyl, —C$_{1-20}$ alkoxy, halogen (i.e., fluorine, chlorine, bromine, and iodine), —OH, —CN, —SH, —NH$_2$, —NO$_2$, —C$_{1-20}$ alkyl substituted with halogens, —CF$_3$, —OCF$_3$, and —(CH$_2$)$_{0-20}$—COOH. In different embodiments the aryl contains 0, 1, 2, 3, or 4 substituents.

"Alkylaryl" refers to an "alkyl" joined to an "aryl".

The term "(C$_1$-C$_{12}$)hydrocarbon moiety" encompasses alkyl, alkenyl and alkynyl and in the case of alkenyl and alkynyl there is C$_2$-C$_{12}$.

As used herein, the term "normalizing" functions or activities refers to those types of functions which may be considered to be involved in normal body function or homeostasis of an organism. Such functions include but are not limited to activities and functions affecting body temperature, blood pressure, heart rate, vascular tone, brain blood flow, blood glucose levels and the like.

As used herein, compounds which are considered to be "selective" for a particular melanocortin receptor are those compounds with a functional activity characterized by an EC$_{50}$ at least about 2-fold, at least about 5-fold, at least about 10-fold, at least about 15-fold, at least about 17-fold, at least about 90-fold, at least about 200-fold, at least about 3000-fold or at least about 10,000-fold, or even greater, selectivity for any melanocortin receptor as compared to any other melanocortin receptor. For example, a selective melanocortin 4 receptor agonist of the invention exhibits a functional activity characterized by an EC$_{50}$ at least about 15-fold more selective for the human melanocortin 4 receptor than for the human melanocortin 1 receptor, the human melanocortin 3 receptor and the human melanocortin 5 receptor. Also for example, a selective melanocortin 4 receptor agonist of the invention exhibits a functional activity characterized by an EC$_{50}$ at least 17-fold more selective for the human melanocortin 4 receptor than for the human melanocortin 3 receptor.

Synthesis

The peptides of this invention can be prepared by standard solid phase peptide synthesis. See, e.g., Stewart, J. M., et al., Solid Phase Synthesis (Pierce Chemical Co., 2d ed. 1984). The substituents $R^2$ and $R^3$ of the above generic formula may be attached to the free amine of the N-terminal amino acid by standard methods known in the art. For example, alkyl groups, e.g., ($C_1$-$C_{30}$)alkyl, may be attached using reductive alkylation. Hydroxyalkyl groups, e.g., ($C_1$-$C_{30}$)hydroxyalkyl, may also be attached using reductive alkylation wherein the free hydroxyl group is protected with a t-butyl ester. Acyl groups, e.g., $COE^1$, may be attached by coupling the free acid, e.g., $E^1COOH$, to the free amine of the N-terminal amino acid by mixing the completed resin with 3 molar equivalents of both the free acid and diisopropylcarbodiimide in methylene chloride for one hour. If the free acid contains a free hydroxyl group, e.g., p-hydroxyphenylpropionic acid, then the coupling should be performed with an additional 3 molar equivalents of HOBt.

When $R^1$ is —$NH_2$, the synthesis of the peptide starts with an Fmoc-amino acid which is coupled to the Rink Amide MBHA resin. If $R^1$ is —OH, the synthesis of the peptide starts with a Fmoc-amino acid which is coupled to Wang resin.

In the synthesis of a peptide of this invention containing A6c and/or Aib, the coupling time is 2 hours for these residues and the residue immediately following them.

The following examples describe synthetic methods for making a peptide of this invention, which methods are well-known to those skilled in the art. Other methods are also known to those skilled in the art. The examples are provided for the purpose of illustration and are not meant to limit the scope of the present invention in any manner.

EXAMPLES

Example 1

Ac-Nle-c(Cys-D-Ala-His-D-Phe-Arg-Trp-Cys)-$NH_2$
SEQ ID NO:7

The title peptide was synthesized on an Advanced ChemTech model 396® multiple peptide synthesizer (Louisville, Ky. 40228) using Fluorenylmethyloxycarbonyl (Fmoc) chemistry. A Rink Amide 4-methylbenzylhydrylamine (MBHA) resin (Novabiochem®, San Diego, Calif.) with substitution of 0.58 mmol/g was used. The Fmoc amino acids (Novabiochem®, CA and Chem-Impex®, IL) used were Fmoc-Nle-OH, Fmoc-Cys(Trt)-OH, Fmoc-D-Ala-OH, Fmoc-His(Trt)-OH, Fmoc-D-Phe-OH, Fmoc-Arg(Pbf)-OH, and Fmoc-Trp(Boc)-OH. The synthesis was carried out on a 0.035 mmol scale. The Fmoc groups were removed by treatment with 25% piperidine in N,N-dimethylformamide (DMF) for 30 minutes. In each coupling step, the Fmoc amino acid (10 eq, 0.35 mmol), N,N-diisopropylcarbodiimide (DIC) (10 eq, 0.35 mmol), and 1-hydroxy-benzotriazole (HOBt) (10 eq, 0.35 mmol) were used in DMF (1.4 mL). After washing with DMF, double-coupling was performed with the Fmoc-amino acid (10 eq, 0.35 mmol), 2-(1-H-benzotriazole-1-yl)-1,1,2,3-tetramethyluronium hexafluorophosphate (HBTU) (8 eq, 0.28 mmol), HOBT (10 eq, 0.35 mmol), and diisopropylethyl amine (DIEA) (20 eq, 0.7 mmol) in DMF (1.26 mL). The ACT 396® multiple peptide synthesizer was programmed to perform the following reaction cycle: (1) washing with DMF, (2) removing Fmoc protecting group with 25% piperidine in DMF for 30 minutes, (3) washing with DMF, (4) coupling with Fmoc amino acid in the presence of DIC and HOBT for 1 hour, (5) washing with DMF, (6) double-coupling with the same Fmoc amino acid in step 4 in the presence of HBTU, HOBt, and DIEA for 1 hour. The resin was coupled successively according to the sequence of the title peptide. After the peptide chain was assembled and the last Fmoc-protecting group was removed, the resin was washed completely by using DMF and dichloromethane (DCM).

To cleave the title peptide, the resin was treated with a solution (1.5 mL) of TFA, $H_2O$ and triisopropylsilane (TIS) (v/v/v:90/6.2/3.8) for 2 hours at room temperature. The resin was filtered off and the filtrate was poured into 30 mL of ether. The precipitate was collected by centrifugation. This crude product was dissolved in water (~7 mL) and the pH of the aqueous solution was adjusted to ~7.5 by adding 2N $NH_4HCO_3$. The solution was opened to the air for 72 hours at room temperature. The resulting crude product was purified on a reverse-phase preparative HPLC system with a column (4×43 cm) of $C_{18}$ DYNAMAX-100® $A^0$ (Varian®, Walnut Creek, Calif.). The column was eluted over approximately 1 hour using a linear gradient of 85% A:15% B to 30% A:70% B, where A was 0.1% TFA in water and B was 0.1% TFA in acetonitrile. The fractions were checked by analytical HPLC and those containing pure product were pooled and lyophilized to dryness to give 10.3 mg (27% yield) of a white solid. Purity was assayed using HPLC and found to be approximately 88%. Electro-spray ionization mass spectrometry (ESI-MS) analysis gave the molecular weight at 1073.6 (in agreement with the calculated molecular weight of 1074.3).

Example 2

Ac-Cha-c(Asp-His-D-Phe-Arg-Trp-Gaba-Lys)-$NH_2$
SEQ ID NO:6

The title peptide was synthesized on an Applied Biosystems® (Foster City, Calif.) model 430A peptide synthesizer which was modified to do accelerated Boc-chemistry solid phase peptide synthesis. See Schnolzer, et al., Int. J. Peptide Protein Res., 40:180 (1992). 4-methylbenzhydrylamine (MBHA) resin (Peninsula®, Belmont, Calif.) with the substitution of 0.91 mmol/g was used. The Boc amino acids (Novabiochem®, San Diego, Calif. and Chem-Impex®, Wood Dale, Ill.) used were: Boc-Cha-OH, Boc-Asp(OFm)-OH, Boc-His(DNP)-OH, Boc-D-Phe-OH, Boc-Arg(Tos)-OH, Boc-Trp(For)-OH, Boc-Gaba-OH, and Boc-Lys(Fmoc)-OH. The synthesis was carried out on a 0.20 mmol scale. The Boc groups were removed by treatment with 100% TFA for 2×1 minute. Boc amino acids (2.5 mmol) were pre-activated with HBTU (2.0 mmol) and DIEA (1.0 mL) in 4 mL of DMF and were coupled without prior neutralization of the peptide-resin TFA salt. Coupling times were 5 minutes.

At the end of the assembly of Boc-Asp(OFm)-His(DNP)-D-Phe-Arg(Tos)-Trp(For)-Gaba-Lys(Fmoc)-MBHA, the peptide-resin was transferred into a reaction vessel on a shaker. The resin was treated twice with 25% piperidine in DMF for 15 minutes per session, washed with DMF, and shaken with bromo-tris-pyrrolidino-phosphonium hexafluorophosphate (PyBrOP) (6 eq, 0.3 mmol), DIEA (1 mL), and 4-(dimethylamino)pyridine (DMAP) (24 mg) in DMF (2 mL) for 12 hours. After washing with DMF, the resin was treated twice with 100% TFA for 2 minutes per treatment, washed with DMF and DCM, and then dried under reduced pressure. One fourth of the peptide-resin (0.05 mmol) was used for the next coupling with Boc-Cha-OH (10 eq, 0.5 mmol) in the presence of HBTU (9 eq, 0.45 mmol) and DIEA (0.25 mL) in DMF for 10 minutes. After the deprotection with 100% TFA in two sessions lasting approximately 2 minutes each, the peptide-resin was then washed with DMF. The final capping step was done by shaking the resin with acetic anhydride (40 eq, 2.0 mmol) and DIEA (20 eq, 1.0 mmol) in DMF for 1 hour. After washing with DMF, the resin was treated twice with a solution of 20% mercaptoethanol/10% DIEA in DMF, each treatment lasting approximately 30 minutes, to remove the DNP group on the Histidine side chain. The formyl group on the side chain of Tryptophan was removed by shaking with a solution of 15% ethanolamine/15% water/70% DMF twice for 30 minutes per shaking. The peptide-resin was washed with DMF and DCM and dried under reduced pressure. The final cleavage was done by stirring the peptide-resin in 10 mL of HF containing 1 mL of anisole and dithiothreitol (30 mg) at 0° C. for 75 minutes. HF was removed by a flow of nitrogen. The residue was washed with ether (6×10 mL) and extracted with 4N HOAc (6×10 mL).

The peptide mixture in the aqueous extract was purified on reverse-phase preparative high pressure liquid chromatography (HPLC) using a reverse phase VYDAC® $C_{18}$ column (Nest Group®, Southborough, Mass.). The column was eluted with a linear gradient (10% to 50% of solution B over 40 minutes) at a flow rate of 10 mL/minute (Solution A=water containing 0.1% TFA; Solution B=acetonitrile containing 0.1% of TFA). Fractions were collected and checked on analytical HPLC. Those containing pure product were combined and lyophilized to dryness. 5.1 mg of a white solid was obtained. Yield was 8.9%. Purity was 94.5% based on analytical HPLC analysis. Electro-spray mass spectrometer (MS (ES))S analysis gave the molecular weight at 1148.5 (in agreement with the calculated molecular weight of 1148.3).

Other peptides of the invention can be prepared by a person of ordinary skill in the art using synthetic procedures analogous to those disclosed generally hereinabove and/or to those disclosed specifically in the foregoing examples, as were the compounds depicted in Tables 1A and 1B.

Other peptides of the invention can be prepared by a person of ordinary skill in the art using synthetic procedures analogous to those disclosed generally hereinabove and/or to those disclosed specifically in the foregoing examples, as were the compounds depicted in Tables 1A and 1B.

The following examples can be made according to the appropriate procedures described above:

```
                                                          SEQ ID NO: 1
Ac-Nle-c(Asp-His-D-Phe-Arg-Trp-β-Ala-Lys)-NH2;

SEQ ID NO: 1
Ac-Nle-c(Asp-His-D-Phe-Arg-Trp-A6c-Lys)-NH2;

SEQ ID NO: 2
Ac-Nle-c(Cys-His-D-Phe-Arg-Trp-Ahx-Cys)-NH2;

SEQ ID NO: 3
D-Phe-c(Cys-His-D-Phe-Arg-Trp-Ala-D-Cys)-Thr-NH2;

SEQ ID NO: 3
D-Phe-c(Cys-His-D-Phe-Arg-Trp-β-Ala-D-Cys)-Thr-NH2;

SEQ ID NO: 3
D-Phe-c(Cys-His-D-Phe-Arg-Trp-Gaba-D-Cys)-Thr-NH2;

SEQ ID NO: 2
Ac-Nle-c(Cys-His-D-Phe-Arg-Trp-Apn-Cys)-NH2;

SEQ ID NO: 4
Ac-Nle-c(Asp-His-D-Phe-Arg-Trp-Apn-Lys)-NH2;

SEQ ID NO: 5
Ac-A6c-c(Asp-His-D-Phe-Arg-Trp-Gaba-Lys)-NH2;

SEQ ID NO: 6
Ac-D-2-Nal-c(Asp-His-D-Phe-Arg-Trp-Gaba-Lys)-NH2;

SEQ ID NO: 6
Ac-Nle-c(Asp-His-D-Phe-Arg-Trp-Gaba-Lys)-NH2;

SEQ ID NO: 7
Ac-Nle-c(Cys-(β-Ala-His-D-Phe-Arg-Trp-Cys)-NH2;

SEQ ID NO: 7
Ac-Nle-c(Cys-Gaba-His-D-Phe-Arg-Trp-Cys)-NH2;

SEQ ID NO: 7
Ac-Nle-c(Cys-Aib-His-D-Phe-Arg-Trp-Cys)-NH2;

SEQ ID NO: 7
Ac-Nle-c(Cys-Gly-His-D-Phe-Arg-Trp-Cys)-NH2;

SEQ ID NO: 8
Ac-Nle-c(D-Cys-Ala-His-D-Phe-Arg-Trp-Cys)-NH2;

SEQ ID NO: 8
Ac-Nle-c(D-Cys-D-Ala-His-D-Phe-Arg-Trp-Cys)-NH2;

SEQ ID NO: 8
Ac-Nle-c(D-Cys-β-Ala-His-D-Phe-Arg-Trp-Cys)-NH2;
```

-continued

Ac-Nle-c(D-Cys-Gaba-His-D-Phe-Arg-Trp-Cys)-NH$_2$;  SEQ ID NO: 8

Ac-Nle-c(D-Cys-Aib-His-D-Phe-Arg-Trp-Cys)-NH$_2$;  SEQ ID NO: 8

Ac-Nle-c(D-Cys-Gly-His-D-Phe-Arg-Trp-Cys)-NH$_2$;  SEQ ID NO: 8

Ac-Nle-c(Cys-D-Ala-His-D-Phe-Arg-Trp-D-Cys)-NH$_2$;  SEQ ID NO: 9

Ac-Nle-c(Cys-β-Ala-His-D-Phe-Arg-Trp-D-Cys)-NH$_2$;  SEQ ID NO: 9

Ac-Nle-c(Cys-Gaba-His-D-Phe-Arg-Trp-D-Cys)-NH$_2$;  SEQ ID NO: 9

Ac-Nle-c(Cys-Aib-His-D-Phe-Arg-Trp-D-Cys)-NH$_2$;  SEQ ID NO: 9

Ac-Nle-c(Cys-Gly-His-D-Phe-Arg-Trp-D-Cys)-NH$_2$;  SEQ ID NO: 9

Ac-Nle-c(D-Cys-Ala-His-D-Phe-Arg-Trp-D-Cys)-NH$_2$;  SEQ ID NO: 10

Ac-Nle-c(D-Cys-D-Ala-His-D-Phe-Arg-Trp-D-Cys)-NH$_2$;  SEQ ID NO: 10

Ac-Nle-c(D-Cys-β-Ala-His-D-Phe-Arg-Trp-D-Cys)-NH$_2$;  SEQ ID NO: 10

Ac-Nle-c(D-Cys-Gaba-His-D-Phe-Arg-Trp-D-Cys)-NH$_2$;  SEQ ID NO: 10

Ac-Nle-c(D-Cys-Aib-His-D-Phe-Arg-Trp-D-Cys)-NH$_2$;  SEQ ID NO: 10

Ac-Oic-c(Asp-His-D-Phe-Arg-Trp-Gaba-Lys)-NH$_2$;  SEQ ID NO: 11

Ac-Chg-c(Asp-His-D-Phe-Arg-Trp-Gaba-Lys)-NH$_2$;  SEQ ID NO: 11

Ac-hCha-c(Asp-His-D-Phe-Arg-Trp-Gaba-Lys)-NH$_2$;  SEQ ID NO: 11

Ac-D-Cha-c(Asp-His-D-Phe-Arg-Trp-Gaba-Lys)-NH$_2$;  SEQ ID NO: 11

Ac-Nip-c(Asp-His-D-Phe-Arg-Trp-Gaba-Lys)-NH$_2$;  SEQ ID NO: 11

Ac-hPro-c(Asp-His-D-Phe-Arg-Trp-Gaba-Lys)-NH$_2$;  SEQ ID NO: 11

Ac-hLeu-c(Asp-His-D-Phe-Arg-Trp-Gaba-Lys)-NH$_2$;  SEQ ID NO: 11

Ac-hCha-c(Asp-His-D-Phe-Arg-Trp-Gaba-Lys)-NH$_2$;  SEQ ID NO: 11

Ac-Phe-c(Asp-His-D-Phe-Arg-Trp-Gaba-Lys)-NH$_2$;  SEQ ID NO: 11

Ac-D-Phe-c(Asp-His-D-Phe-Arg-Trp-Gaba-Lys)-NH$_2$;  SEQ ID NO: 11

Ac-D-Chg-c(Asp-His-D-Phe-Arg-Trp-Gaba-Lys)-NH$_2$;  SEQ ID NO: 11 n-butanoyl-Cha-c(Asp-His-D-Phe-Arg-Trp-Gaba-Lys)-NH$_2$;  SEQ ID NO: 12

Ac-hPhe-c(Asp-His-D-Phe-Arg-Trp-Gaba-Lys)-NH$_2$;  SEQ ID NO: 11

Ac-β-hMet-c(Asp-His-D-Phe-Arg-Trp-Gaba-Lys)-NH$_2$;  SEQ ID NO: 11

-continued

```
                                                       SEQ ID NO: 11
Ac-Gaba-c(Asp-His-D-Phe-Arg-Trp-Gaba-Lys)-NH2;

SEQ ID NO: 13
Ac-Cha-c(Asp-His-D-Phe-Arg-D-Trp-Ala-Lys)-NH2;

SEQ ID NO: 13
Ac-hCha-c(Asp-His-D-Phe-Arg-D-Trp-Ala-Lys)-NH2;

SEQ ID NO: 13
Ac-Leu-c(Asp-His-D-Phe-Arg-D-Trp-Ala-Lys)-NH2;

SEQ ID NO: 13
Ac-hLeu-c(Asp-His-D-Phe-Arg-D-Trp-Ala-Lys)-NH2;

SEQ ID NO: 13
Ac-Phe-c(Asp-His-D-Phe-Arg-D-Trp-Ala-Lys)-NH2;

SEQ ID NO: 14
Ac-Nle-c(Asp-His-D-Phe-Arg-D-Trp-D-Ala-Lys)-NH2;

SEQ ID NO: 14
Ac-Nle-c(Asp-His-D-Phe-Arg-D-Trp-β-Ala-Lys)-NH2;

SEQ ID NO: 14
Ac-Nle-c(Asp-His-D-Phe-Arg-D-Trp-Gaba-Lys)-NH2;

SEQ ID NO: 14
Ac-Nle-c(Asp-His-D-Phe-Arg-D-Trp-Aha-Lys)-NH2;

SEQ ID NO: 14
Ac-Nle-c(Asp-His-D-Phe-Arg-D-Trp-Apn-Lys)-NH2;

SEQ ID NO: 15
Ac-Nle-c(Cys-His-D-Phe-Arg-D-Trp-Apn-Cys)-NH2;

SEQ ID NO: 15
Ac-Nle-c(Cys-His-D-Phe-Arg-D-Trp-Gaba-Cys)-NH2;

SEQ ID NO: 15
Ac-Nle-c(Cys-His-D-Phe-Arg-D-Trp-Ahx-Cys)-NH2;

SEQ ID NO: 15
Ac-Nle-c(Cys-His-D-Phe-Arg-D-Trp-β-Ala-Cys)-NH2;

SEQ ID NO: 15
Ac-Nle-c(Cys-His-D-Phe-Arg-D-Trp-D-Ala-Cys)-NH2;

SEQ ID NO: 16
Ac-Nle-c(Cys-D-Ala-His-D-2-Nal-Arg-Trp-Cys)-NH2;

SEQ ID NO: 16
Ac-Nle-c(Cys-D-Ala-His-D-2-Nal-Arg-2-Nal-Cys)-NH2;

SEQ ID NO: 16
Ac-Nle-c(Cys-D-Ala-His-D-2-Nal-Arg-1-Nal-Cys)-NH2;

SEQ ID NO: 17
n-butanoyl-Nle-c(Cys-D-Ala-His-D-Phe-Arg-2-Nal-Cys)-NH2;

SEQ ID NO: 17
n-butanoyl-Nle-c(Cys-D-Ala-His-D-Phe-Arg-Trp-Cys)-NH2;

SEQ ID NO: 18
Ac-Nle-c(Cys-D-Ala-His-D-Phe-Arg-2-Nal-Cys)-NH2;

SEQ ID NO: 18
Ac-Nle-c(Cys-D-Ala-His-D-Phe-Arg-1-Nal-Cys)-NH2;

SEQ ID NO: 18
Ac-Nle-c(Cys-D-Ala-His-D-Phe-Arg-Bal-Cys)-NH2;

SEQ ID NO: 61
Ac-Nle-c(Cys-D-Glu-His-D-Phe-Arg-Trp-Cys)-NH2;

SEQ ID NO: 19
Ac-Nle-c(Asp-His-D-Phe-Arg-Trp-D-Ala-Lys)-NH2;

SEQ ID NO: 20
Ac-Nle-c(Cys-D-Ala-His-D-2-Nal-Arg-Bal-Cys)-NH2;
```

-continued

```
                                                   SEQ ID NO: 21
Ac-Nle-c(Pen-D-Ala-His-D-Phe-Arg-Trp-Cys)-NH2;

SEQ ID NO: 22
Ac-Nle-c(Cys-D-Ala-His-D-Phe-Arg-Trp-Pen)-NH2;

SEQ ID NO: 22
Ac-Nle-c(Pen-D-Ala-His-D-Phe-Arg-Trp-Pen)-NH2;

SEQ ID NO: 23
D-Phe-c(Cys-His-D-Phe-hArg-Trp-β-Ala-D-Cys)-Thr-NH2;

SEQ ID NO: 24
D-Phe-c(Cys-His-D-(Et)Tyr-Arg-Trp-β-Ala-D-Cys)-Thr-NH2;

SEQ ID NO: 25
D-Phe-c(Cys-His-D-Phe-Arg-Bip-β-Ala-D-Cys)-Thr-NH2;

SEQ ID NO: 24
D-Phe-c(Cys-His-D-(Et)Tyr-hArg-Trp-β-Ala-D-Cys)-Thr-NH2;

SEQ ID NO: 26
D-Phe-c(Cys-His-D-Phe-hArg-Bip-β-Ala-D-Cys)-Thr-NH2;

SEQ ID NO: 26
D-Phe-c(Cys-His-D-(Et)Tyr-hArg-Bip-β-Ala-D-Cys)-Thr-NH2;

SEQ ID NO: 54
Ac-Nle-c(Cys-D-Ala-His-D-Phe-Arg-Trp-Gly-Cys)-NH2;

SEQ ID NO: 54
Ac-Nle-c(Cys-D-Ala-His-D-Phe-Arg-Trp-D-Ala-Cys)-NH2;

SEQ ID NO: 54
Ac-Nle-c(Cys-D-Ala-His-D-Phe-Arg-Trp-β-Ala-Cys)-NH2;

SEQ ID NO: 54
Ac-Nle-c(Cys-D-Ala-His-D-Phe-Arg-Trp-Gaba-Cys)-NH2;

SEQ ID NO: 54
Ac-Nle-c(Cys-D-Ala-His-D-Phe-Arg-Trp-Apn-Cys)-NH2;

SEQ ID NO: 27
Nle-c(Cys-His-D-Phe-Arg-Trp-Apn-Cys)-NH2;

SEQ ID NO: 28
Ac-Nle-c(Asp-D-Ala-His-D-Phe-Arg-Trp-Lys)-NH2;

SEQ ID NO: 28
Ac-Nle-c(Asp-D-Ala-His-D-Phe-Arg-Bal-Lys)-NH2;

SEQ ID NO: 55
Ac-c(Cys-Glu-His-D-Phe-Arg-Trp-Ala-Cys)-NH2;

SEQ ID NO: 55
Ac-c(Cys-Glu-His-D-Phe-Arg-2-Nal-Ala-Cys)-NH2;

SEQ ID NO: 56
Ac-c(Cys-D-Ala-His-D-Phe-Arg-Trp-Ala-Cys)-NH2;

SEQ ID NO: 56
Ac-c(Cys-D-Ala-His-D-Phe-Arg-2-Nal-Ala-Cys)-NH2;

SEQ ID NO: 57
Ac-Nle-c(Cys-D-Ala-His-D-Phe-Arg-Trp-Ala-Cys)-NH2;

SEQ ID NO: 57
Ac-Nle-c(Cys-D-Ala-His-D-Phe-Arg-Trp-β-Ala-Cys)-NH2;

SEQ ID NO: 57
Ac-Nle-c(Cys-D-Ala-His-D-Phe-Arg-Trp-Gaba-Cys)-NH2;

SEQ ID NO: 29
Ac-Nle-c(Cys-D-Ala-His-D-Phe-Arg-Trp-Pen)-OH;

SEQ ID NO: 30
Ac-Nle-c(Cys-D-Abu-His-D-Phe-Arg-Trp-Cys)-NH2;

SEQ ID NO: 30
Ac-Nle-c(Cys-D-Val-His-D-Phe-Arg-Trp-Cys)-NH2;
```

-continued

| Sequence | SEQ ID NO |
|---|---|
| Ac-Nle-c(Cys-D-Ile-His-D-Phe-Arg-Trp-Cys)-NH₂; | SEQ ID NO: 30 |
| Ac-Nle-c(Cys-D-Leu-His-D-Phe-Arg-Trp-Cys)-NH₂; | SEQ ID NO: 30 |
| Ac-Nle-c(Cys-D-Tle-His-D-Phe-Arg-Trp-Cys)-NH₂; | SEQ ID NO: 30 |
| Ac-Nle-c(Cys-D-Cha-His-D-Phe-Arg-Trp-Cys)-NH₂; | SEQ ID NO: 30 |
| Ac-Nle-c(Pen-His-D-Phe-Arg-Trp-Gaba-Cys)-NH₂; | SEQ ID NO: 31 |
| Ac-Nle-c(Cys-His-D-Phe-Arg-Trp-Gaba-Pen)-NH₂; | SEQ ID NO: 32 |
| Ac-Nle-c(Pen-His-D-Phe-Arg-Trp-Gaba-Pen)-NH₂; | SEQ ID NO: 32 |
| Ac-Leu-c(Cys-His-D-Phe-Arg-Trp-Gaba-Cys)-NH₂; | SEQ ID NO: 33 |
| Ac-Cha-c(Cys-His-D-Phe-Arg-Trp-Gaba-Cys)-NH₂; | SEQ ID NO: 33 |
| Ac-Ile-c(Cys-His-D-Phe-Arg-Trp-Gaba-Cys)-NH₂; | SEQ ID NO: 33 |
| Ac-Phe-c(Cys-His-D-Phe-Arg-Trp-Gaba-Cys)-NH₂; | SEQ ID NO: 33 |
| Ac-Val-c(Cys-His-D-Phe-Arg-Trp-Gaba-Cys)-NH₂; | SEQ ID NO: 33 |
| Ac-2-Nal-c(Cys-His-D-Phe-Arg-Trp-Gaba-Cys)-NH₂; | SEQ ID NO: 33 |
| Nle-c(Cys-His-D-Phe-Arg-Trp-Gaba-Cys)-NH₂; | SEQ ID NO: 34 |
| Phe-c(Cys-His-D-Phe-Arg-Trp-Gaba-Cys)-NH₂; | SEQ ID NO: 34 |
| Ac-Nle-c(Cys-3-Pal-D-Phe-Arg-Trp-Gaba-Cys)-NH₂; | SEQ ID NO: 35 |
| Ac-Nle-c(Cys-D-Ala-His-D-Phe-Arg-Trp-Cys)-OH; | SEQ ID NO: 36 |
| Ac-Nle-c(Cys-His-Phe-Arg-D-Trp-Gaba-Cys)-NH₂; | SEQ ID NO: 37 |
| Ac-Nle-c(Asp-D-Ala-His-D-Phe-Arg-Bal-Ala-Lys)-NH₂; | SEQ ID NO: 58 |
| Ac-Nle-c(Asp-His-D-2-Nal-Arg-Trp-Ala-Lys)-NH₂; | SEQ ID NO: 38 |
| Ac-Nle-c(Asp-His-D-2-Nal-Arg-Trp-β-Ala-Lys)-NH₂; | SEQ ID NO: 38 |
| Ac-Nle-c(Cys-His-D-2-Nal-Arg-Trp-Gaba-Cys)-NH₂; | SEQ ID NO: 39 |
| Ac-Nle-c(Cys-His-D-2-Nal-Arg-Trp-Ahx-Cys)-NH₂; | SEQ ID NO: 39 |
| Ac-hPhe-c(Asp-His-D-2-Nal-Arg-Trp-Gaba-Lys)-NH₂; | SEQ ID NO: 40 |
| Ac-Cha-c(Asp-His-D-2-Nal-Arg-Trp-Gaba-Lys)-NH₂; | SEQ ID NO: 40 |
| Ac-Nle-c(Asp-His-D-Phe-Arg-Trp-β-Ala-Lys)-OH; | SEQ ID NO: 41 |
| Ac-Nle-c(Cys-His-D-Phe-Arg-Trp-Ahx-Cys)-OH; | SEQ ID NO: 42 |

-continued

D-Phe-c(Cys-His-D-Phe-Arg-Trp-Ala-D-Cys)-Thr-OH;  SEQ ID NO: 43

D-Phe-c(Cys-His-D-Phe-Arg-Trp-β-Ala-D-Cys)-Thr-OH;  SEQ ID NO: 43

D-Phe-c(Cys-His-D-Phe-Arg-Trp-Gaba-D-Cys)-Thr-OH;  SEQ ID NO: 43

Ac-Nle-c(Cys-His-D-Phe-Arg-Trp-Apn-Cys)-OH;  SEQ ID NO: 42

Ac-Nle-c(Asp-His-D-Phe-Arg-Trp-Apn-Lys)-OH;  SEQ ID NO: 41

Ac-Cha-c(Asp-His-D-Phe-Arg-Trp-Gaba-Lys)-OH;  SEQ ID NO: 44

Ac-Nle-c(Asp-His-D-Phe-Arg-Trp-Gaba-Lys)-OH;  SEQ ID NO: 44

Ac-Nle-c(Cys-D-Ala-His-D-Phe-Arg-Trp-Cys)-OH;  SEQ ID NO: 29

Ac-Chg-c(Asp-His-D-Phe-Arg-Trp-Gaba-Lys)-OH;  SEQ ID NO: 44

Ac-D-Cha-c(Asp-His-D-Phe-Arg-Trp-Gaba-Lys)-OH;  SEQ ID NO: 44

Ac-hCha-c(Asp-His-D-Phe-Arg-Trp-Gaba-Lys)-OH;  SEQ ID NO: 44

Ac-D-Chg-c(Asp-His-D-Phe-Arg-Trp-Gaba-Lys)-OH;  SEQ ID NO: 44

Ac-hPhe-c(Asp-His-D-Phe-Arg-Trp-Gaba-Lys)-OH;  SEQ ID NO: 44

Ac-Nle-c(Cys-His-D-Phe-Arg-D-Trp-Gaba-Cys)-OH;  SEQ ID NO: 45

Ac-Nle-c(Cys-His-D-Phe-Arg-D-Trp-Ahx-Cys)-OH;  SEQ ID NO: 45

Ac-Nle-c(Cys-His-D-Phe-Arg-D-Trp-β-Ala-Cys)-OH;  SEQ ID NO: 45

Ac-Nle-c(Cys-His-D-Phe-Arg-D-Trp-D-Ala-Cys)-OH;  SEQ ID NO: 45

Ac-Nle-c(Cys-D-Ala-His-D-2-Nal-Arg-Trp-Cys)-OH;  SEQ ID NO: 46

Ac-Nle-c(Cys-D-Ala-His-D-2-Nal-Arg-2-Nal-Cys)-OH;  SEQ ID NO: 46

Ac-Nle-c(Cys-D-Ala-His-D-2-Nal-Arg-1-Nal-Cys)-OH;  SEQ ID NO: 46

Ac-Nle-c(Cys-D-Ala-His-D-2-Nal-Arg-Bal-Cys)-OH;  SEQ ID NO: 46

Ac-Nle-c(Pen-D-Ala-His-D-Phe-Arg-Trp-Cys)-OH;  SEQ ID NO: 47

Ac-Nle-c(Cys-D-Ala-His-D-Phe-Arg-Trp-Pen)-OH;  SEQ ID NO: 29

Ac-Arg-c(Cys-D-Ala-His-D-Phe-Arg-Trp-Cys)-NH$_2$;  SEQ ID NO: 50

Ac-D-Arg-c(Cys-D-Ala-His-D-Phe-Arg-Trp-Cys)-NH$_2$;  SEQ ID NO: 50

Ac-D-Arg-c(Cys-D-Ala-His-D-Phe-Arg-Trp-Pen)-NH$_2$;  SEQ ID NO: 51

Ac-D-Arg-c(Cys-His-D-Phe-Arg-Trp-Gaba-Pen)-NH$_2$;  SEQ ID NO: 52

-continued

```
Ac-Arg-c(Cys-His-D-Phe-Arg-Trp-Gaba-Pen)-NH₂;                           SEQ ID NO: 52

Ac-Arg-c(Cys-D-Ala-His-D-Phe-Arg-Trp-Pen)-NH₂;                          SEQ ID NO: 51

Ac-D-Arg-c(Asp-His-D-Phe-Arg-Trp-Ala-Lys)-NH₂;                          SEQ ID NO: 53

Ac-Arg-c(Asp-His-D-Phe-Arg-Trp-Ala-Lys)-NH₂;                            SEQ ID NO: 53

Ac-Arg-c(Cys-D-Ala-His-D-2-Nal-Arg-Trp-Cys)-NH₂;                        SEQ ID NO: 49
and Ac-Nle-c(Cys-His-D-Phe-Arg-Trp-Gaba-Pen)-OH.                            SEQ ID NO: 48
```

Other peptides of the invention can be prepared by a person of ordinary skill in the art using synthetic procedures analogous to those disclosed generally hereinabove and/or to those disclosed specifically in the foregoing examples, as were the compounds depicted in Tables 1A and 1B.

Tables 1A and 1B—Molecular Weight and Purity for Selected Embodiments

TABLE 1A

| Compound | Calculated Molecular Weight | Experimental Molecular Weight | Purity | SEQ ID NO: |
|---|---|---|---|---|
| Ac-Nle-c(Asp-His-D-Phe-Trp-β-Ala-Lys)-NH₂ | 1095.27 | 1095.2 | 96.4 | SEQ ID NO: 1 |
| Ac-Nle-c(Asp-His-D-Phe-Trp-A6c-Lys)-NH₂ | 1149.36 | 1149.05 | 96 | SEQ ID NO: 1 |
| Ac-Nle-c(Cys-His-D-Phe-Arg-Trp-Ahx-Cys)-NH₂ | 1116.38 | 1115.8 | 98 | SEQ ID NO: 2 |
| D-Phe-c(Cys-His-D-Phe-Arg-Trp-Ala-D-Cys)-Thr-NH₂ | 1167.38 | 1167.3 | 99 | SEQ ID NO: 3 |
| D-Phe-c(Cys-His-D-Phe-Arg-Trp-β-Ala-D-Cys)-Thr-NH₂ | 1167.38 | 1167.5 | 93 | SEQ ID NO: 3 |
| D-Phe-c(Cys-His-D-Phe-Arg-Trp-Gaba-D-Cys)-Thr-NH₂ | 1181.41 | 1181.9 | 99 | SEQ ID NO: 3 |
| Ac-Nle-c(Cys-His-D-Phe-Arg-Trp-Apn-Cys)-NH₂ | 1102.35 | 1103 | 99 | SEQ ID NO: 2 |
| Ac-Nle-c(Asp-His-D-Phe-Arg-Trp-Apn-Lys)-NH₂ | 1123.32 | 1123.9 | 99 | SEQ ID NO: 4 |
| Ac-A6c-c(Asp-His-D-Phe-Arg-Trp-Gaba-Lys)-NH₂ | 1121.31 | 1121.2 | 93 | SEQ ID NO: 5 |
| Ac-D-2-Nal-c(Asp-His-D-Phe-Arg-Trp-Gaba-Lys)-NH₂ | 1193.37 | 1193.2 | 92.6 | SEQ ID NO: 6 |
| Ac-Cha-c(Asp-His-D-Phe-Arg-Trp-Gaba-Lys)-NH₂; | 1149.36 | 1149.4 | 94.5 | SEQ ID NO: 6 |
| Ac-Nle-c(Asp-His-D-Phe-Arg-Trp-Gaba-Lys)-NH₂ | 1109.3 | 1109.2 | 91.5 | SEQ ID NO: 6 |
| Ac-Nle-c(Cys-D-Ala-His-D-Phe-Arg-Trp-Cys)-NH₂ | 1074.3 | 1074.6 | 98.3 | SEQ ID NO: 7 |
| Ac-Nle-c(Cys-β-Ala-His-D-Phe-Arg-Trp-Cys)-NH₂ | 1074.3 | 1074.4 | 91 | SEQ ID NO: 7 |
| Ac-Nle-c(Cys-Gaba-His-D-Phe-Arg-Trp-Cys)-NH₂ | 1088.32 | 1088.4 | 93 | SEQ ID NO: 7 |

TABLE 1A-continued

| Compound | Calculated Molecular Weight | Experimental Molecular Weight | Purity | SEQ ID NO: |
|---|---|---|---|---|
| Ac-Nle-c(Cys-Aib-His-D-Phe-Arg-Trp-Cys)-NH$_2$ | 1088.32 | 1088.4 | 80 | SEQ ID NO: 7 |
| Ac-Nle-c(Cys-Gly-His-D-Phe-Arg-Trp-Cys)-NH$_2$ | 1060.27 | 1060.4 | 90 | SEQ ID NO: 7 |
| Ac-Nle-c(D-Cys-Ala-His-D-Phe-Arg-Trp-Cys)-NH$_2$ | 1074.3 | 1074.4 | 93 | SEQ ID NO: 8 |
| Ac-Nle-c(D-Cys-D-Ala-His-D-Phe-Arg-Trp-Cys)-NH$_2$ | 1074.3 | 1074.4 | 81 | SEQ ID NO: 8 |
| Ac-Nle-c(D-Cys-β-Ala-His-D-Phe-Arg-Trp-Cys)-NH$_2$ | 1074.3 | 1074.4 | 92 | SEQ ID NO: 8 |
| Ac-Nle-c(D-Cys-Gaba-His-D-Phe-Arg-Trp-Cys)-NH$_2$ | 1088.32 | 1088.4 | 94 | SEQ ID NO: 8 |
| Ac-Nle-c(D-Cys-Aib-His-D-Phe-Arg-Trp-Cys)-NH$_2$ | 1088.32 | 1088.4 | 91 | SEQ ID NO: 8 |
| Ac-Nle-c(D-Cys-Gly-His-D-Phe-Arg-Trp-Cys)-NH$_2$ | 1060.27 | 1060.4 | 96 | SEQ ID NO: 8 |
| Ac-Nle-c(Cys-D-Ala-His-D-Phe-Arg-Trp-D-Cys)-NH$_2$ | 1074.3 | 1074.4 | 66 | SEQ ID NO: 9 |
| Ac-Nle-c(Cys-β-Ala-His-D-Phe-Arg-Trp-D-Cys)-NH$_2$ | 1074.3 | 1074.2 | 94 | SEQ ID NO: 9 |
| Ac-Nle-c(Cys-Gaba-His-D-Phe-Arg-Trp-D-Cys)-NH$_2$ | 1088.32 | 1088.2 | 93 | SEQ ID NO: 9 |
| Ac-Nle-c(Cys-Aib-His-D-Phe-Arg-Trp-D-Cys)-NH$_2$ | 1088.32 | 1088.4 | 90 | SEQ ID NO: 9 |
| Ac-Nle-c(Cys-Gly-His-D-Phe-Arg-Trp-D-Cys)-NH$_2$ | 1060.27 | 1060.4 | 91 | SEQ ID NO: 9 |
| Ac-Nle-c(D-Cys-Ala-His-D-Phe-Arg-Trp-D-Cys)-NH$_2$ | 1074.3 | 1074.4 | 65 | SEQ ID NO: 10 |
| Ac-Nle-c(D-Cys-D-Ala-His-D-Phe-Arg-Trp-D-Cys)-NH$_2$ | 1074.3 | 1074.2 | 93 | SEQ ID NO: 10 |
| Ac-Nle-c(D-Cys-β-Ala-His-D-Phe-Arg-Trp-D-Cys)-NH$_2$ | 1074.3 | 1074.4 | 92 | SEQ ID NO: 10 |
| Ac-Nle-c(D-Cys-Gaba-His-D-Phe-Arg-Trp-D-Cys)-NH$_2$ | 1088.32 | 1088.4 | 90 | SEQ ID NO: 10 |
| Ac-Nle-c(D-Cys-Aib-His-D-Phe-Arg-Trp-D-Cys)-NH$_2$ | 1088.32 | 1088 | 95 | SEQ ID NO: 10 |
| Ac-Oic-c(Asp-His-D-Phe-Arg-Trp-Gaba-Lys)-NH$_2$ | 1147.35 | 1147.4 | 97.5 | SEQ ID NO: 11 |
| Ac-Chg-c(Asp-His-D-Phe-Arg-Trp-Gaba-Lys)-NH$_2$ | 1135.33 | 1135.1 | 99 | SEQ ID NO: 11 |
| Ac-hCha-c(Asp-His-D-Phe-Arg-Trp-Gaba-Lys)-NH$_2$ | 1163.39 | 1163.4 | 99 | SEQ ID NO: 11 |
| Ac-D-Cha-c(Asp-His-D-Phe-Arg-Trp-Gaba-Lys)-NH$_2$ | 1149.36 | 1149.2 | 99 | SEQ ID NO: 11 |
| Ac-Nip-c(Asp-His-D-Phe-Arg-Trp-Gaba-Lys)-NH$_2$ | 1107.28 | 1107 | 98.9 | SEQ ID NO: 11 |
| Ac-hPro-c(Asp-His-D-Phe-Arg-Trp-Gaba-Lys)-NH$_2$ | 1107.28 | 1107.4 | 99 | SEQ ID NO: 11 |
| Ac-hLeu-c(Asp-His-D-Phe-Arg-Trp-Gaba-Lys)-NH$_2$ | 1123.32 | 1123.2 | 99 | SEQ ID NO: 11 |

TABLE 1A-continued

| Compound | Calculated Molecular Weight | Experimental Molecular Weight | Purity | SEQ ID NO: |
|---|---|---|---|---|
| Ac-D-hCha-c(Asp-His-D-Phe-Arg-Trp-Gaba-Lys)-NH$_2$ | 1163.39 | 1163.6 | 94 | SEQ ID NO: 59 |
| Ac-Phe-c(Asp-His-D-Phe-Arg-Trp-Gaba-Lys)-NH$_2$ | 1143.31 | 1143.3 | 96.9 | SEQ ID NO: 11 |
| Ac-D-Phe-c(Asp-His-D-Phe-Arg-Trp-Gaba-Lys)-NH$_2$ | 1143.31 | 1143.3 | 96.5 | SEQ ID NO: 11 |
| Ac-D-Chg-c(Asp-His-D-Phe-Arg-Trp-Gaba-Lys)-NH$_2$ | 1135.33 | 1135.4 | 99 | SEQ ID NO: 11 |
| n-Butyryl-Cha-c(Asp-His-D-Phe-Arg-Trp-Gaba-Lys)-NH$_2$ | 1177.41 | 1177.5 | 88.6 | SEQ ID NO: 60 |
| Ac-hPhe-c(Asp-His-D-Phe-Arg-Trp-Gaba-Lys)-NH$_2$ | 1157.34 | 1157.2 | 70 | SEQ ID NO: 11 |
| Ac-β-hMet-c(Asp-His-D-Phe-Arg-Trp-Gaba-Lys)-NH$_2$ | 1141.36 | 1141.2 | 89 | SEQ ID NO: 11 |
| Ac-Gaba-c(Asp-His-D-Phe-Arg-Trp-Gaba-Lys)-NH$_2$ | 1081.24 | 1080.9 | 92.5 | SEQ ID NO: 11 |
| Ac-Cha-c(Asp-His-D-Phe-Arg-D-Trp-Ala-Lys)-NH$_2$ | 1135.33 | 1135.2 | 85 | SEQ ID NO: 13 |
| Ac-hCha-c(Asp-His-D-Phe-Arg-D-Trp-Ala-Lys)-NH$_2$ | 1149.36 | 1149.1 | 87 | SEQ ID NO: 13 |
| Ac-Leu-c(Asp-His-D-Phe-Arg-D-Trp-Ala-Lys)-NH$_2$ | 1095.27 | 1095.4 | 98.6 | SEQ ID NO: 13 |
| Ac-hLeu-c(Asp-His-D-Phe-Arg-D-Trp-Ala-Lys)-NH$_2$ | 1109.3 | 1109.2 | 93.8 | SEQ ID NO: 13 |
| Ac-Phe-c(Asp-His-D-Phe-Arg-D-Trp-Ala-Lys)-NH$_2$ | 1129.29 | 1129.2 | 81.9 | SEQ ID NO: 13 |
| Ac-Nle-c(Asp-His-D-Phe-Arg-D-Trp-D-Ala-Lys)-NH$_2$ | 1095.27 | 1095.3 | 97 | SEQ ID NO: 14 |
| Ac-Nle-c(Asp-His-D-Phe-Arg-D-Trp-β-Ala-Lys)-NH$_2$ | 1095.27 | 1095.3 | 82 | SEQ ID NO: 14 |
| Ac-Nle-c(Asp-His-D-Phe-Arg-D-Trp-Gaba-Lys)-NH$_2$ | 1109.3 | 1109.1 | 99 | SEQ ID NO: 14 |
| Ac-Nle-c(Asp-His-D-Phe-Arg-D-Trp-Aha-Lys)-NH$_2$ | 1137.35 | 1137.4 | 98 | SEQ ID NO: 14 |
| Ac-Nle-c(Asp-His-D-Phe-Arg-D-Trp-Apn-Lys)-NH$_2$ | 1123.32 | 1123.3 | 97.3 | SEQ ID NO: 14 |
| Ac-Nle-c(Cys-His-D-Phe-Arg-D-Trp-Apn-Cys)-NH$_2$ | 1102.35 | 1102 | 99 | SEQ ID NO: 15 |
| Ac-Nle-c(Cys-His-D-Phe-Arg-D-Trp-Gaba-Cys)-NH$_2$ | 1088.32 | 1087.8 | 97 | SEQ ID NO: 15 |
| Ac-Nle-c(Cys-His-D-Phe-Arg-D-Trp-Ahx-Cys)-NH$_2$ | 1116.38 | 1116.2 | 99 | SEQ ID NO: 15 |
| Ac-Nle-c(Cys-His-D-Phe-Arg-D-Trp-β-Ala-Cys)-NH$_2$ | 1074.3 | 1073.8 | 99.9 | SEQ ID NO: 15 |
| Ac-Nle-c(Cys-His-D-Phe-Arg-D-Trp-D-Ala-Cys)-NH$_2$ | 1074.3 | 1073.8 | 99.9 | SEQ ID NO: 15 |
| Ac-Nle-c(Cys-D-Ala-His-D-2-Nal-Arg-Trp-Cys)-NH$_2$ | 1124.36 | 1123.6 | 96.1 | SEQ ID NO: 16 |
| Ac-Nle-c(Cys-D-Ala-His-D-2-Nal-Arg-2-Nal-Cys)-NH$_2$ | 1135.38 | 1134.5 | 99.1 | SEQ ID NO: 16 |

TABLE 1A-continued

| Compound | Calculated Molecular Weight | Experimental Molecular Weight | Purity | SEQ ID NO: |
|---|---|---|---|---|
| Ac-Nle-c(Cys-D-Ala-His-D-2-Nal-Arg-1-Nal-Cys)-NH$_2$ | 1135.38 | 1134.6 | 94.8 | SEQ ID NO: 16 |
| nButanoyl-Nle-c(Cys-D-Ala-His-D-Phe-Arg-2-Nal-Cys)-NH$_2$ | 1113.37 | 1112.6 | 95.7 | SEQ ID NO: 17 |
| nButanoyl-Nle-c(Cys-D-Ala-His-D-Phe-Arg-Trp-Cys)-NH$_2$ | 1102.35 | 1101.5 | 99.9 | SEQ ID NO: 17 |
| Ac-Nle-c(Cys-D-Ala-His-D-Phe-Arg-2-Nal-Cys)-NH$_2$ | 1085.32 | 1084.4 | 97.7 | SEQ ID NO: 18 |
| Ac-Nle-c(Cys-D-Ala-His-D-Phe-Arg-1-Nal-Cys)-NH$_2$ | 1085.32 | 1084.5 | 96.6 | SEQ ID NO: 18 |
| Ac-Nle-c(Cys-D-Ala-His-D-Phe-Arg-Bal-Cys)-NH$_2$ | 1091.35 | 1090.4 | 96.2 | SEQ ID NO: 18 |
| Ac-Nle-c(Cys-D-Glu-His-D-Phe-Arg-Trp-Cys)-NH$_2$ | 1132.33 | 1131.5 | 99.9 | SEQ ID NO: 61 |
| Ac-Nle-c(Asp-His-D-Phe-Arg-Trp-D-Ala-Lys)-NH$_2$ | 1095.27 | 1094.6 | 99.9 | SEQ ID NO: 19 |
| Ac-Nle-c(Cys-D-Ala-His-D-2-Nal-Arg-Bal-Cys)-NH$_2$ | 1141.41 | 1140.5 | 95.6 | SEQ ID NO: 20 |
| Ac-Nle-c(Pen-D-Ala-His-D-Phe-Arg-Trp-Cys)-NH$_2$ | 1102.35 | 1101.6 | 99.9 | SEQ ID NO: 21 |
| Ac-Nle-c(Cys-D-Ala-His-D-Phe-Arg-Trp-Pen)-NH$_2$ | 1102.35 | 1101.6 | 99.9 | SEQ ID NO: 22 |
| Ac-Nle-c(Pen-D-Ala-His-D-Phe-Arg-Trp-Pen)-NH$_2$ | 1130.4 | 1129.6 | 99.9 | SEQ ID NO: 22 |
| D-Phe-c(Cys-His-D-Phe-hArg-Trp-β-Ala-D-Cys)-Thr-NH$_2$ | 1181.41 | 1181.7 | 96.9 | SEQ ID NO: 23 |
| D-Phe-c(Cys-His-D-(Et)Tyr-Arg-Trp-β-Ala-D-Cys)-Thr-NH$_2$ | 1211.43 | 1211.7 | 97.1 | SEQ ID NO: 24 |
| D-Phe-c(Cys-His-D-Phe-Arg-Bip-β-Ala-D-Cys)-Thr-NH$_2$ | 1204.44 | 1204.6 | 99 | SEQ ID NO: 25 |
| D-Phe-c(Cys-His-D-(Et)Tyr-hArg-Trp-β-Ala-D-Cys)-Thr-NH$_2$ | 1225.46 | 1225.7 | 97 | SEQ ID NO: 24 |
| D-Phe-c(Cys-His-D-Phe-hArg-Bip-β-Ala-D-Cys)-Thr-NH$_2$ | 1218.47 | 1218.8 | 99 | SEQ ID NO: 26 |
| D-Phe-c(Cys-His-D-(Et)Tyr-hArg-Bip-β-Ala-D-Cys)-Thr-NH$_2$ | 1262.52 | 1263 | 99 | SEQ ID NO: 26 |
| Ac-Nle-c(Cys-D-Ala-His-D-Phe-Arg-Trp-Gly-Cys)-NH$_2$ | 1131.35 | 1131.2 | 96.8 | SEQ ID NO: 54 |
| Ac-Nle-c(Cys-D-Ala-His-D-Phe-Arg-Trp-D-Ala-Cys)-NH$_2$ | 1145.37 | 1145.3 | 96.4 | SEQ ID NO: 54 |
| Ac-Nle-c(Cys-D-Ala-His-D-Phe-Arg-Trp-β-Ala-Cys)-NH$_2$ | 1145.37 | 1145.2 | 98.2 | SEQ ID NO: 54 |
| Ac-Nle-c(Cys-D-Ala-His-D-Phe-Arg-Trp-Gaba-Cys)-NH$_2$ | 1159.4 | 1159.2 | 95.1 | SEQ ID NO: 54 |
| Ac-Nle-c(Cys-D-Ala-His-D-Phe-Arg-Trp-Apn-Cys)-NH$_2$ | 1173.43 | 1173.3 | 96.8 | SEQ ID NO: 54 |
| Nle-c(Cys-His-D-Phe-Arg-Trp-Apn-Cys)-NH$_2$ | 1060.31 | 1060.3 | 98.5 | SEQ ID NO: 27 |
| Ac-Nle-c(Asp-D-Ala-His-D-Phe-Arg-Trp-Lys)-NH$_2$ | 1095.27 | 1094.7 | 96.2 | SEQ ID NO: 28 |

TABLE 1A-continued

| Compound | Calculated Molecular Weight | Experimental Molecular Weight | Purity | SEQ ID NO: |
|---|---|---|---|---|
| Ac-Nle-c(Asp-D-Ala-His-D-Phe-Arg-Bal-Lys)-NH$_2$ | 1112.32 | 1111.7 | 96.5 | SEQ ID NO: 28 |
| Ac-c(Cys-Glu-His-D-Phe-Arg-Trp-Ala-Cys)-NH$_2$ | 1090.25 | 1089.6 | 99.9 | SEQ ID NO: 55 |
| Ac-c(Cys-Glu-His-D-Phe-Arg-2-Nal-Ala-Cys)-NH$_2$ | 1101.27 | 1100.6 | 98.3 | SEQ ID NO: 55 |
| Ac-c(Cys-D-Ala-His-D-Phe-Arg-Trp-Ala-Cys)-NH$_2$ | 1032.22 | 1031.5 | 95.2 | SEQ ID NO: 56 |
| Ac-c(Cys-D-Ala-His-D-Phe-Arg-2-Nal-Ala-Cys)-NH$_2$ | 1043.24 | 1042.5 | 95.6 | SEQ ID NO: 56 |
| Ac-Nle-c(Cys-D-Ala-His-D-Phe-Arg-Trp-Ala-Cys)-NH$_2$ | 1144.39 | 1144.6 | 95.3 | SEQ ID NO: 57 |
| Ac-Nle-c(Cys-D-Ala-His-D-Phe-Arg-Trp-β-Ala-Cys)-NH$_2$ | 1145.37 | 1144.6 | 97.3 | SEQ ID NO: 57 |
| Ac-Nle-c(Cys-D-Ala-His-D-Phe-Arg-Trp-Gaba-Cys)-NH$_2$ | 1158.41 | 1158.6 | 96.5 | SEQ ID NO: 57 |
| Ac-Nle-c(Cys-D-Ala-His-D-Phe-Arg-Trp-Pen)-OH | 1103.33 | 1103 | 99.9 | SEQ ID NO: 29 |
| Ac-Nle-c(Cys-D-Abu-His-D-Phe-Arg-Trp-Cys)-NH$_2$ | 1088.32 | 1087.6 | 99.9 | SEQ ID NO: 30 |
| Ac-Nle-c(Cys-D-Val-His-D-Phe-Arg-Trp-Cys)-NH$_2$ | 1102.35 | 1101.7 | 99.9 | SEQ ID NO: 30 |
| Ac-Nle-c(Cys-D-Ile-His-D-Phe-Arg-Trp-Cys)-NH$_2$ | 1116.38 | 1115.7 | 99.9 | SEQ ID NO: 30 |
| Ac-Nle-c(Cys-D-Leu-His-D-Phe-Arg-Trp-Cys)-NH$_2$ | 1116.38 | 1115.8 | 97.4 | SEQ ID NO: 30 |
| Ac-Nle-c(Cys-D-Tle-His-D-Phe-Arg-Trp-Cys)-NH$_2$ | 1116.38 | 1115.5 | 96.5 | SEQ ID NO: 30 |
| Ac-Nle-c(Cys-D-Cha-His-D-Phe-Arg-Trp-Cys)-NH$_2$ | 1156.44 | 1155.6 | 96.4 | SEQ ID NO: 30 |
| Ac-Nle-c(Pen-His-D-Phe-Arg-Trp-Gaba-Cys)-NH$_2$ | 1116.38 | 1115.7 | 95 | SEQ ID NO: 31 |
| Ac-Nle-c(Cys-His-D-Phe-Arg-Trp-Gaba-Pen)-NH$_2$ | 1116.38 | 1115.5 | 99.9 | SEQ ID NO: 32 |
| Ac-Nle-c(Pen-His-D-Phe-Arg-Trp-Gaba-Pen)-NH$_2$ | 1144.43 | 1144 | 99.9 | SEQ ID NO: 32 |
| Ac-Leu-c(Cys-His-D-Phe-Arg-Trp-Gaba-Cys)-NH$_2$ | 1088.32 | 1088 | 96.7 | SEQ ID NO: 33 |
| Ac-Cha-c(Cys-His-D-Phe-Arg-Trp-Gaba-Cys)-NH$_2$ | 1128.39 | 1128.4 | 95.8 | SEQ ID NO: 33 |
| Ac-Ile-c(Cys-His-D-Phe-Arg-Trp-Gaba-Cys)-NH$_2$ | 1088.32 | 1088.4 | 95 | SEQ ID NO: 33 |
| Ac-Phe-c(Cys-His-D-Phe-Arg-Trp-Gaba-Cys)-NH$_2$ | 1122.34 | 1122 | 95.2 | SEQ ID NO: 33 |
| Ac-Val-c(Cys-His-D-Phe-Arg-Trp-Gaba-Cys)-NH$_2$ | 1074.3 | 1074.6 | 95.4 | SEQ ID NO: 33 |
| Ac-2-Nal-c(Cys-His-D-Phe-Arg-Trp-Gaba-Cys)-NH$_2$ | 1172.4 | 1172.2 | 95.2 | SEQ ID NO: 33 |
| Nle-c(Cys-His-D-Phe-Arg-Trp-Gaba-Cys)-NH$_2$ | 1046.29 | 1046.4 | 97.6 | SEQ ID NO: 34 |

TABLE 1A-continued

| Compound | Calculated Molecular Weight | Experimental Molecular Weight | Purity | SEQ ID NO: |
|---|---|---|---|---|
| Phe-c(Cys-His-D-Phe-Arg-Trp-Gaba-Cys)-NH$_2$ | 1080.3 | 1080 | 95.8 | SEQ ID NO: 34 |
| Ac-Nle-c(Cys-3-Pal-D-Phe-Arg-Trp-Gaba-Cys)-NH$_2$ | 1099.35 | 1099.6 | 96.6 | SEQ ID NO: 35 |
| Ac-Nle-c(Cys-D-Ala-His-D-Phe-Arg-Trp-Cys)-OH | 1075.28 | 1075.2 | 99.9 | SEQ ID NO: 36 |
| Ac-Nle-c(Cys-His-Phe-Arg-D-Trp-Gaba-Cys)-NH$_2$ | 1088.32 | 1088 | 95.8 | SEQ ID NO: 37 |
| Ac-Nle-c(Asp-D-Ala-His-D-Phe-Arg-Bal-Ala-Lys)-NH$_2$ | 1183.4 | 1182.85 | 99.9 | SEQ ID NO: 58 |
| Ac-Nle-c(Asp-His-D-2-Nal-Arg-Trp-Ala-Lys)-NH$_2$ | 1145.33 | 1145 | 99.99 | SEQ ID NO: 38 |
| Ac-Nle-c(Asp-His-D-2-Nal-Arg-Trp-βAla-Lys)-NH$_2$ | 1145.33 | 1145 | 99.99 | SEQ ID NO: 38 |
| Ac-Nle-c(Cys-His-D-2-Nal-Arg-Trp-Gaba-Cys)-NH$_2$ | 1138.38 | 1137.8 | 99.99 | SEQ ID NO: 39 |
| Ac-Nle-c(Cys-His-D-2-Nal-Arg-Trp-Ahx-Cys)-NH$_2$ | 1166.44 | 1166 | 99 | SEQ ID NO: 39 |
| Ac-hPhe-c(Asp-His-D-2-Nal-Arg-Trp-Gaba-Lys)-NH$_2$ | 1207.4 | 1206.9 | 99 | SEQ ID NO: 40 |
| Ac-Cha-c(Asp-His-D-2-Nal-Arg-Trp-Gaba-Lys)-NH$_2$ | 1199.42 | 1198.8 | 100 | SEQ ID NO: 40 |
| Ac-Arg-c(Cys-D-Ala-His-D-Phe-Arg-Trp-Cys)-NH$_2$ | 1117.3 | 1116.9 | 95.10 | SEQ ID NO: 50 |
| Ac-D-Arg-c(Cys-D-Ala-His-D-Phe-Arg-Trp-Cys)-NH$_2$ | 1117.33 | 1116.8 | 99.2 | SEQ ID NO: 50 |
| Ac-D-Arg-c(Cys-D-Ala-His-D-Phe-Arg-Trp-Pen)-NH$_2$ | 1145.38 | 1144.9 | 96.4 | SEQ ID NO: 51 |
| Ac-D-Arg-c(Cys-His-D-Phe-Arg-Trp-Gaba-Pen)-NH$_2$ | 1159.41 | 1158.9 | 99.9 | SEQ ID NO: 52 |
| Ac-Arg-c(Cys-His-D-Phe-Arg-Trp-Gaba-Pen)-NH$_2$ | 1159.41 | 1159.1 | 99 | SEQ ID NO: 52 |
| Ac-Arg-c(Cys-D-Ala-His-D-Phe-Arg-Trp-Pen)-NH$_2$ | 1145.38 | 1145.1 | 99 | SEQ ID NO: 51 |
| Ac-D-Arg-c(Asp-His-D-Phe-Arg-Trp-Ala-Lys)-NH$_2$ | 1138.3 | 1138.0 | 98.0 | SEQ ID NO: 53 |
| Ac-Arg-c(Asp-His-D-Phe-Arg-Trp-Ala-Lys)-NH$_2$ | 1138.3 | 1138.1 | 99.0 | SEQ ID NO: 53 |

TABLE 1B

| Compound | Calculated Molecular Weight | Experimental Molecular Weight | Purity | SEQ ID NO: |
|---|---|---|---|---|
| Ac-Arg-c(Cys-D-Ala-His-D-2-Nal-Arg-Trp-Cys)-NH$_2$ | 1167.39 | 1167.40 | 99.9 | SEQ ID NO: 49 |

Example 3

In vitro Studies

Compounds of the present invention can be and were tested for activity as ligands of one or more of the melanocortin receptors according to the following procedures. One skilled in the art would know that procedures similar to those described herein may be used to assay the binding activities of the compounds of the invention to melanocortin receptor molecules.

Radioligand Binding Assays

Cellular membranes used for the in vitro receptor binding assays were obtained from transgenic CHO-K1 cells stably expressing hMC-R receptor subtypes 1, 3, 4 or 5. The CHO-K1 cells expressing the desired hMC-R receptor type were sonicated (Branson® setting 7, approximately 30 sec) in ice-cold 50 mM Tris-HCl at pH 7.4 and then centrifuged at 39,000 g for 10 minutes at approximately 4° C. The pellets were resuspended in the same buffer and centrifuged at 50,000 g for 10 minutes at approximately 4° C. The washed pellets containing the cellular membranes were stored at approximately −80° C.

Competitive inhibition of $[^{125}I](Tyr^2)$—$(Nle^4$-D-Phe$^7)\alpha$-MSH ($[^{125}I]$-NDP-$\alpha$-MSH, Amersham Biosciences®) binding was carried out in polypropylene 96 well plates. Cell membranes (1-10 µg protein/well) prepared as described above were incubated in 50 mM Tris-HCl at pH 7.4 containing 0.2% bovine serum albumin (BSA), 5 mM MgCl$_2$, 1 mM CaCl$_2$ and 0.1 mg/mL bacitracin, with increasing concentrations of the test compound and 0.1-0.3 nM $[^{125}I]$-NDP-$\alpha$-MSH for approximately 90-120 minutes at approximately 37° C. Bound $[^{125}I]$-NDP-$\alpha$-MSH ligand was separated from free $[^{125}I]$-NDP-$\alpha$-MSH by filtration through GF/C glass fiber filter plates (Unifilter®; Packard) presoaked with 0.1% (w/v) polyethylenimine (PEI), using a Packard Filtermate® harvester. Filters were washed three times with 50 mM Tris-HCl at pH 7.4 at a temperature of approximately 0-4° C. and then assayed for radioactivity using a Packard Topcount® scintillation counter. Binding data were analyzed by computer-assisted non-linear regression analysis (XL fit; IDBS).

A selection of the preferred embodiments was tested using the above-discussed assay and the binding constants (Ki in nM) are reported in Tables 2A, 2B and 2C.

TABLES 2A, 2B and 2C—Radioligand Binding Assay Data for Selected Compounds

TABLE 2A

| Compound | Ki hMC1-R | Ki hMC3-R | Ki hMC4-R | Ki hMC5-R | Ki hMC1-R/ MC4-R | SEQ ID NO: |
|---|---|---|---|---|---|---|
| Ac-Arg-c(Cys-D-Ala-His-D-Phe-Arg-Trp-Cys)-NH$_2$ | 3.87 | 10.1 | 2.09 | 430 | 1.9 | SEQ ID NO: 50 |
| Ac-D-Arg-c(Cys-D-Ala-His-D-Phe-Arg-Trp-Cys)-NH$_2$ | 4.01 | 12.1 | 1.76 | 352 | 2.3 | SEQ ID NO: 50 |
| Ac-D-Arg-c(Cys-D-Ala-His-D-Phe-Arg-Trp-Pen)-NH$_2$ | 8.29 | 13.3 | 2.78 | 816 | 3.0 | SEQ ID NO: 51 |
| Ac-D-Arg-c(Cys-His-D-Phe-Arg-Trp-Gaba-Pen)-NH$_2$ | 3.93 | 172 | 11.0 | 538 | 0.36 | SEQ ID NO: 52 |
| Ac-Arg-c(Cys-His-D-Phe-Arg-Trp-Gaba-Pen)-NH$_2$ | 1.81 | 20.5 | 4.57 | 502 | 0.4 | SEQ ID NO: 52 |
| Ac-Arg-c(Cys-D-Ala-His-D-Phe-Arg-Trp-Pen)-NH$_2$ | 9.67 | 22.0 | 4.2 | 1900 | 2.3 | SEQ ID NO: 51 |
| Ac-D-Arg-c(Asp-His-D-Phe-Arg-Trp-Ala-Lys)-NH$_2$ | 0.79 | 45.5 | 1.21 | 493 | 0.6 | SEQ ID NO: 53 |
| Ac-Arg-c(Asp-His-D-Phe-Arg-Trp-Ala-Lys)-NH$_2$ | 0.68 | 20.7 | 1.01 | 783 | 0.7 | SEQ ID NO: 53 |

TABLE 2B

| Compound | Ki hMC1-R | Ki hMC3-R | Ki hMC4-R | Ki hMC5-R | Ki hMC1-R/ MC4-R | SEQ ID NO: |
|---|---|---|---|---|---|---|
| Ac-Nle-c(Cys-D-Ala-His-D-2-Nal-Arg-1-Nal-Cys)-NH$_2$ | 114 | 63.9 | 3.07 | 1657 | 37.1 | SEQ ID NO: 16 |
| Ac-Nle-c(Cys-D-Ala-His-D-Phe-Arg-Trp-Cys)-NH$_2$ | 11 | 26 | 7.6 | 1800 | 1.4 | SEQ ID NO: 7 |
| D-Phe-c(Cys-His-D-(Et)Tyr-Arg-Trp-β-Ala-D-Cys)-Thr-NH$_2$ | 0.05 | 9.3 | 1.1 | 2.9 | 0.0 | SEQ ID NO: 24 |
| Nle-c(Cys-His-D-Phe-Arg-Trp-Apn-Cys)-NH$_2$ | 0.07 | 4.1 | 0.85 | 8.8 | 0.1 | SEQ ID NO: 27 |

TABLE 2B-continued

| Compound | Ki hMC1-R | Ki hMC3-R | Ki hMC4-R | Ki hMC5-R | Ki hMC1-R/MC4-R | SEQ ID NO: |
|---|---|---|---|---|---|---|
| Ac-Nle-c(Cys-His-D-Phe-Arg-Trp-Gaba-Pen)-NH$_2$ | 0.12 | 10 | 0.43 | 0.42 | 0.3 | SEQ ID NO: 32 |
| Nle-c(Cys-His-D-Phe-Arg-Trp-Gaba-Cys)-NH$_2$ | 0.05 | 1.3 | 0.47 | 0.2 | 0.1 | SEQ ID NO: 34 |
| Ac-Nle-c(Asp-His-D-Phe-Arg-Trp-β-Ala-Lys)-NH$_2$ | 0.0996 | 9318 | 0.617 | 10.9 | 0.16 | SEQ ID NO: 1 |
| Ac-Nle-c(Cys-His-D-Phe-Arg-Trp-Ahx-Cys)-NH$_2$ | .0132 | 16.1 | 1.23 | 0.359 | 0.11 | SEQ ID NO: 2 |
| D-Phe-c(Cys-His-D-Phe-Arg-Trp-β-Ala-D-Cys)-Thr-NH$_2$ | 0.207 | 43.2 | 2.58 | 344 | 0.08 | SEQ ID NO: 3 |
| D-Phe-c(Cys-His-D-Phe-Arg-Trp-Gaba-D-Cys)-Thr-NH$_2$ | 0.420 | 106 | 4.75 | 1260 | 0.09 | SEQ ID NO: 3 |
| Ac-Nle-c(Cys-His-D-Phe-Arg-Trp-Apn-Cys)-NH$_2$ | 0.0951 | 9.33 | 0.894 | 13.4 | 0.11 | SEQ ID NO: 2 |
| Ac-Nle-c(Asp-His-D-Phe-Arg-Trp-Apn-Lys)-NH$_2$ | 0.999 | 300 | 11.1 | 431 | 0.09 | SEQ ID NO: 4 |
| Ac-Cha-c(Asp-His-D-Phe-Arg-Trp-Gaba-Lys)-NH$_2$ | 0.106 | 11.8 | 1.49 | 110 | 0.07 | SEQ ID NO: 6 |
| Ac-Nle-c(Asp-His-D-Phe-Arg-Trp-Gaba-Lys)-NH$_2$ | 0.0506 | 9.89 | 1.04 | 16.3 | 0.05 | SEQ ID NO: 6 |
| Ac-Chg-c(Asp-His-D-Phe-Arg-Trp-Gaba-Lys)-NH$_2$ | 0.884 | 223 | 22.5 | 609 | 0.04 | SEQ ID NO: 11 |
| Ac-hCha-c(Asp-His-D-Phe-Arg-Trp-Gaba-Lys)-NH$_2$ | 0.721 | 93.5 | 56.0 | 747 | 0.01 | SEQ ID NO: 11 |
| Ac-D-Chg-c(Asp-His-D-Phe-Arg-Trp-Gaba-Lys)-NH$_2$ | 0.227 | 14.5 | 2.99 | 164 | 0.08 | SEQ ID NO: 11 |
| Ac-hPhe-c(Asp-His-D-Phe-Arg-Trp-Gaba-Lys)-NH$_2$ | 0.277 | 25.2 | 3.37 | 203 | 0.08 | SEQ ID NO: 11 |
| Ac-Nle-c(Cys-His-D-Phe-Arg-D-Trp-β-Ala-Cys)-NH$_2$ | 0.323 | 14.1 | 1.96 | 24.0 | 0.16 | SEQ ID NO: 15 |
| Ac-Nle-c(Pen-D-Ala-His-D-Phe-Arg-Trp-Cys)-NH$_2$ | 34.1 | 118 | 17.0 | 5560 | 2.01 | SEQ ID NO: 21 |
| Ac-Nle-c(Cys-D-Ala-His-D-Phe-Arg-Trp-Pen)-NH$_2$ | 29.1 | 22.8 | 3.84 | 2550 | 7.58 | SEQ ID NO: 22 |
| D-Phe-c(Cys-His-D-Phe-hArg-Trp-β-Ala-D-Cys)-Thr-NH$_2$ | 0.442 | 123 | 10.3 | 521 | 0.04 | SEQ ID NO: 23 |
| D-Phe-c(Cys-His-D-Phe-Arg-Bip-β-Ala-D-Cys)-Thr-NH$_2$ | 5.80 | 3370 | 583 | 1130 | 0.01 | SEQ ID NO: 25 |
| D-Phe-c(Cys-His-D-(Et)Tyr-hArg-Trp-β-Ala-D-Cys)-Thr-NH$_2$ | 0.0567 | 31.4 | 14.7 | 9.27 | 0 | SEQ ID NO: 24 |
| D-Phe-c(Cys-His-D-Phe-hArg-Bip-β-Ala-D-Cys)-Thr-NH$_2$ | 1.68 | 1260 | 172 | 1220 | 0.01 | SEQ ID NO: 26 |
| D-Phe-c(Cys-His-D-(Et)Tyr-hArg-Bip-β-Ala-D-Cys)-Thr-NH$_2$ | 0.128 | 85.6 | 36.9 | 38.0 | 0 | SEQ ID NO: 26 |
| Ac-Nle-c(Cys-D-Ala-His-D-Phe-Arg-Trp-Gly-Cys)-NH$_2$ | 0.352 | 149 | 3.01 | 339 | 0.12 | SEQ ID NO: 54 |
| Ac-Nle-c(Cys-D-Ala-His-D-Phe-Arg-Trp-D-Ala-Cys)-NH$_2$ | 3.93 | 876 | 48.0 | 4940 | 0.08 | SEQ ID NO: 54 |

TABLE 2B-continued

| Compound | Ki hMC1-R | Ki hMC3-R | Ki hMC4-R | Ki hMC5-R | Ki hMC1-R/ MC4-R | SEQ ID NO: |
|---|---|---|---|---|---|---|
| Ac-Nle-c(Cys-D-Ala-His-D-Phe-Arg-Trp-β-Ala-Cys)-NH$_2$ | 0.995 | 287 | 4.80 | 766 | 0.21 | SEQ ID NO: 54 |
| Ac-Nle-c(Cys-D-Ala-His-D-Phe-Arg-Trp-Gaba-Cys)-NH$_2$ | 0.848 | 184 | 3.76 | 956 | 0.23 | SEQ ID NO: 54 |
| Ac-Nle-c(Cys-D-Ala-His-D-Phe-Arg-Trp-Apn-Cys)-NH$_2$ | 1.10 | 228 | 7.58 | 859 | 0.15 | SEQ ID NO: 54 |
| Ac-Nle-c(Asp-D-Ala-His-D-Phe-Arg-Trp-Lys)-NH$_2$ | 0.659 | 98.9 | 2.55 | 4.19 | 0.26 | SEQ ID NO: 28 |
| Ac-Nle-c(Asp-D-Ala-His-D-Phe-Arg-Bal-Lys)-NH$_2$ | 4.12 | 445 | 50.6 | 4300 | 0.08 | SEQ ID NO: 28 |
| Ac-c(Cys-Glu-His-D-Phe-Arg-Trp-Ala-Cys)-NH$_2$ | 111 | 1710 | 47.7 | 694 | 2.33 | SEQ ID NO: 55 |
| Ac-c(Cys-Glu-His-D-Phe-Arg-2-Nal-Ala-Cys)-NH$_2$ | 262 | 2500 | 96.4 | 1460 | 2.72 | SEQ ID NO: 55 |
| Ac-c(Cys-D-Ala-His-D-Phe-Arg-Trp-Ala-Cys)-NH$_2$ | 199 | 5990 | 96.7 | >10000 | 2.06 | SEQ ID NO: 56 |
| Ac-c(Cys-D-Ala-His-D-Phe-Arg-2-Nal-Ala-Cys)-NH$_2$ | 132 | 4560 | 40.7 | 8810 | 3.24 | SEQ ID NO: 56 |
| Ac-Nle-c(Cys-D-Ala-His-D-Phe-Arg-Trp-Ala-Cys)-NH$_2$ | 9.12 | 1130 | 22.1 | 2860 | 0.41 | SEQ ID NO: 57 |
| Ac-Nle-c(Cys-D-Ala-His-D-Phe-Arg-Trp-β-Ala-Cys)-NH$_2$ | 1.00 | 227 | 5.55 | 496 | 0.18 | SEQ ID NO: 57 |
| Ac-Nle-c(Cys-D-Ala-His-D-Phe-Arg-Trp-Gaba-Cys)-NH$_2$ | 0.536 | 169 | 3.12 | 358 | 0.17 | SEQ ID NO: 57 |
| Ac-Nle-c(Cys-D-Ala-His-D-Phe-Arg-Trp-Pen)-OH | 32.1 | 330 | 17.4 | 165 | 1.84 | SEQ ID NO: 29 |
| Ac-Nle-c(Cys-D-Abu-His-D-Phe-Arg-Trp-Cys)-NH$_2$ | 10.6 | 41.1 | 7.69 | 54.9 | 1.38 | SEQ ID NO: 30 |
| Ac-Nle-c(Cys-D-Val-His-D-Phe-Arg-Trp-Cys)-NH$_2$ | 13.0 | 104 | 10.1 | 40 | 1.29 | SEQ ID NO: 30 |
| Ac-Nle-c(Cys-D-Ile-His-D-Phe-Arg-Trp-Cys)-NH$_2$ | 4.28 | 38.5 | 9.0 | 12.5 | 0.48 | SEQ ID NO: 30 |
| Ac-Nle-c(Cys-D-Leu-His-D-Phe-Arg-Trp-Cys)-NH$_2$ | 1.60 | 6.82 | 4.13 | 5.57 | 0.39 | SEQ ID NO: 30 |
| Ac-Nle-c(Cys-D-Tle-His-D-Phe-Arg-Trp-Cys)-NH$_2$ | 12.0 | 85.8 | 11.2 | 40 | 1.07 | SEQ ID NO: 30 |
| Ac-Nle-c(Cys-D-Cha-His-D-Phe-Arg-Trp-Cys)-NH$_2$ | 0.353 | 2.08 | 1.41 | 0.857 | 0.25 | SEQ ID NO: 30 |
| Ac-Nle-c(Pen-His-D-Phe-Arg-Trp-Gaba-Cys)-NH$_2$ | 0.537 | 86.1 | 5.89 | 2.56 | 0.09 | SEQ ID NO: 31 |
| Ac-Nle-c(Pen-His-D-Phe-Arg-Trp-Gaba-Pen)-NH$_2$ | 0.744 | 178 | 3.51 | 2.69 | 0.21 | SEQ ID NO: 32 |
| Ac-Leu-c(Cys-His-D-Phe-Arg-Trp-Gaba-Cys)-NH$_2$ | 0.216 | 17.4 | 0.995 | 0.486 | 0.22 | SEQ ID NO: 33 |
| Ac-Cha-c(Cys-His-D-Phe-Arg-Trp-Gaba-Cys)-NH$_2$ | 0.107 | 9.11 | 0.884 | 0.354 | 0.12 | SEQ ID NO: 33 |
| Ac-Ile-c(Cys-His-D-Phe-Arg-Trp-Gaba-Cys)-NH$_2$ | 0.148 | 13.9 | 1.06 | 0.423 | 0.14 | SEQ ID NO: 33 |
| Ac-Phe-c(Cys-His-D-Phe-Arg-Trp-Gaba-Cys)-NH$_2$ | 0.254 | 18.5 | 2.13 | 0.714 | 0.12 | SEQ ID NO: 33 |

TABLE 2B-continued

| Compound | Ki hMC1-R | Ki hMC3-R | Ki hMC4-R | Ki hMC5-R | Ki hMC1-R/ MC4-R | SEQ ID NO: |
|---|---|---|---|---|---|---|
| Ac-Val-c(Cys-His-D-Phe-Arg-Trp-Gaba-Cys)-NH$_2$ | 0.256 | 29.9 | 1.98 | 0.864 | 0.13 | SEQ ID NO: 33 |
| Ac-2-Nal-c(Cys-His-D-Phe-Arg-Trp-Gaba-Cys)-NH$_2$ | 0.560 | 39.2 | 2.94 | 2.73 | 0.19 | SEQ ID NO: 33 |
| Phe-c(Cys-His-D-Phe-Arg-Trp-Gaba-Cys)-NH$_2$ | 0.186 | 15.2 | 4.93 | 0:537 | 0.04 | SEQ ID NO: 34 |
| Ac-Nle-c(Cys-3-Pal-D-Phe-Arg-Trp-Gaba-Cys)-NH$_2$ | 21.1 | 151 | 10.4 | 92.6 | 2.03 | SEQ ID NO: 35 |
| Ac-Nle-c(Cys-D-Ala-His-D-Phe-Arg-Trp-Cys)-OH | 30.7 | 152 | 15.6 | 114 | 1.97 | SEQ ID NO: 36 |
| Ac-Nle-c(Cys-His-Phe-Arg-D-Trp-Gaba-Cys)-NH$_2$ | 5.20 | 150 | 138 | 20.3 | 0.04 | SEQ ID NO: 37 |
| Ac-Nle-c(Asp-D-Ala-His-D-Phe-Arg-Bal-Ala-Lys)-NH$_2$ | 4.89 | 290 | 21.3 | 11.1 | 0.23 | SEQ ID NO: 58 |
| Ac-Nle-c(Cys-D-Ala-His-D-2-Nal-Arg-Trp-Cys)-NH$_2$ | 25.5 | 3.82 | 7.61 | 102 | 3.35 | SEQ ID NO: 16 |
| Ac-Nle-c(Cys-D-Ala-His-D-2-Nal-Arg-2-Nal-Cys)-NH$_2$ | 32.5 | 5.85 | 2.53 | 94.6 | 12.85 | SEQ ID NO: 16 |
| Ac-Nle-c(Cys-D-Ala-His-D-2-Nal-Arg-Bal-Cys)-NH$_2$ | 22.2 | 12.7 | 16.6 | 125 | 1.34 | SEQ ID NO: 20 |
| Ac-Nle-c(Asp-His-D-2-Nal-Arg-Trp-Ala-Lys)-NH$_2$ | 1.17 | 1.56 | 0.277 | 3.24 | 4.22 | SEQ ID NO: 38 |
| Ac-Nle-c(Asp-His-D-2-Nal-Arg-Trp-β-Ala-Lys)-NH$_2$ | 0.648 | 2.78 | 0.329 | 1.4 | 1.97 | SEQ ID NO: 38 |
| Ac-Nle-c(Cys-His-D-2-Nal-Arg-Trp-Gaba-Cys)-NH$_2$ | 0.393 | 1.86 | 0.375 | 1.11 | 1.05 | SEQ ID NO: 39 |
| Ac-Nle-c(Cys-His-D-2-Nal-Arg-Trp-Ahx-Cys)-NH$_2$ | 0.333 | 2.91 | 0.998 | 0.366 | 0.33 | SEQ ID NO: 39 |
| Ac-hPhe-c(Asp-His-D-2-Nal-Arg-Trp-Gaba-Lys)-NH$_2$ | 0.461 | 2.45 | 0.931 | 1.37 | 0.50 | SEQ ID NO: 40 |
| Ac-Cha-c(Asp-His-D-2-Nal-Arg-Trp-Gaba-Lys)-NH$_2$ | 0.576 | 3.98 | 2.82 | 3.91 | 0.20 | SEQ ID NO: 40 |

TABLE 2C

| Compound | Ki hMC1-R | Ki hMC3-R | Ki hMC4-R | Ki hMC5-R | Ki hMC1-R/ MC4-R | SEQ ID NO: |
|---|---|---|---|---|---|---|
| Ac-Arg-c(Cys-D-Ala-His-D-2-Nal-Arg-Trp-Cys)-NH$_2$ | 17.9 | 1.68 | 0.256 | 23.4 | 69.9 | SEQ ID NO: 49 |

Cyclic AMP Bioassay

Intracellular cyclic AMP (cAMP) levels were determined by an electrochemiluminescence (ECL) assay (Meso Scale Discovery®, Gaithersburg, Md.; referred to hereinafter as MSD). CHO-K1 cells stably expressing the hMC receptor subtypes were suspended in RMPI 1640® assay buffer (RMPI 1640 buffer contains 0.5 mM isobutylmethylxanthine (IBMX), and 0.2% protein cocktail (MSD blocker A)). Transgenic CHO-K1 cells stably expressing hMC receptor subtypes 1, 3, 4 or 5 were dispensed at a density of approximately 7,000 cells/well in 384-well Multi-Array® plates (MSD) containing integrated carbon electrodes and coated with anti-cAMP antibody. Increasing concentrations of the test compounds were added and the cells were incubated for approximately 40 minutes at approximately 37° C. Following this incubation, lysis buffer (HEPES-buffered saline solution with MgCl$_2$ and Triton X-100® at ph 7.3) containing 0.2% protein cocktail and 2.5 nM TAG™ ruthenium-labeled cAMP (MSD) was added and the cells were incubated for approximately 90 minutes at room temperature. At the end of the second incubation period read buffer (Tris-buffered solution containing an ECL co-reactant and Triton X-100 at ph 7.8) was added and the cAMP levels in the cell lysates were immediately determined by ECL detection with a Sector Imager 6000 Reader® (MSD). Data were analyzed using a computer-assisted non-linear regression analysis (XL fit; IDBS) and reported as either an $EC_{50}$ value or a Kb value.

$EC_{50}$ represents the concentration of an agonist compound needed to obtain 50% of the maximum reaction response, e.g., 50% of the maximum level of cAMP as determined using the assay described above. The Kb value reflects the potency of an antagonist and is determined by Schild analysis. In brief, concentration-response curves of an agonist are carried out in the presence of increasing concentrations of an antagonist. The Kb value is the concentration of antagonist which would produce a 2-fold shift in the concentration-response curve for an agonist. It is calculated by extrapolating the line on a Schild plot to zero on the y-axis.

A selection of compounds was tested using the above-discussed assays and the results are reported in Tables 3A, 3B, 3C, and 3D.

TABLES 3A, 3B, 3C, and 3D—cAMP Bioassay
Data for Selected Compounds

TABLE 3A

| Compound | $EC_{50}$ hMC1-R | $EC_{50}$ hMC3-R | $EC_{50}$ hMC4-R | $EC_{50}$ hMC5-R | $EC_{50}$ hMC1-R/ MC4-R | SEQ ID NO: |
|---|---|---|---|---|---|---|
| Ac-Arg-c(Cys-D-Ala-His-D-Phe-Arg-Trp-Cys)-NH$_2$ | 5.79 | 5.25 | 0.313 | 1630 | 18.0 | SEQ ID NO: 50 |
| Ac-D-Arg-c(Cys-D-Ala-His-D-Phe-Arg-Trp-Cys)-NH$_2$ | 6.17 | 5.6 | 0.397 | 1020 | 16.0 | SEQ ID NO: 50 |
| Ac-D-Arg-c(Cys-D-Ala-His-D-Phe-Arg-Trp-Pen)-NH$_2$ | 26.5 | 10.5 | 0.493 | 2440 | 54.0 | SEQ ID NO: 51 |
| Ac-D-Arg-c(Cys-His-D-Phe-Arg-Trp-Gaba-Pen)-NH$_2$ | 8.43 | 32.4 | 0.959 | 2140 | 9.0 | SEQ ID NO: 52 |
| Ac-Arg-c(Cys-His-D-Phe-Arg-Trp-Gaba-Pen)-NH$_2$ | 4.23 | 8.09 | 0.719 | 23.2 | 6.0 | SEQ ID NO: 52 |
| Ac-Arg-c(Cys-D-Ala-His-D-Phe-Arg-Trp-Pen)-NH$_2$ | 48.3 | 13.3 | 0.79 | 10000 | 61.0 | SEQ ID NO: 51 |
| Ac-D-Arg-c(Asp-His-D-Phe-Arg-Trp-Ala-Lys)-NH$_2$ | 1.48 | 5.76 | 0.078 | 297 | 19.0 | SEQ ID NO: 53 |
| Ac-Arg-c(Asp-His-D-Phe-Arg-Trp-Ala-Lys)-NH$_2$ | 1.39 | 2.89 | 0.055 | 467 | 25.0 | SEQ ID NO: 53 |

ND = not determined

TABLE 3B

| Compound | $EC_{50}$ hMC1-R | $EC_{50}$ hMC3-R | $EC_{50}$ hMC4-R | $EC_{50}$ hMC5-R | $EC_{50}$ hMC1-R/ MC4-R | SEQ ID NO: |
|---|---|---|---|---|---|---|
| Ac-Nle-c(Cys-D-Ala-His-D-Phe-Arg-Trp-Cys)-NH$_2$ | 2.4 | 0.33 | 0.078 | 420 | 31 | SEQ ID NO: 7 |
| D-Phe-c(Cys-His-D-(Et)Tyr-Arg-Trp-β-Ala-D-Cys)-Thr-NH$_2$ | 0.35 | 1.1 | 0.11 | 0.37 | 3 | SEQ ID NO: 24 |
| Nle-c(Cys-His-D-Phe-Arg-Trp-Apn-Cys)-NH$_2$ | 0.31 | 0.27 | 0.018 | 3.1 | 17 | SEQ ID NO: 27 |
| Ac-Nle-c(Cys-His-D-Phe-Arg-Trp-Gaba-Pen)-NH$_2$ | 0.28 | 0.24 | 0.028 | 3.9 | 10 | SEQ ID NO: 32 |
| Nle-c(Cys-His-D-Phe-Arg-Trp-Gaba-Cys)-NH$_2$ | 0.37 | 0.1 | 0.021 | 1.7 | 18 | SEQ ID NO: 34 |

TABLE 3B-continued

| Compound | EC$_{50}$ hMC1-R | EC$_{50}$ hMC3-R | EC$_{50}$ hMC4-R | EC$_{50}$ hMC5-R | EC$_{50}$ hMC1-R/ MC4-R | SEQ ID NO: |
|---|---|---|---|---|---|---|
| Ac-Nle-c(Asp-His-D-Phe-Arg-Trp-β-Ala-Lys)-NH$_2$ | 0.834 | 0.145 | 0.128 | 2.79 | 6.52 | SEQ ID NO: 1 |
| Ac-Nle-c(Cys-His-D-Phe-Arg-Trp-Apn-Cys)-NH$_2$ | 0.76 | 0.199 | 0.0492 | 1.73 | 15.45 | SEQ ID NO: 2 |
| Ac-Cha-c(Asp-His-D-Phe-Arg-Trp-Gaba-Lys)-NH$_2$ | 3.26 | 0.189 | 0.0949 | 30.2 | 34.35 | SEQ ID NO: 6 |
| Ac-Nle-c(Asp-His-D-Phe-Arg-Trp-Gaba-Lys)-NH$_2$ | 1.37 | 0.628 | 0.131 | 3.48 | 10.46 | SEQ ID NO: 6 |
| Ac-hCha-c(Asp-His-D-Phe-Arg-Trp-Gaba-Lys)-NH$_2$ | 2.27 | 3.32 | 7.24 | 415 | 0.31 | SEQ ID NO: 11 |
| Ac-Nle-c(Pen-D-Ala-His-D-Phe-Arg-Trp-Cys)-NH$_2$ | ND | 1.89 | 0.531 | ND | ND | SEQ ID NO: 21 |
| Ac-Nle-c(Cys-D-Ala-His-D-Phe-Arg-Trp-Pen)-NH$_2$ | 14.3 | 2.03 | 0.183 | 2240 | 78.14 | SEQ ID NO: 22 |
| D-Phe-c(Cys-His-D-(Et)Tyr-hArg-Trp-β-Ala-D-Cys)-Thr-NH$_2$ | 0.345 | 2.71 | 5376 | 2.38 | 0.06 | SEQ ID NO: 24 |
| D-Phe-c(Cys-His-D-(Et)Tyr-hArg-Bip-β-Ala-D-Cys)-Thr-NH$_2$ | 0.685 | 81.8 | 86.9 | 31.8 | 0.01 | SEQ ID NO: 26 |
| Ac-Nle-c(Asp-D-Ala-His-D-Phe-Arg-Bal-Lys)-NH$_2$ | 0.931 | 3.22 | 1.65 | >10000 | 0.56 | SEQ ID NO: 28 |
| Ac-Nle-c(Cys-D-Leu-His-D-Phe-Arg-Trp-Cys)-NH$_2$ | 3.24 | 0.465 | 0.0915 | 78.5 | 35.41 | SEQ ID NO: 30 |
| Ac-Nle-c(Cys-D-Cha-His-D-Phe-Arg-Trp-Cys)-NH$_2$ | 0.819 | 0.541 | 0.453 | 45.3 | 1.81 | SEQ ID NO: 30 |

ND = not determined

TABLE 3C

| Compound | EC50 hMC1-R | Kb hMC3-R | Kb MC4-R | EC50 hMC5-R | SEQ ID NO: |
|---|---|---|---|---|---|
| Ac-Nle-c(Cys-D-Ala-His-D-2-Nal-Arg-Trp-Cys)-NH$_2$ | 17.6 | 12.4 | 38.8 | 11.8 | SEQ ID NO: 16 |
| Ac-Nle-c(Asp-His-D-2-Nal-Arg-Trp-Ala-Lys)-NH$_2$ | 0.619 | 2.98 | 0.109 | 0.189 | SEQ ID NO: 38 |
| Ac-Nle-c(Asp-His-D-2-Nal-Arg-Trp-β-Ala-Lys)-NH$_2$ | 0.913 | 0.536 | 0.346 | 0.489 | SEQ ID NO: 38 |
| Ac-Nle-c(Cys-His-D-2-Nal-Arg-Trp-Gaba-Cys)-NH$_2$ | 0.231 | 18.4 | 0.782 | 0.153 | SEQ ID NO: 39 |
| Ac-Nle-c(Cys-His-D-2-Nal-Arg-Trp-Ahx-Cys)-NH$_2$ | 0.581 | 10.8 | 0.967 | 0.126 | SEQ ID NO: 39 |

TABLE 3C-continued

| Compound | EC50 hMC1-R | Kb hMC3-R | Kb MC4-R | EC50 hMC5-R | SEQ ID NO: |
|---|---|---|---|---|---|
| Ac-hPhe-c(Asp-His-D-2-Nal-Arg-Trp-Gaba-Lys)-NH$_2$ | 0.413 | 9.32 | 0.824 | 0.307 | SEQ ID NO: 40 |
| Ac-Cha-c(Asp-His-D-2-Nal-Arg-Trp-Gaba-Lys)-NH2 | 1.27 | 3.02 | 0.442 | 0.736 | SEQ ID NO: 40 |
| Ac-Nle-c(Cys-D-Ala-His-D-2-Nal-Arg-1-Nal-Cys)-NH$_2$ | 383 | 61.5 | 53.6 | 2842 | SEQ ID NO: 16 |

TABLE 3D

| Compound | EC50 hMC1-R | Kb hMC3-R | Kb MC4-R | EC50 hMC5-R | SEQ ID NO: |
|---|---|---|---|---|---|
| Ac-Arg-c(Cys-D-Ala-His-D-2-Nal-Arg-Trp-Cys)-NH$_2$ | 193 | 5.72 | 1.58 | 1111 | SEQ ID NO: 49 |

Example 4

In vivo Studies

Compounds of the present invention can be and were tested for an effect upon food intake and/or body weight according to the following procedures. One skilled in the art would know that procedures similar to those described herein may be used to assay the effect of the compounds of the invention upon food intake and/or body weight.

Ligand compounds activating melanocortin receptors tested in the in vivo studies were as follows (Table 4):

TABLE 4

| Ligand Code | Structure | |
|---|---|---|
| Compound A | Ac-Nle-c(Cys-D-Ala-His-D-Phe-Arg-Trp-Cys)-NH$_2$ | SEQ ID NO: 7 |
| Compound B | Ac-Nle-c(Cys-D-Ala-His-D-Phe-Arg-Trp-Pen)-NH$_2$ | SEQ ID NO: 22 |
| Compound C | Ac-Nle-c(Cys-His-D-Phe-Arg-Trp-Gaba-Pen)-NH$_2$ | SEQ ID NO: 32 |
| Compound D | D-Phe-c(Cys-His-D-(Et)Tyr-Arg-Trp-β-Ala-D-Cys)-Thr-NH$_2$ | SEQ ID NO: 24 |
| Compound E | Ac-Arg-c(Cys-D-Ala-His-D-Phe-Arg-Trp-Cys)-NH$_2$ | SEQ ID NO: 50 |
| Compound F | Ac-D-Arg-c(Cys-D-Ala-His-D-Phe-Arg-Trp-Cys)-NH$_2$ | SEQ ID NO: 50 |
| Compound G | Ac-D-Arg-c(Cys-D-Ala-His-D-Phe-Arg-Trp-Pen)-NH$_2$ | SEQ ID NO: 51 |

Acute Feeding Experiments (Fasting)

Male Sprague Dawley rats (250 g) were housed in individual cages and maintained under 12:12 hour light:dark conditions. The rats were fasted for 18 hours prior to the start of the experiment with water available ad libitum. At time 0, the rats were injected subcutaneously (sc) with selected compounds at doses of either 500 or 100 nmole/kg, or with vehicle, and were provided with food. Individual food consumption was measured at about 1, 2, 3, 4, 5 and 6 hours after injection. Data for selected compounds of the invention are reported in FIGS. 1A and 1B.

Acute Feeding Experiments (Non Fasting)

Male Sprague Dawley rats (250 g) are housed in individual cages and maintained under 12:12 hour light:dark conditions. Food and water is available ad libitum throughout the experiment. At time 0, the rats are injected sc with compound at doses of either 500 or 100 nmole/kg, or with vehicle. Individual food consumption is measured at about 1, 2, 3, 4, 5 and 6 hours after injection.

Chronic Feeding Experiments

Figure 2B:
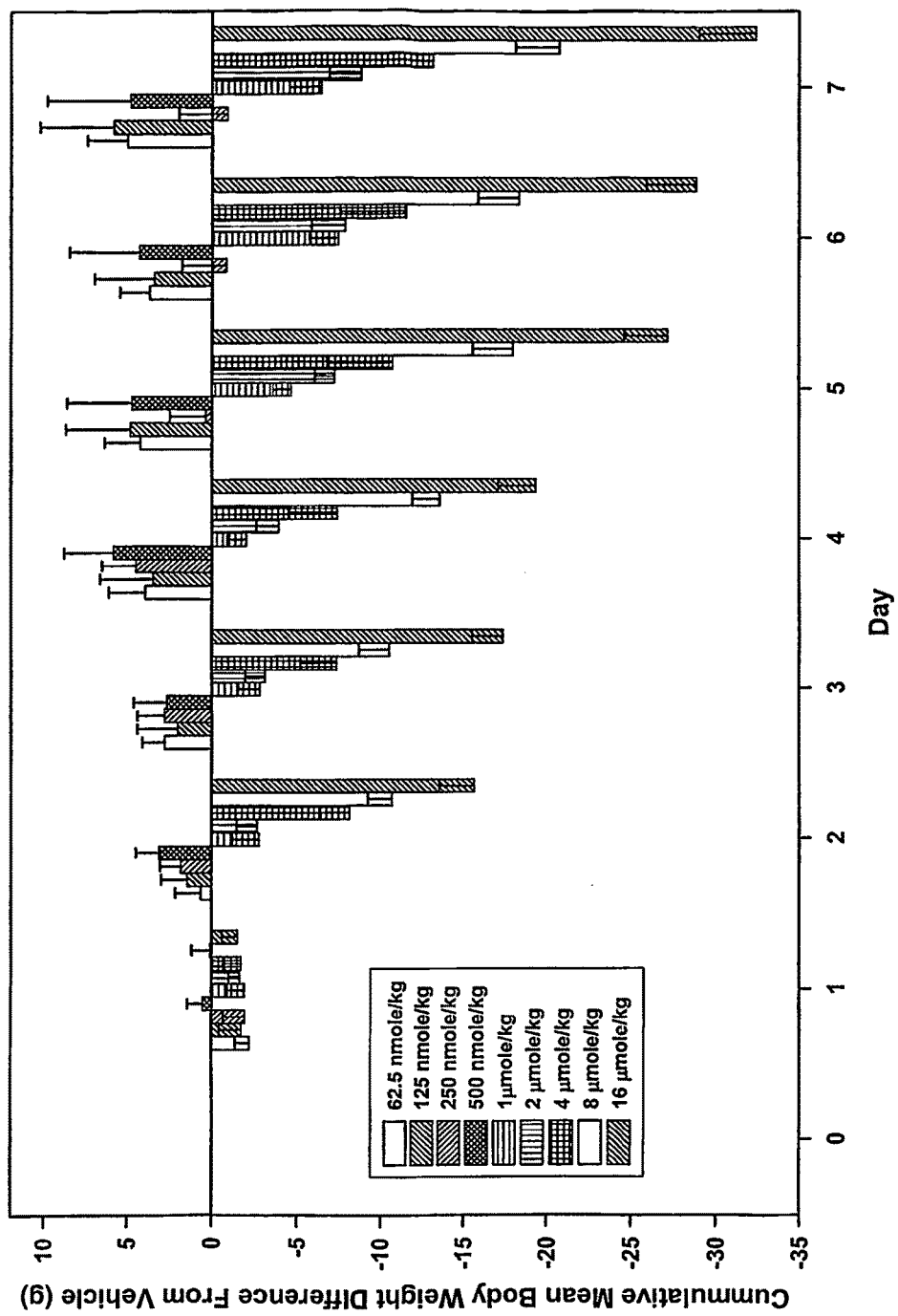
FIG. 2B. Cumulative mean body weight difference from vehicle in rats after administration of various concentrations of Compound A.
Figure 3A:
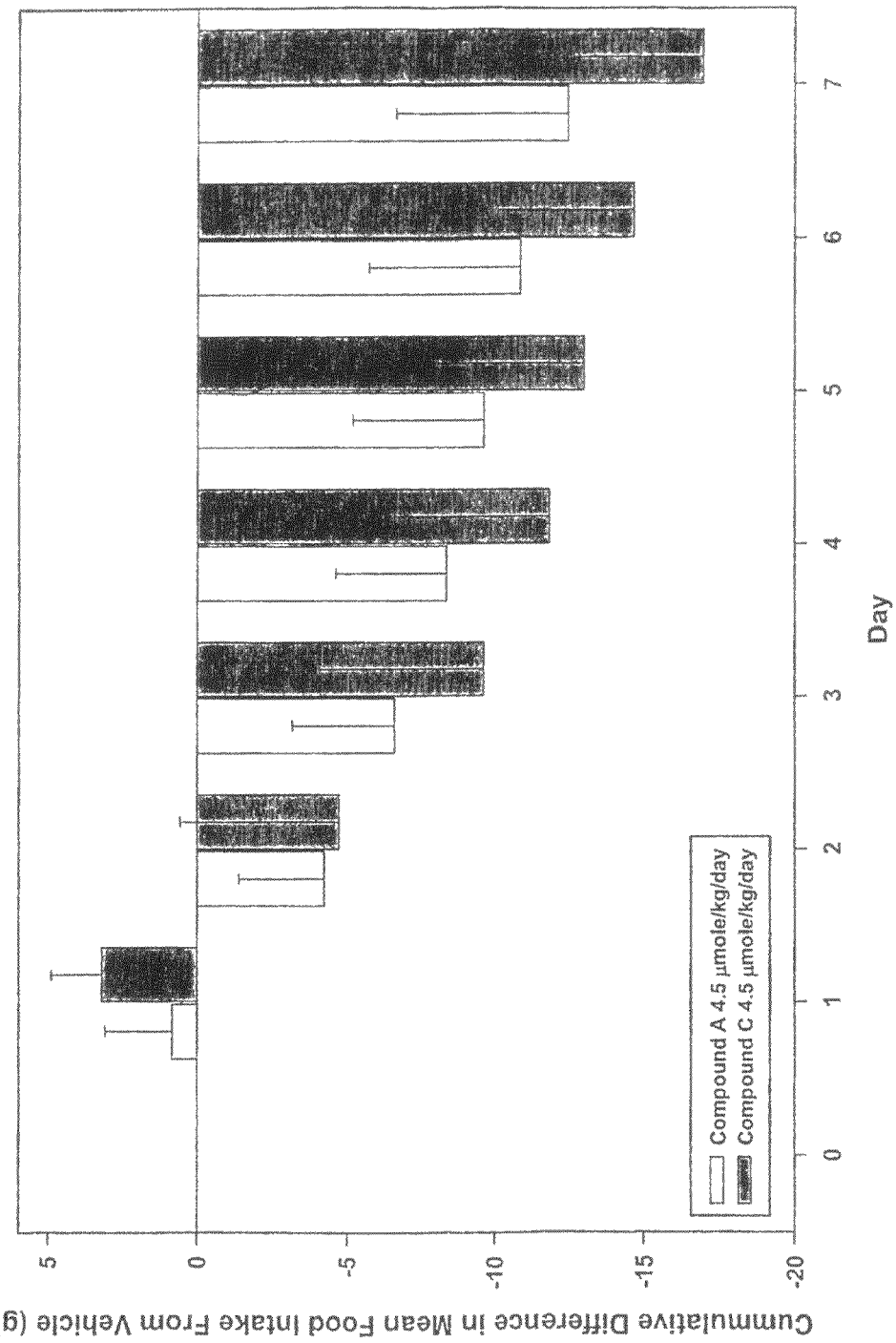
FIG. 3A. Cumulative difference in mean food intake from vehicle in rats after administration of selected compounds.
Figure 3B:
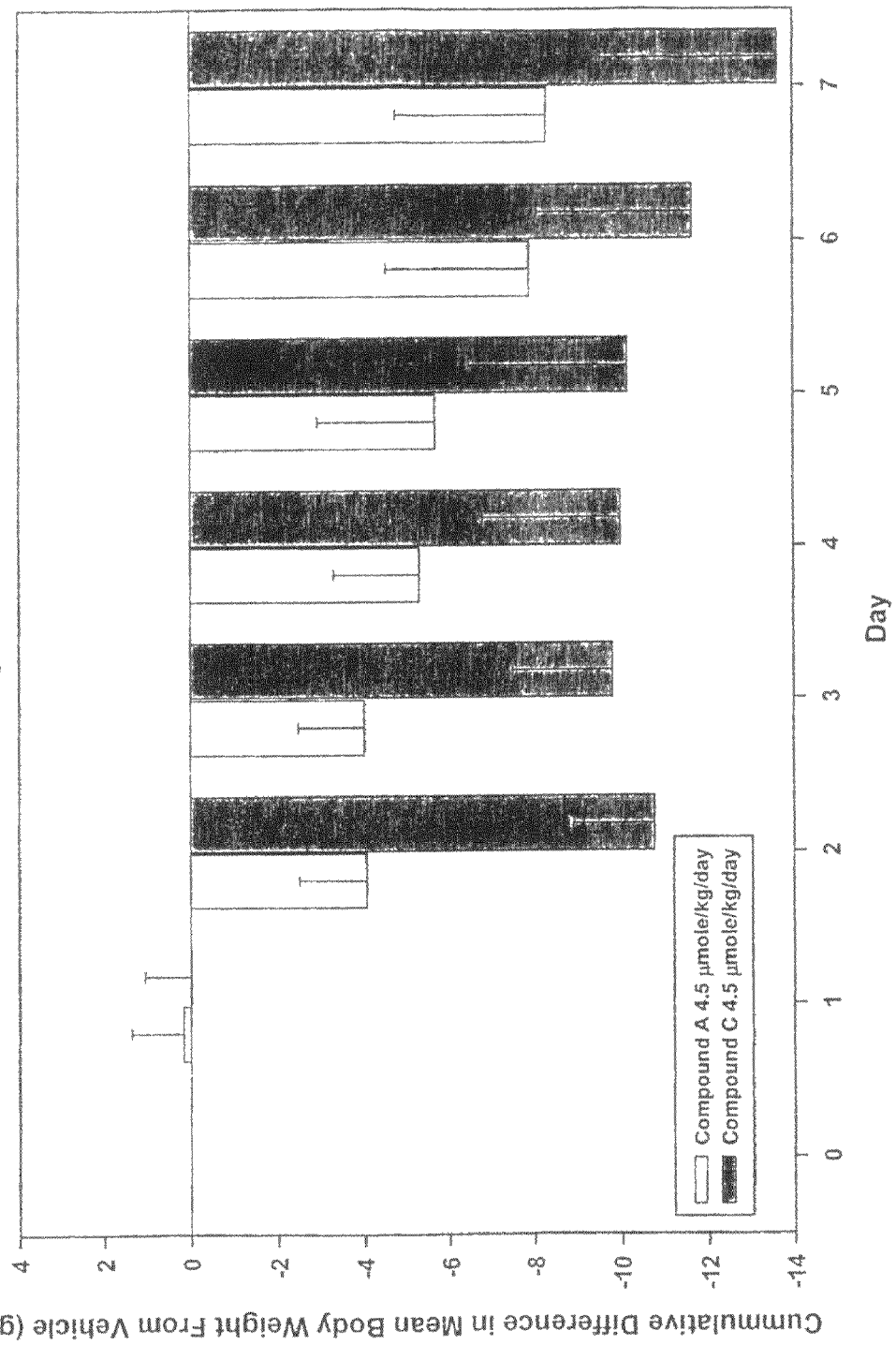
FIG. 3B. Cumulative mean body weight difference from vehicle in rats after administration of selected compounds.
Figure 4B:
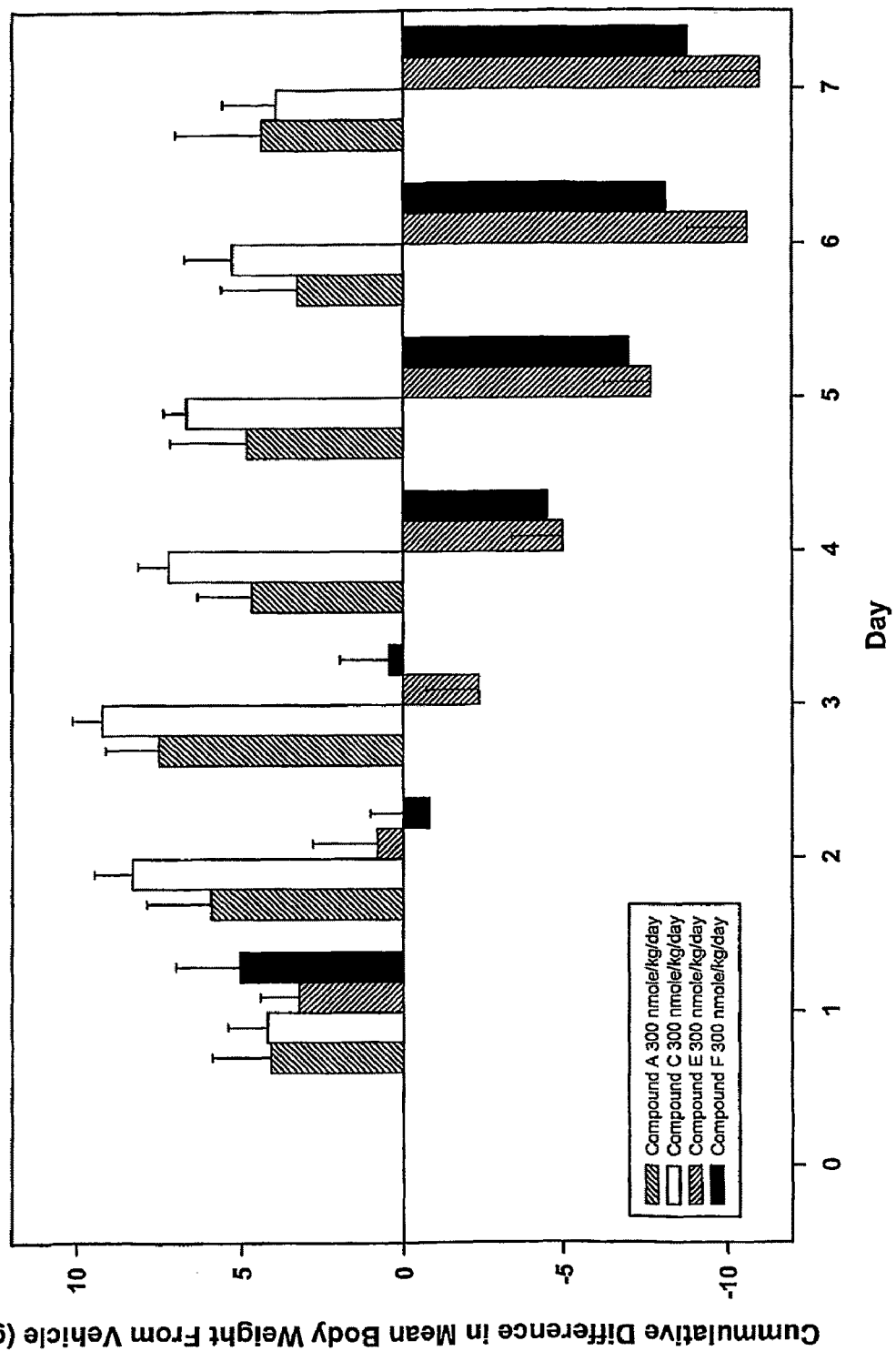
FIG. 4B. Cumulative mean body weight difference from vehicle in rats after administration of selected compounds.

Male Sprague Dawley rats (250 g) were housed in individual cages and maintained under 12:12 hour light:dark conditions with both food and water available ad libitum. The rats were injected sc 3×/day (approximately 0800 hour, 1200 hour, and 1600 hour) with compound at various doses or with vehicle for 7 days. Individual body weight and food consumption were measured daily. Data for selected compounds of the invention are reported in FIGS. 2A and 2B, FIGS. 3A and 3B, and FIGS. 4A and 4B.

Administration and Use

The peptides of this invention can be provided in the form of pharmaceutically acceptable salts. Examples of such salts include, but are not limited to, those formed with organic acids (e.g., acetic, lactic, maleic, citric, malic, ascorbic, succinic, benzoic, methanesulfonic, toluenesulfonic, or pamoic acid), inorganic acids (e.g., hydrochloric acid, sulfuric acid, or phosphoric acid), and polymeric acids (e.g., tannic acid, carboxymethyl cellulose, polylactic, polyglycolic, or copolymers of polylactic-glycolic acids). A typical method of making a salt of a peptide of the present invention is well known in the art and can be accomplished by standard methods of salt exchange. Accordingly, the TFA salt of a peptide of the present invention (the TFA salt results from the purification of the peptide by using preparative HPLC, eluting with TFA containing buffer solutions) can be converted into another salt, such as an acetate salt, by dissolving the peptide in a small amount of 0.25 N acetic acid aqueous solution. The resulting solution is applied to a semi-prep HPLC column (Zorbax®, 300 SB, C-8). The column is eluted with: (1) 0.1N ammonium acetate aqueous solution for 0.5 hours; (2) 0.25N acetic acid aqueous solution for 0.5 hours; and (3) a linear gradient (20% to 100% of solution B over 30 minutes) at a flow rate of 4 ml/min (solution A is 0.25N acetic acid aqueous solution; solution B is 0.25N acetic acid in acetonitrile/water, 80:20). The fractions containing the peptide are collected and lyophilized to dryness.

As is well known to those skilled in the art, the known and potential uses of peptides with melanocortin receptor (MC-R) agonist or antagonist activity is varied and multitudinous, thus the administration of the compounds of this invention for purposes of eliciting an agonist effect can have the same effects and uses as melanocortin itself.

Accordingly, the present invention includes within its scope pharmaceutical compositions comprising, as an active ingredient, at least one of the compounds of formula (I) in association with a pharmaceutically acceptable carrier.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. In general, an effective dosage for the activities of this invention is in the range of $1 \times 10^{-7}$ to 200 mg/kg/day, preferably $1 \times 10^{4}$ to 100 mg/kg/day which can be administered as a single dose or divided into multiple doses.

The compounds of this invention can be administered by oral, parenteral (e.g., intramuscular; intraperitoneal, intravenous or subcutaneous injection, or implant), nasal, vaginal, rectal, sublingual or topical routes of administration and can be formulated with pharmaceutically acceptable carriers to provide dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than such inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. Preparations may be sterilized by, for example, filtration through a bacteria-retaining filter, by incorporating sterilizing agents into the compositions, by irradiating the compositions, or by heating the compositions. Preparations can also be manufactured in the form of sterile solid compositions which can be dissolved in sterile water or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

Further, a compound of this invention can be administered in a sustained release composition such as those described in the following patents and patent applications. U.S. Pat. No. 5,672,659 teaches sustained release compositions comprising a bioactive agent and a polyester. U.S. Pat. No. 5,595,760 teaches sustained release compositions comprising a bioactive agent in a gelable form. U.S. Pat. No. 5,821,221 teaches polymeric sustained release compositions comprising a bioactive agent and chitosan. U.S. Pat. No. 5,916,883 teaches sustained release compositions comprising a bioactive agent and cyclodextrin. The teachings of the foregoing patents and applications are incorporated herein by reference.

What is claimed is:

1. A melanocortin-4 selective receptor agonist compound having the formula:

Ac-Arg-c(Cys-D-Ala-His-D-Phe-Arg-Trp-Cys)-NH$_2$;
(SEQ ID NO:50)

or a pharmaceutically acceptable salt thereof.

2. A pharmaceutical composition comprising a therapeutically effective amount of a melanocortin-4 selective receptor agonist compound having the formula Ac-Arg-c(Cys-D-Ala-His-D-Phe-Arg-Trp-Cys)-NH$_2$ (SEQ ID NO:50), or a pharmaceutically acceptable salt thereof, and a pharmaceutically acceptable carrier or diluent.

* * * * *